(12) United States Patent
Hopkins et al.

(10) Patent No.: US 10,381,110 B2
(45) Date of Patent: Aug. 13, 2019

(54) MOLECULES

(71) Applicant: University of Dundee, Dundee (GB)

(72) Inventors: Andrew Lee Hopkins, City Quay (GB); Jérémy Besnard, Dundee (GB)

(73) Assignee: UNIVERSITY OF DUNDEE, Dundee (GB)

( * ) Notice: Subject to any disclaimer, the term of this patent is extended or adjusted under 35 U.S.C. 154(b) by 461 days.

(21) Appl. No.: 14/986,516

(22) Filed: Dec. 31, 2015

(65) Prior Publication Data

US 2016/0196412 A1 Jul. 7, 2016

Related U.S. Application Data

(63) Continuation of application No. 13/510,599, filed as application No. PCT/GB2010/051940 on Nov. 22, 2010, now abandoned.

(51) Int. Cl.
| | |
|---|---|
| *G06F 19/00* | (2018.01) |
| *G16C 20/50* | (2019.01) |
| *C40B 10/00* | (2006.01) |
| *G16C 20/70* | (2019.01) |

(52) U.S. Cl.
CPC .............. *G16C 20/50* (2019.02); *C40B 10/00* (2013.01); *G16C 20/70* (2019.02)

(58) Field of Classification Search
None
See application file for complete search history.

(56) References Cited

U.S. PATENT DOCUMENTS

2012/0265514 A1   10/2012   Hopkins et al.

OTHER PUBLICATIONS

Bender; "Bayesian Methods in Virtual Screening and Chemical Biology"; Chemoinformatics and Computational Chemical Biology; vol. 672, pp. 175-196 (2011 ).
Brenk, et al.; "Lessons Learnt from Assembling Screening Libraries for Drug Discovery for Neglected Diseases"; ChemMedChem; vol. 3, pp. 435-444 (2008).
Brown, et al.; "A Graph-Based Genetic Algorithm and Its Application to the Multiobjective Evolution of Median Molecules"; J. Chem. Inf. Comput. Sci.; vol. 44, No. 3, pp. 1079-1087 (May 5, 2004).
Brown, et al.; "A Novel Workflow for the Inverse QSPR Problem Using Multiobjective Optimization"; J. Comput. Aided Mol. Des.; vol. 20, pp. 333-341 (Sep. 21, 2006).
Brown, et al.; "The De Novo Design of Median Molecules Within a Property Range of Interest"; Journal of Computer-Aided Molecular Design; vol. 18, pp. 761-771 (2004).
Cannon, et al.; "A Novel Hybrid Ultrafast Shape Descriptor Method for Use in Virtual Screening"; Chemistry Central Journal; vol. 2, No. 3 (Feb. 18, 2008).
Ertl, et al.; "Estimation of Synthetic Accessibility Score of Drug-Like Molecules Based on Molecular Complexity and Fragment Contributions"; Journal of Chem informatics; vol. 1, No. 8 (Jun. 10, 2009).
Final Office Action dated Jul. 2, 2015 in U.S. Appl. No. 13/510,599 by Hopkins, A., et al., filed May 17, 2012.
Final Office Action dated Nov. 22, 2013 in U.S. Appl. No. 13/510,599 by Hopkins, A., et al., filed May 17, 2012.
Gleeson, et al.; "Generation of a Set of Simple, Interpretable ADMET Rules of Thumb"; Journal of Medicinal Chemistry; vol. 51, No. 4, pp. 817-834 (Jan. 31, 2008).
Handl, et al.; "Multiobjective Optimization in Bioinformatics and Computational Biology"; IEEE/ACM Transactions on Computational Biology and Bioinformatics; vol. 4, No. 2, pp. 279-292 (Apr.-Jun. 2007).
Hert, et al.; "Comparison of Topological Descriptors for Similarity-Based Virtual Screening Using Multiple Bioactive Reference Structures"; Org. Biomol. Chem.; vol. 2, pp. 3256-3266 (Sep. 29, 2004).
Hopkins, et al.; "Can We Rationally Design Promiscuous Drugs?"; Current Opinion in Structural Biology; Vo. 16, pp. 127-136 (Jan. 25, 2006).
Hughes, et al.; "Physiochemical Drug Properties Associated with In Vivo Toxicological Outcomes"; Bioorganic & Medicinal Chemistry Letters; vol. 18, pp. 4872-4875 (2008).
International Search Report and Written Opinion dated Jun. 15, 2011 of PCT Application No. PCT/GB2010/051940.
Kasprzak, et al., Structural and Multidisciplinary Optimization, vol. 22, Issue 3 (2001), pp. 208-218.
Klon, et al.; "Finding More Needles in the Haystack"; Journal of Medicinal Chemistry; vol. 47, No. 11, pp. 2743-2749 (Apr. 28, 2004).
Lameijer, et al.; "The Molecule Evolutor. An Interactive Evolutionary Algorithm for the Design of Drug-Like Molecules"; J. Chem. Inf. Model; vol. 46, No. 2, pp. 545-552 (Jan. 25, 2006).
Lipinski, et al.; "Experimental and Computational Approaches to Estimate Solubility and Permeability in Drug Discovery and Development Settings"; Advanced Drug Delivery Reviews; vol. 46, pp. 3-26 (2001).
Nicolaou, et al.; "De Novo Drug Design Using Multiobjective Evolutionary Graphs"; J. Chem. Inf. Model.; vol. 49, No. 2, pp. 295-307 (Jan. 26, 2009).
Nidhi, et al.; "Prediction of Biological Targets for Compounds Using Multiple-Category Bayesian Models Trained on Chemogenomics Databases"; J. Chem. Inf. Model.; vol. 46, No. 3, pp. 1124-1133 (2006).
Non-Final Office Action dated Dec. 29, 2014 in U.S. Appl. No. 13/510,599 by Hopkins, A., et al., filed May 17, 2012.
Non-Final Office Action dated Jul. 10, 2013 in U.S. Appl. No. 13/510,599 by Hopkins, A., et al., filed May 17, 2012.

(Continued)

*Primary Examiner* — Michael L Borin
(74) *Attorney, Agent, or Firm* — Perkins Coie LLP; Alberto Araiza; Viola T. Kung

(57) ABSTRACT

A method for computational drug design using an evolutionary algorithm, comprises evaluating virtual molecules according to vector distance (VD) to at least one achievement objective that defines a desired ideal molecule. In one method the invention comprises defining a set of n achievement objectives ($O^A_{1-n}$), where n is at least one; defining a population ($P_{G=0}$) of at least one molecule; selecting an initial population ($P_{parent}$) of at least one molecule ($I_1$-$I_n$) from the population ($P_{G=0}$); and evaluating members ($I_1$-$I_n$) of the initial population ($P_{parent}$) against at least one of the n achievement objectives ($O^A_{1-x}$), where x is from 1 to n.

21 Claims, 17 Drawing Sheets

(56) References Cited

OTHER PUBLICATIONS

Obrezanova, et al.; "Automatic QSAR Modeling of ADME Properties: Blood-Brain Barrier Penetration and Aqueous Solubility"; J. Comput. Aided Mol. Des.; vol. 22, pp. 431-440 (Feb. 14, 2008).
Obrezanova, et al.; "Gaussian Processes: A Method for Automatic QSAR Modeling of ADME Properties"; J. Chem. Inf. Model; vol. 47, No. 5, pp. 1847-1857 (Jun. 28, 2007).
Prathipati, et al.; "Global Bayesian Models for the Prioritization of Antitubercular Agents"; J. Chem. Inf. Model; vol. 48, No. 12, pp. 2362-2370 (2008).
Raymond, et al.; "Rationalizing Lead Optimization by Associating Quantitative Relevance with Molecular Structure Modification"; J. Chem. Inf. Model.; vol. 49, No. 8, pp. 1952-1962 (Jul. 15, 2009).
Rogers, et al.; "Extended-Connectivity Fingerprints"; J. Chem. Inf. Model.; vol. 50, No. 5, pp. 742-754 (Apr. 28, 2010).
Stewart, et al.; "Drug Guru: A Computer Software Program for Drug Design Using Medicinal Chemistry Rules"; Bioorganic & Medicinal Chemistry; vol. 14, pp. 7011-7022 (Jul. 25, 2006).
U.S. Appl. No. 13/510,599 by Hopkins, A., et al., filed May 17, 2012.
Veber, et al.; "Molecular Properties That Influence the Oral Bioavailability of Drug Candidates"; Journal of Medicinal Chemistry; vol. 45, No. 12, pp. 2615-2623 (May 11, 2002).
Wermuth, et al.; "Selective Optimization of Side Activities"; Journal of Medicinal Chemistry; vol. 47, No. 6, pp. 1303-1314(Feb. 13, 2004).
Xia, et al.; "Classification of Kinase Inhibitors Using a Bayesian Model"; Journal of Medicinal Chemistry; vol. 47, No. 18, pp. 4463-4470 (Aug. 4, 2004).
Daugan, et al.; "The Discovery of Tadalafil: A Novel and Highly Selective PDE5 Inhibitor. 2:2,3,6,7, 12, 12a-hexahydropyrazino [1 ',2':1 ,6]pyrido[3,4-b]indole-1,4-dione Analogues"; Journal of Medicinal Chemistry; vol. 46, No. 21, pp. 4533-4542 (Sep. 17, 2003).
Glick, et al.; "Enrichment of High-Throughput Screening Data with Increasing Levels of Noise Using Support Vector Machines, Recursive Partitioning, and Laplacian-Modified Naive Bayesian Classifiers"; J. Chem. Inf. Model; vol. 46, No. 1, pp. 193-200 (Dec. 3, 2005).
Triballeau, et al.; "Virtual Screening Workflow Development Guided by the 'Receiver Operating Characteristic Curve Approach. Application to High-Throughput Docking on Metabotropic Glutamate Receptor Subtype 4"; Journal of Medicinal Chemistry; vol. 48, No. 7, pp. 2534-2547 (Mar. 8, 2005).

A

Information about model1 Dopamine D2 receptor

The prediction is made using the model: Dopamine_Receptor_ECFP
Number of active to create the model: 5759
Mean of Actives: 53.7 and StdDev: 52.3
Mean of Inactives: -39.5 and StdDev: 48.6
estimated Best Cut Off Score: 14.9
With a score higher than estimated:
TP/FN: 4435/1324
FP/TN: 6320/203028

| Scoring for the model | | | | | |
|---|---|---|---|---|---|
| Total Accuracy | Positive Recall | Negative Recall | Precision | Enrichment Factor | Sum Score |
| 0.0286 | 0.0214 | 0.00638 | 0.412 | 0.428 | 0.0482 |

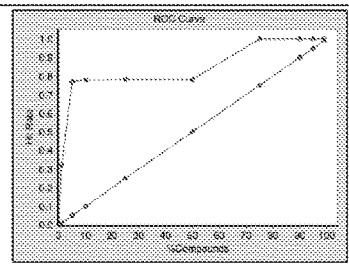

B

Information about model1 Dopamine D4 receptor

The prediction is made using the model: Dopamine_Receptor_ECFP
Number of active to create the model: 2017
Mean of Actives: 50.1 and StdDev: 49.5
Mean of Inactives: -29.6 and StdDev: 36.3
estimated Best Cut Off Score: 13.9
With a score higher than estimated:
TP/FN: 1498/519
FP/TN: 8025/205065

| Scoring for the model | | | | | |
|---|---|---|---|---|---|
| Total Accuracy | Positive Recall | Negative Recall | Precision | Enrichment Factor | Sum Score |
| 0.00938 | 0.00725 | 0.00251 | 0.157 | 0.164 | 0.0166 |

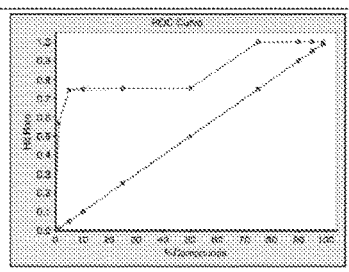

C

Information about model2 Acetylcholinesterase

The prediction is made using the model: Acetylcholinesterase_ECFP
Number of active to create the model: 1724
Mean of Actives: 69.0 and StdDev: 50.2
Mean of Inactives: -35.0 and StdDev: 46.9
estimated Best Cut Off Score: 6.4
With a score higher than estimated:
TP/FN: 1672/52
FP/TN: 40220/173161

| Scoring for the model | | | | | |
|---|---|---|---|---|---|
| Total Accuracy | Positive Recall | Negative Recall | Precision | Enrichment Factor | Sum Score |
| 0.00801 | 0.00956 | 0.000297 | 0.0399 | 0.0461 | 0.0178 |

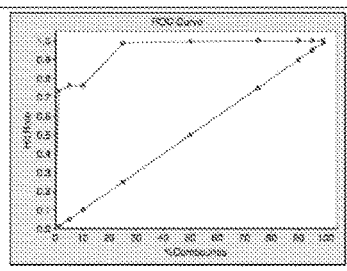

Figure 11

MOLECULES

CROSS REFERENCE TO RELATED APPLICATIONS

This is a continuation application of U.S. application Ser. No. 13/510,599, filed May 17, 2012; which claims the benefit of 35 U.S.C. 371 National Phase Entry Application from PCT/GB2010/051940, filed Nov. 22, 2010, which claims the benefit of United Kingdom Patent Application No. 0920382.9 filed Nov. 20, 2009, the disclosures of which are incorporated herein in their entirety by reference.

FIELD OF THE INVENTION

The invention relates to systems for the design and evolution of molecules, such as drugs. In particular, the invention relates to an in silico system for the design and optimisation of drugs that interact with selected target molecules, and to the drugs so designed.

BACKGROUND OF THE INVENTION

Medicinal chemistry is an iterative design process in which the biological properties of an analogous set of compounds are modified and assessed until a compound is discovered that meets required criteria for subsequent development. On average over one thousand compounds (at a cost of up to £2,000 each), may be synthesised and tested during the course of a drug discovery project, as it proceeds from an initial screening 'hit' to drug candidates for pre-clinical assessment. Therefore, the cost of developing new drug candidates can be extremely high even before clinical trials can be undertaken.

High-speed analogue chemistry library methods can be useful for producing a large number of low-cost compounds with relatively simple chemistries, to quickly explore the chemical space around an initial starting compound. However manual synthesis of individual compounds is usually unavoidable when a chemical series is to be optimised from a 'lead' to a clinical drug candidate, because specific, perhaps complicated, chemical design changes might be required.

Another problem in drug design is that during lead optimisation a number of independent, non-correlated (often divergent) properties may need to be optimised, such as: potency against a desired target; selectivity against non-desired targets; low probability of toxicity; and good drug metabolism and pharmacokinetic properties (ADME). To add to the complications, often the chemical changes that might most benefit one of these properties, such as target specificity, may be detrimental to another property, such as bioavailability. Therefore, the lead optimisation process can be considered as a complex multi-objective process.

Typically, the process of lead optimisation is based on a cycle of hypothesis generation and experimentation. Each compound design can be considered a 'hypothesis', which may be falsified by experimentation. The experimental results may be represented as structure-activity relationships, which generate a landscape of hypotheses as to which chemical structure is likely to contain the desired characteristics. The process of drug design is also an optimisation problem, as each project starts out with a product profile of desired attributes, e.g. a target function. The medicinal chemistry solution (i.e. a desired drug candidate profile), can be accurately described by its desired properties, for example: as a drug for administration by a preferred route (e.g. oral), having particular drug properties (e.g. solubility and bioavailability profiles), and a minimum degree of selectivity for the target molecule (e.g. at least 100-fold). However, even though the problem can be described, it is a difficult challenge to find an optimal solution from the vast space of hypothetical feasible solutions. In an attempt to overcome some of these commercial and technical problems, increasingly researchers are turning to artificial intelligence, e.g. software-based solutions and databases, which have been developed to automate parts of the iterative scientific discovery process.

Existing artificial intelligence-based approaches for drug design/evolution and lead optimisation can be generally categorised into three areas: (1) databases of chemical transformations for use in drug lead optimisation; (2) user-guided evolutionary drug design; and (3) automated evolutionary drug design. However, to date, none of the known systems offer the power, versatility and strategic intelligence that are required to achieve the desired levels of process simplification and cost savings.

(1) Chemical Transformations. In the process of drug design, the creative process of the chemist often utilises knowledge of 'tactics' or 'transformations', which can be applied in many situations to help design novel compounds. A creative transformation is often not just a simple chemical reaction leading to a new product, since many transformations may be required to duplicate several steps in a proposed synthetic route. Common tactics employed by the experienced medicinal chemist include, amongst others, 'methylene shuffle', adding lipophilicity, adding chirality, searching for hydrogen-bond interactions, and introducing or breaking conformational constraints. Previous attempts to catalogue lists of chemical transformations for use by medicinal chemists in the drug design process have been reported by Stewart K. D. et al. (2006) "Drug Guru: a computer software program for drug design using medicinal chemistry rules", *Bioorg. Med. Chem.*, 14(20), 7011-22; and Raymond J. W. et al., (2009) "Rationalizing lead optimization by associating quantitative relevance with molecular structure modification", *J. Chem. Inf. Model*, 49, 1952-62. Stewart K. D. et al. (2006) describes a database of chemical transformations that were derived from interviews with a number of medicinal chemists. The program takes an input compound, applies one generation of chemical transformations, and displays the resulting output structures for consideration by the medicinal chemist. Thus, the system acts as an 'ideas prompt', simply automating the thought process that would normally be undertaken by a medicinal chemist. Raymond J. W. et al., (2009) describes an alternative method of cataloguing chemical transformations. In this case, rather than rely on knowledge inputted from the real-life experiences of medicinal chemists, the authors attempted to systematically mine their own databases of medicinal chemistry structures. They identified 'similar' structures where the ratio of the number of bonds in the maximal common substructure in comparison to the maximum number of bonds in the compound is at least 0.7, thereby to automatically identify chemical transformations by comparison of those similar structures/compounds. However, no biological information was used in the selection of the transformations. Notably, neither of these systems of chemical transformations goes beyond the stage of simply presenting a host of potential transformed structures to the chemist for further consideration. Neither system scores compounds against a particular design goal, nor do they provide an automated, iterative closed loop system of hypothesis generation, assessment and redesign, which might alleviate the burden on the chemist to mentally and chemically assess the many possibilities.

(2) User-Guided Evolution. An alternative approach for generating compounds based on chemical knowledge of drug designs is a 'genetic algorithm'. Unlike the knowledge-based methods above, chemical transformations in a genetic algorithm are not defined by the creative or historical knowledge of medicinal chemistry, but are instead based on a simple set of genetic algorithm (or programmed) transformations to generate new compounds from a starting structure. These transformations can be categorised as 'crossover' (where substructures from two different molecules are selected and swapped) and 'mutation' (where a single atom or bond is changed using a small number of defined steps, e.g. add, insert, delete, replace etc.). Lameijer et al., (2006), "The Molecule Evaluator: An Interactive Evolutionary Algorithm for the Design of Drug-Like Molecules", *J. Chem. Inf. Model*, 46, 545-552, describes such an approach for proposing new chemical structures. As in the above knowledge-based systems, Lameijer et al., (2006) does not iteratively and automatically optimise compounds or score them in such a way as to identify best solutions; instead, it is down to the user to visually, mentally and chemically select and assess the possible molecules.

(3) Automated Evolution. This approach attempts to develop multi-objective methods using evolutionary approaches for drug design. Examples are reported in Brown et al., (2004), "A Graph-Based Genetic Algorithm and Its Application to the Multiobjective Evolution of Median Molecules", *J. Chem. Inf. Comput. Sci.*, 44, 1079-1087; and Nicolaou et al., (2009), "De Novo Drug Design Using Multiobjective Evolutionary Graphs", J. Chem. Inf. Model, 49, 295-307. Brown et al., (2004; see also Brown et al., 2004, "The de novo design of median molecules within a property range of interest", *J. Computer-Aided Mol. Design*, 18, 761-771; and Brown et al., 2006, "A novel workflow for the inverse QSPR problem using multiobjective optimization", *J. Computer-aided Mol. Design*, 20, 333-341) describes a genetic algorithm that generates novel compounds from compound 'fragments'. This system uses as its input a library of molecular fragments from which it builds new molecules via a genetic algorithm. The genetic algorithm builds compounds by randomly flipping segments in a population of graph-based 'chromosomes'. The mutations are atom/node based, such as append, prune, insert, or delete; or bond/edge based, such as add, delete, or substitute. A key feature of the method appears to be in defining of objectives as a chemical structure (or structures) that the system seeks to evolve compounds towards and, hence, maximise the structural similarity to an objective molecule (i.e. a defined 'median molecule'). The multi-objective genetic algorithm is defined by applying Pareto ranking to the designed compounds, and compounds that sit on the Pareto frontier (in terms of similarity with objective chemical structures) are prioritised. In the reported examples, none of the evolved compounds were validated as having any biological activity or particular utility. Furthermore, the system was not demonstrated in a method for drug discovery. Nicolaou et al. (2009) describes a de novo drug design algorithm using multi-objective evolutionary graphs. In this system, chemical structures are generated from a library of molecular building blocks, based on graph-based 'chromosomes', using mutation and crossover operations are previously described. An objective encoded scoring method is applied, which includes binding affinity predictions (mainly 3D protein structure docking), molecular similarity and chemical structure scores; and selection of molecules is based on Pareto ranking. Although an example of the method is applied to the in silico design of estrogen receptor alpha ligands, no experimental activity is reported for the designed compounds. Again, the authors indicate that this system is an 'ideas generator', rather than a validated, complete design system.

Hence, to date, none of the prior art has demonstrated utility in the design and prediction of active molecules that are valid drug candidates having desired biological activity. Therefore, there remains a need in the art for a truly automated drug design system, which goes beyond the level of simply automating the normal thought processes of a skilled person in the field, thereby aiding the medicinal chemist's decision making in compound design. There is a further need in the art for an in silico (or computer-based/software) drug design system that is capable of true lead optimisation, by assessing large numbers of hypothetical molecules and converging on a more limited number of potentially active molecules, thereby reducing the number of compounds that must be synthesised and tested during the course of a project. Moreover, there is an important unmet need in the art for an in silico system with demonstrable power and utility in the actual design and prediction of drug candidates having desired biological properties and activities. By satisfying one or more of these needs, the de novo drug design process may be simplified, and the costs of lead optimisation reduced, thereby having a direct impact on productivity in the field.

Another challenge in the art of drug design and evolution is in the area of 'polypharmacology'. While the dominant paradigm in drug discovery has traditionally been to design drugs (or ligands) with maximum selectivity against a specific target molecule; more recently in fields such as oncology, psychiatry and antimicrobials, it has been shown that effective drugs may act via modulation of multiple rather than single targets. In fact, advances in systems biology and network structures are now revealing that, in some cases, multi-target drugs may have greater clinical efficacy than exquisitely selective compounds. However, this recognition reveals further problems in the current systems and methods for rational drug design, because of the potential need for optimising multiple structure-activity relationships at the same time. None of the prior art systems provide a robust method for the design and evolution of drug candidates having desired polypharmacological profiles. Accordingly, there is a further need in the art for a computational (or in silico) system for the design and automatic optimisation of compounds having multiple activities.

The present invention addresses one or more of the above-mentioned problems in the prior art, by providing a computational system for 'intelligent' drug design and evolution.

SUMMARY OF THE INVENTION

In broad terms, the present invention provides methods for the design of molecules having desired properties, such as drugs capable of interacting with a chosen target molecule. The invention further provides molecules that have been selected to have particular properties for desired uses. The methods may involve computational means and, thus, the invention further provides computing devices programmed to perform the methods of the invention, and carrier mediums carrying the appropriate codes for controlling a device to perform the methods of the invention. The invention also generally involves evolutionary algorithms that generate successive populations of molecules and perform evaluations to identify molecules having or predicted to have the desired characteristics. The evolutionary algorithms may involve proprietary databases of chemical transformations that are used to generate new populations of molecules for assessment. The methods of the invention may be useful in a number of areas of molecular/drug design, including lead drug discover, multiple target polypharmacology, lead optimisation and optimisation of side/non-target activities of known molecules (e.g. drugs). Advantageously, therefore, the methods of the invention may be capable to evolving molecules to have desired pharmacological profiles against more than one target molecule, and having verifiable in vitro and in vivo activities. Accordingly, the methods of the invention enhance, simplify and/or reduce the costs and time that is invested in lead discovery and drug optimisation. In addition, the optimised molecules are generally based on actual molecular transformations, meaning that selected molecules can be readily synthesised, tested and further evolved if desired.

Thus, in a first aspect, the invention provides a method for computational drug design using an evolutionary algorithm. The method involves defining a set of n achievement objectives ($O^A_{1-n}$), where n is at least one, and defining a population ($P_{G=0}$) of at least one molecule. An initial population ($P_{parent}$) of at least one molecule ($I_1$-$I_n$) is selected from the population ($P_{G=0}$). Members ($I_1$-$I_n$) of the initial population ($P_{parent}$) are evaluated against at least one of the n achievement objectives ($O^A_{1-x}$), where x is from 1 to n. The evaluating of the members or molecule ($I_1$-$I_n$) comprises the calculation of vector distance (VD) to the at least one achievement objective ($O^A_{1-x}$). Generally, each of the members ($I_1$-$I_n$) is evaluated, so that the entire population ($P_{parent}$) can be assessed. Suitably, the value of x in the at least one achievement objective ($O^A_{1-x}$) is equal to n, such that the molecules are evaluated against all of the achievement objectives ($O^A_{1-n}$). However, it can be convenient to have x less than n so that processing speed can be improved; and alternatively, to guide or bias the selection of molecules towards particular objectives. It should be appreciated that the "n" of ($I_1$-$I_n$) merely represents the number of molecules in a population and is not connected with the number n of achievement objectives ($O^A_{1-n}$).

For some applications, the method further comprises generating further populations ($P_G$; $P_{G+1}$) of molecules and evaluating each one by an iterative process until a predefined stop condition is satisfied. The stop condition determines whether or not to generate and evaluate a further population of molecules. Therefore, the predetermined stop condition is conveniently satisfied only when one or more optimised molecules have been identified. Whether or not an optimised molecule or population of molecules has been achieved is defined by an internal definition.

In some embodiments the evaluating comprises assigning a vector distance (VD) and a Pareto frontier to each member ($I_1$-$I_n$) of the initial population ($P_{parent}$). A significant advantage of assigning a vector distance (VD) to each molecule is that it provides a linear and, therefore, unequivocal measure of the proximity of each molecule to the one or more achievement objectives. By contrast, the Pareto frontier ranking of any particular molecule, while providing a useful indication of certain properties of a molecule, may not be representative of the proximity of other parameters of the molecule to additional desirable activities. This may be a particularly important consideration where there is a plurality of achievement objectives against which a molecule is to be optimised, and against which a specific balance of properties may be required. For example, a molecule on a second, third or higher Pareto frontier may be linearly closer to a set of achievement objectives than molecules identified solely as being present in the first Pareto frontier. Hence, by relying solely on Pareto ranking, beneficial molecules (e.g. on a second or third Pareto frontier), or those that have great promise as drug leads for further evolution, may be lost or disregarded during the molecular evolution. By including Pareto frontier rank in the evaluation alongside vector distance (VD) an informed view of the relevance of the different calculations can be taken. Furthermore, promising molecules can be selected from different Pareto frontiers, thus expanding the pool of available, useful molecules for consideration. The most optimised molecule in any one evaluation is the molecule with the shortest vector distance (VD) to the achievement objectives, which is inevitably on the first Pareto frontier.

While different methods of evaluation may be used, suitably, the process of evaluating the molecules comprises: calculating the parameters of each member ($I_1$-$I_n$) of the initial population ($P_{parent}$) for each of the at least one achievement objective ($O^A_{1-x}$); and calculating the vector distance (VD) and optionally the Pareto frontier of each member ($I_1$-$I_n$) of the initial population ($P_{parent}$) to the set of achievement objectives ($O^A_{1-x}$). As already indicated, in some cases, the calculation of vector distance (VD) and optional Pareto frontier is based on all of the n achievement objectives ($O^A_{1-n}$). However, in other cases the calculation is based on one or more of the achievement objectives ($O^A_{1-x}$), which may not include all of the objectives.

Generally, the method further comprises determining whether a stop condition is satisfied. Typically, the stop condition is predetermined to either indicate that one or more optimised molecule has been achieved, or simply to halt the process once a suitable number of iterations of the method have been conducted.

When the stop condition is satisfied, the method may comprise the further steps of ranking each member ($I_1$-$I_n$) of the evaluated initial population ($P_{parent}$) according to vector distance (VD) and optionally Pareto frontier to the set of n achievement objectives ($O^A_{1-n}$). Thus, in this stage of the method, the molecules are evaluated against all of the n achievement objectives to ensure that all desired parameters of the molecules are predicted and assessed. Conveniently, at least the first ranked member ($I_1$-$I_n$) of the evaluated initial population ($P_{parent}$) is identified. This molecule is the molecule predicted to be the closest to the achievement objectives ($O^A_{1-n}$). Suitably, the ranking comprises: calculating the parameters of each member ($I_1$-$I_n$) of the initial population ($P_{parent}$) for each of the n achievement objectives ($O^A_{1-n}$); and calculating the vector distance (VD) and optionally the Pareto rank of each member ($I_1$-$I_n$) of the initial population ($P_{parent}$) to each of the n achievement objectives ($O^A_{1-n}$). The first ranked member, and hence, the most optimised molecule has the shortest vector distance (VD) to the set of n achievement objectives ($O^A_{1-n}$).

However, if the stop condition is not satisfied, the method may further Involve performing a first iteration (G=1) of the evolutionary algorithm to generate and evaluate a new population ($P_G$) of at least one molecule. In such embodiments, the method may comprise: transforming at least one member of the parent population ($P_{parent}$) to generate a transformed population ($P_{transformed}$) of at least one molecule; and defining a new population ($P_G$) of at least one molecule, the new population ($P_G$) comprising at least one member of the transformed population ($P_{transformed}$). Subsequently, a new population ($P_{G+1}$) of at least one molecule ($I_1$-$I_n$) is defined, and members ($I_1$-$I_n$) of the new population ($P_{G+1}$) are evaluated against the at least one achievement objective ($O^A_{1-x}$). As before, the molecules are evaluated by the calculation of vector distance (VD) to the at least one achievement objective ($O^A_{1-x}$). Typically, each member of the new population ($P_{G+1}$) is evaluated against the at least one achievement objective ($O^A_{1-x}$).

In this first iteration, as well as in any subsequent iterations, suitably, all of the members of the parent population ($P_{parent}$) are subjected to all of the available transformations, so as to maximise the pool of molecules in the transformed population ($P_{transformed}$). In some embodiments, the new population ($P_G$) is defined to include all of the members of the transformed population ($P_{transformed}$). In one embodiment, the new population ($P_G$) comprises the parent population ($P_{parent}$) and the transformed population ($P_{transformed}$). However, in alternative embodiments it may be convenient or desirable to include only a proportion of the transformed population ($P_{transformed}$) within the new population ($P_G$). Thus, the method may optionally include one or more filters (F) of predefined criteria, for removing unwanted or undesirable molecules from the transformed population ($P_{transformed}$) before defining the new population ($P_G$).

Having defined the new population ($P_G$), a strategy function (S) may then be employed to provide a further means of filtering out unwanted molecules. Beneficially, the Strategy function may be used to guide the selection and evolution of particular properties or an advantageous balance of properties. Thus, the method optionally includes evaluating the population ($P_G$) against at least one achievement objective ($O^A_{1-x}$), and selecting molecules from the evaluated population ($P_G$) by applying a strategy function (S).

As before, in these iterations, the evaluating step may comprise assigning a vector distance (VD) and a Pareto frontier to each member ($I_1$-$I_n$) of the new population ($P_{G+1}$). Furthermore, the evaluating may comprise the steps of calculating the parameters of each member ($I_1$-$I_n$) of the new population ($P_{G+1}$) for each of the at least one achievement objective ($O^A_{1-x}$); and calculating the vector distance (VD) and optionally the Pareto frontier of each member ($I_1$-$I_n$) of the new population ($P_{G+1}$) relative to the at least one achievement objective ($O^A_{1-x}$).

To determine whether or not to carry out further iterations of the method, the method may advantageously comprise determining whether a stop condition is satisfied. Thus, when the stop condition is not satisfied, the method suitably further comprises defining the evaluated new population ($P_{G+1}$) as a new parent population ($P_{parent}$) of at least one molecule ($I_1$-$I_n$); and performing a second iteration (G=2) of the evolutionary algorithm by repeating the steps of the Invention as described herein.

On the contrary, if the stop condition is satisfied (for the reasons given above) it can be beneficial to determine the ranking of each member in the final population to identify those that best satisfy the set of achievement objectives ($O^A_{1-n}$). Hence, in this embodiment, the method may further comprise ranking members ($I_1$-$I_n$) of the new population ($P_{G+1}$) according to vector distance (VD) and optionally Pareto frontier to the set of n achievement objectives ($O^A_{1-n}$); and identifying at least the first ranked member ($I_1$-$I_n$) of the evaluated new population ($P_{G+1}$). To rank the molecules, the method may involve calculating the parameters of each member ($I_1$-$I_n$) of the new population ($P_{G+1}$) for each of the n achievement objectives ($O^A_{1-n}$); and calculating the vector distance (VD) and optionally the Pareto frontier of each member ($I_1$-$I_n$) of the new population ($P_{G+1}$) to the n achievement objectives ($O^A_{1-n}$). The first ranked member is that molecule that has the predicted shortest vector distance (VD) to the achievement objectives ($O^A_{1-n}$).

Conveniently, the stop condition may be selected from: the number of iterations (G=n) of the evolutionary algorithm; a predefined vector distance (VD) of a predefined number or proportion of molecules in a population ($P_{parent}$; $P_G$; $P_{G+1}$) to one or more of the set of n achievement objectives ($O^A_{1-n}$); mean vector distance ([VD]Mean) of a population ($P_{parent}$; $P_G$; $P_{G+1}$) of molecules to one or more of the set of n achievement objectives ($O^A_{1-n}$); the rate of change in the mean vector distance ([VD]Mean) of successive evaluated populations ($P_{parent}$; $P_G$; $P_{G+1}$) of molecules; the rate of change in any other evaluated predefined criteria between successive populations ($P_{parent}$; $P_G$; $P_{G+1}$) of molecules; the predicted activity of one or more molecules for one or more of the achievement objectives; and/or the average complexity of virtual molecules. Another stop condition may be time dependent, such that the method is ended after a predefined period of time, for example, after approx. 48 hours or 72 hours.

As indicated, the method may further comprise applying at least one filter (F) to remove molecules that fail at least one predefined criteria of the filter (F). In this way, the populations for evaluation can be thinned out, thus increasing processing speed and manageability by removing molecules that are clearly inappropriate or that, for one reason or another, do not conform to predetermined requirements. Purely as an example, the transformations may result in a broken molecule, or one that would be undesirably reactive. Conveniently, the at least one filter (F) is applied to molecules of the population ($P_G$) before optionally evaluating the population ($P_G$) against at least one achievement objective ($O^A_{1-x}$), thus providing the benefit of reducing the amount of processing power required to perform the method. Advantageously, one of the at least one filters (F) removes any duplicate molecules from the population ($P_G$). In this regard, the transformations may include a "null-transformation" in which the starting molecule remains unaltered. In this case, the population ($P_{transformed}$) will necessary include all of the molecules in the starting population ($P_{parent}$). Therefore, the new population ($P_G$) need not comprise the starting population ($P_{parent}$). In any case, it can still be convenient to include a filter (F) to remove duplicate molecules, since duplicate molecules may also be generated through the transformation of similar molecules. Advantageously, the at least one filter (F) may also or alternatively be applied to molecules of the population ($P_{G+1}$) before ranking each member ($I_1$-$I_n$) of the new population ($P_{G+1}$).

The filter (F) may be based on any convenient criteria, such that undesirable molecules are removed from the population before further evaluation. Criteria such as reactivity, stability, solubility may be employed. For example, the at least one predefined criteria of the at least one filter (F) may be selected from at least one of: non-broken molecule requirement; solubility; drug-like properties, such as absorption, distribution, metabolism, and excretion (ADME); molecular weight; hydrogen bonding capacity; octanol-water partition coefficient; toxicity; unwanted group definition; total polar surface area; number of rotatable bonds, molecule size, e.g. number of atoms, number of rings, size of ring systems, number of functional groups (H-bond donors, H-bond acceptors), number of heteroatoms and so on.

The strategy function (S) is a particularly beneficial feature of the invention, in that it may enable the evolution and identification of molecules to be adjusted, guided or tailored to arrive at the molecule(s) having the most appropriate or desirable parameters, or when more than one parameter is of importance (as is generally the case), the most desirable blend of characteristics. Accordingly, in one particularly suitable embodiment, the method of the invention comprises: identifying at least one desired activity (A) of an optimised molecule and defining a strategy function (S) to score each member ($I_1$-$I_n$) of the population ($P_G$) against one or more of the at least one desired activity ($A_{1-n}$); calculating the parameters of each member ($I_1$-$I_n$) of the population ($P_G$) for at least one of the achievement objectives ($O^A_{1-x}$) relevant to the one or more desired activity ($A_{1-n}$); determining the predicted activity (Prediction 1 to Prediction n—where n depends on the number of activities selected) of each member ($I_1$-$I_n$) of the population ($P_G$) for the one or more desired activity ($A_{1-n}$); selecting the sub-population ($P_{elite}$) of molecules of the population ($P_G$) that satisfy the strategy function (S); and optionally selecting a sub-population ($P_{random}$) of at least one molecule from the sub-population ($P_{non-elite}$) of molecules that do not satisfy the strategy function (S). Preferably, the new population ($P_{G+1}$) of at least one molecule ($I_1$-$I_n$) comprises $P_{elite}$. In some embodiments, the new population ($P_{G+1}$) of at least one molecule ($I_1$-$I_n$) comprises the sub-populations $P_{elite}$ and $P_{random}$. Thus, the strategy function can be used to beneficially include molecules that might otherwise be removed and lost from the design process, but that might potentially lead to improved molecules in subsequent generations. By way of explanation, and without be bound by any particular theory, it may be that a molecule that ranks relatively lower in one iteration (e.g. lying on a second, third, fourth or $n^{th}$ Pareto frontier) when evaluated against a particular set of parameters, may ultimately provide molecules having a better blend of parameters after one or more further iterations of transformation. By selecting one or more molecules from the sub-population ($P_{non-elite}$) of molecules that do not satisfy the strategy function (S), the new population ($P_{G+1}$) comprises an enlarged genetic pool, which may contain a better mix of activities and properties. Conveniently, the at least one molecule ($P_{random}$) is selected at random from the sub-population ($P_{non-elite}$). However, in some embodiments, the sub-population ($P_{random}$) may be selected according to predetermined selection criteria, for example, to include molecules on the second, third, fourth or $n^{th}$ Pareto frontiers, or to select molecules having a particularly structure type (e.g. related derivatives).

One of skill in the art will appreciate that the strategy function (F) can be defined in a number of alternative ways in order to set a threshold above which the molecules are considered to satisfy the requirement. In one suitable embodiment, the strategy function (S) is satisfied for molecules of the population ($P_G$) where the predicted activity (Prediction 1) is greater than the sum of the mean predicted activity ([Prediction 1]Mean) and the standard deviation of the predicted activity ([Prediction 1]StdDev) for all members ($I_1$-$I_n$) of the population ($P_G$); i.e. where Prediction 1>[Prediction 1]Mean+[Prediction 1]StdDev.

In particularly beneficial embodiments of the invention, the strategy function (S) is based on two or more desired activities ($A_{1-n}$) of an optimised molecule. In this way, relative parameters of the optimised molecule can be prioritised, such as relative activity, specificity or selectivity for particular targets. Accordingly, the method is particularly suitable for selecting molecules having desirable polypharmacology profiles. For example, the at least one desired activity (A) of an optimised molecule may be selected from one or more of: predicted activity against one or more target molecule (e.g. specificity, binding affinity, inhibition constant); predicted relative activity against one target molecule compared to another molecule; predicted selectivity for one or more target molecule over another molecule; predicted relative selectivity for more than one target molecule; predicted drug-like properties/scores (e.g. ADME); prioritisation of one or more ADME property; prioritisation of drug-like properties over one or more activity or specificity; and prioritisation of vector optimisation over Pareto frontier. Preferred strategy functions include the prioritisation of one or more ADME property and/or the prioritisation of drug-like properties over one or more target activity or specificity.

The database of transformations is another advantageous feature of the invention. Although transformations based on genetic algorithms may be used in accordance with the invention, the transformation database is beneficially based on known (i.e. real-life) chemical transformations that the medicinal or organic chemist might choose to apply to particular molecules. Conveniently, the database is a proprietary database of known chemical transformations. Therefore, the generated transformations can be considered to be 'intelligent', in the sense that they may not generate a large proportion of impossible (e.g. broken, unstable or transient) or inappropriate (e.g. cannot be readily synthesised) molecules. In some embodiments it may be convenient to generate the database of transformations from a combination of known chemical transformations and genetic algorithms. Advantageously, all of the appropriate transformations are applied to all members of the population ($P_{parent}$).

In one variation, the method of the invention comprises transforming at least one of the molecules of the population ($P_{G=0}$), such as all of the molecules of $P_{G=0}$, to create a transformed population of molecules before selecting the initial population ($P_{parent}$). The initial population ($P_{parent}$) may comprise all of the molecules in the population ($P_{G=0}$). Suitably, however, the initial population ($P_{parent}$) of at least one molecule is selected from a larger population ($P_{G=0}$) of molecules based on at least one predetermined selection criteria. In this way, the starting point for the design process may include a degree of targeting. This can be particularly beneficial, for example, where additional properties/uses are being sought for known, existing molecules or drugs, such as in the case of optimising a side activity of a drug. Where the initial population ($P_{parent}$) is selected, the selection criteria could be any appropriate means of selection known to the person of skill in the art. For instance, suitable selection criteria include one or more of: 3D virtual docking, chemical similarity, database searching, Bayesian activity modelling, and an algorithm. In some advantageous embodiments the initial population ($P_{parent}$) of molecules consists of one molecule. In such cases, for example, where the starting molecule is a convenient or desirable known molecule or drug, it may not be necessary to previously and strictly define the population of molecules ($P_{G=0}$).

An important element of the invention is the appropriate definition of the achievement objectives, because these define the parameters of an ideal molecule, against which all other molecules will be assessed/judged. Typically, there will be a plurality of (i.e. n) different, perhaps related, achievement objectives ($O^A_{1-n}$) that define properties of a desired ideal molecule. The more achievement objectives the more specifically defined may be the ideal molecule, but the more difficult it may be to generate, design or evolve an optimised molecule to satisfy the requirements of the system. Thus, n may be 1 or more, such as between 1 and 20, or between 2 and 15. Typically, the number of achievement objections defined may be 5 or less, such as 1, 2, 3, 4 or 5. For example, the set of achievement objectives may include:

two activity predictions (e.g. binding affinity or inhibition constant against a target); an ADME prediction; and a target specificity prediction. Any desired activity, property or parameter of an ideal molecule may be used to set an achievement objective. Suitably, the set of n achievement objectives ($O^A_{1-n}$) includes at least one of: inhibition activity against a target molecule; binding affinity to a target molecule; specificity for a target molecule; selectivity for the target molecule over a non-target molecule; pharmacokinetic (ADME) properties; desirability scores; and ligand efficiency. The number of achievement objectives may also depend on the strategy chosen. For example, optimising a polypharmacology profile of a molecule while including objectives to avoid non-target molecules or "anti-targets" may lead to a large number of measured properties (e.g. up to 20). However, a single target optimisation may be implemented with as few as two achievement objectives (e.g. an activity prediction and an ADME prediction). In one advantageous embodiment, the definition of the set of n achievement objectives ($O^A_{1-n}$) includes parameters relating to interactions of an ideal molecule with two or more different target molecules or target sites to optimise polypharmacology.

Once the stop condition has been satisfied, the method may advantageously include an assessment and ranking of the final population ($P_{G+1}$) of molecules. In one such embodiment, the method of the invention further comprises: evaluating each of the members ($I_1$-$I_n$) of the new population ($P_{G+1}$) of molecules against the complete set of n achievement objectives ($O^A_{1-n}$); applying at least one filter (F); assigning to each molecule of the population ($P_{G+1}$) a vector distance (VD) and a Pareto frontier for the set of n achievement objectives ($O^A_{1-n}$); ranking (each) member(s) of the population ($P_{G+1}$) of molecules by vector distance to the set of n achievement objectives ($O^A_{1-n}$); ranking the members of the population ($P_{G+1}$) of molecules in at least the first Pareto frontier according to vector distance (VD) to the set of n achievement objectives ($O^A_{1-n}$), such that at least the first ranked member of the population ($P_{G+1}$) in at least the first Pareto frontier can be readily identified. More suitably, at least two filters (F) are applied, for example, filters (F) that may be applied in combination or sequentially include: an 'HTS' (high-throughput screening) filter, a 'rule of five' filter, a 'GSK' filter, and an unwanted groups filter. An HTS filter excludes molecules that are likely to be poor candidates for high-throughput screening, including those containing non-organic atom types, reactive substructures, and those with a molecular weight of greater than 150. A GSK filter is based on a bioavailability rule defined by Veber (2002, Molecular Properties That Influence the Oral Bioavailability of Drug Candidates, *J. Med. Chem.*, 45(12), 2615-2623), which filters molecules according to flexibility and polar surface area of the molecule. Thus, the HTS filter serves the purpose of providing a clean set of molecules for HTS screening purposes; the Rule of Five and GSK filters each help to provide bioavailable compounds; and the unwanted group definition filter helps to avoid the undesirable reactivity of compounds in the assays, or simply molecules having groups that can not be included in a pharmaceutical drug (e.g. for reason of toxicity). In this way, the molecules of the population ($P_{G+1}$) may be considerably reduced prior to final prioritisation and ranking. One or more of the above filters may also be used in intermediate generations of the method (rather than solely once the stop condition has been met), but time and processing power considerations may be taken into account in the selection of earlier filters. Other filters that may be used at this and other stages, alone or in combination/sequentially include: non-broken molecule requirement; solubility; drug-like properties, such as absorption, distribution, metabolism, and excretion (ADME); molecular weight; hydrogen bonding capacity; octanol-water partition coefficient; toxicity; unwanted group definition; total polar surface area; number of rotatable bonds.

The person of skill in the art will readily appreciate that the method of the invention further relates to the molecules identified as optimised molecules with respect to the predefined achievement objectives. Of course, it can be of benefit to synthesise any such identified, optimised molecules and determine their actual physical properties and characteristics. Accordingly, in a further embodiment, the invention comprises the steps of: selecting at least one molecule of the population ($P_{parent}$) or ($P_{G+1}$) based on its ranking; identifying the at least one selected molecule as an optimised molecule; and optionally synthesising the at least one selected molecule.

As already indicated, the invention may have utility in a method of lead (drug) optimisation, lead (drug) discovery, optimisation of side activities and/or multiple target polypharmacology.

In one suitable embodiment, the method is used for designing, predicting and/or selecting a molecule as an antagonist of phosphodiesterase 5 (PDE-5). In such an embodiment, the initial population ($P_{parent}$) may comprise tadalafil. In another embodiment the invention has utility in designing, predicting and/or selecting a molecule as an antagonist of dopamine D4 and/or as an antagonist of dopamine D2. In this embodiment, the initial population ($P_{parent}$) may beneficially comprise donepezil. In yet another suitable embodiment, the method is used for designing, predicting and/or selecting a molecule as an antagonist of aromatase. In this embodiment, the initial population ($P_{parent}$) may beneficially comprise fadrozole.

It should be appreciated that in this aspect of the invention, unless otherwise stated, any of the method steps of different embodiments can be combined to create a method in accordance with the invention.

In another aspect, the invention relates to molecules, compounds and/or drugs. In one embodiment, the invention thus provides a novel molecule identified by any of the methods of the first aspect of the invention. Particularly useful molecules of the invention may have binding activities or inhibition constants (Ki) for one or more target molecule in the range up to about 200 nM, up to about 100 nM, up to about 20 nM. Furthermore, they may exhibit selectivity for a target molecule of at least 10-fold over a defined non-target molecule, at least 50-fold, or at least 100-fold.

In a further, more specific embodiment, the invention provides a molecule selected from a molecule having a formula shown in FIG. 15, for example, a compound selected from GFR-VII-273, GFR-VII-274, GFR-VII-280-HCl, GFR-VII-280, GFR-VII-281, GFR-VII-285, GFR-VII-287, GFR-VII-290, STT-00185638, and STT-00185641. The invention also provides a compound selection from GFR-VII-273, GFR-VII-274, GFR-VII-280-HCl, GFR-VII-280, GFR-VII-281, GFR-VII-285, GFR-VII-287, GFR-VII-290, STT-00185638, and STT-00185641 for use in medicine. Thus the invention provides for the use of a compound of the invention in the manufacture of a medicament, and for pharmaceutical compositions comprising molecules/compounds of the invention.

The molecules, compounds and drugs of the invention may be formulated into pharmaceutical compositions.

Therefore, the invention also relates to pharmaceutical compositions comprising molecules of the invention (and a pharmaceutically acceptable carrier). In addition, it is envisaged that the molecules and pharmaceutical compositions of the invention may have pharmaceutical activity (in vitro, ex vivo or preferably in vivo) against one or more medical condition. Hence, the invention in another aspect, provides for the use of molecules of the invention in medicine; and for a use in treating specified medical indications or diseases associated with specified target molecules, such as a disease or condition associated with phosphodiesterase 5 (PDE-5) and/or dopamine D4 receptor, and/or dopamine D2 receptor. Uses for the molecules of the invention include the use of a molecule selected from GFR-VII-273, GFR-VII-274, GFR-VII-280-HCl, GFR-VII-280, GFR-VII-281, GFR-VII-285, GFR-VII-287, and GFR-VII-290 as an antagonist of the dopamine D4 receptor; and/or the use of a molecule selected from STT-00185638, and STT-00185641 as an antagonist of the dopamine D2 receptor. The use of the molecules of the invention in the treatments of diseases and conditions such as schizophrenia, Parkinson disease and/or myoclonus dystonia are also encompassed. Particularly suitable molecules of the invention for use in the inhibition of the dopamine D2 receptor and associated diseases and conditions are GFR-VII-285 and/or GFR-VII-269. Another particularly suitable molecule for use in the inhibition of the dopamine D4 receptor is STT-00185638.

In another aspect, there is provided a carrier medium for carrying a computer readable code for controlling a computing device to carry out any method of the first aspect of the invention.

In still a further aspect, the invention provides a computing device for computational drug design using an evolutionary algorithm, comprising: input means arranged to receive a set of n achievement objectives ($O^A_{1-n}$); processing means arranged to generate a population ($P_{G=0}$; $P_{parent}$) of at least one molecule and to evaluate the population ($P_{G=0}$; $P_{parent}$) against the n achievement objectives ($O^A_{1-n}$); and output means arranged to output results of the evaluation. As in the methods of the invention, the processing means is arranged to evaluate members of the population according to vector distance (VD) to the set of n achievement objectives ($O^A_{1-n}$) and optionally including Pareto frontier ranking. The computing device of the invention may further comprise input, processing and/or output means for performing any of the method steps of the invention described herein.

It will be understood that the method steps and features of the first aspect of the invention may be reproduced in software or hardware of the invention. Thus, these methods may be converted into computer readable form in any aspect relating to carrier mediums or computing devices of the invention.

These and other uses, features and advantages of the invention should be apparent to those skilled in the art from the teachings provided herein.

All references cited herein are incorporated by reference in their entirety.

BRIEF DESCRIPTION OF THE DRAWINGS

The invention is further illustrated with reference to the following drawings in which:

FIG. 11 illustrates the Bayesian biological activity models for predicting the activity of virtual compounds against the dopamine D2 receptor (A), the dopamine D4 receptor (B) and acetylcholinesterase (C). In (A), the number of actives to create the model was 5759; the mean of the actives was 53.7 and the standard deviation was 52.3; the mean of the inactives was −39.5 and the standard deviation of the inactives was 48.6; the estimated best cut-off score was 14.9; with a score higher than estimated, TP/FN: 4435/1324; FP/TN: 6320/203028. In (B), the number of actives to create the model was 2017; the mean of the actives was 50.1 and the standard deviation was 49.5; the mean of the inactives was −29.6 and the standard deviation of the inactives was 38.3; the estimated best cut-off score was 13.9; with a score higher than estimated, TP/FN: 1498/519; FP/TN: 8025/205065. In (C), the number of actives to create the model was 1724; the mean of the actives was 69.0 and the standard deviation was 50.2; the mean of the inactives was −35.0 and the standard deviation of the inactives was 46.5; the estimated best cut-off score was 6.4; with a score higher than estimated, TP/FN: 1672/52; FP/TN: 40220/173161;

DETAILED DESCRIPTION OF THE INVENTION

Figure 1:
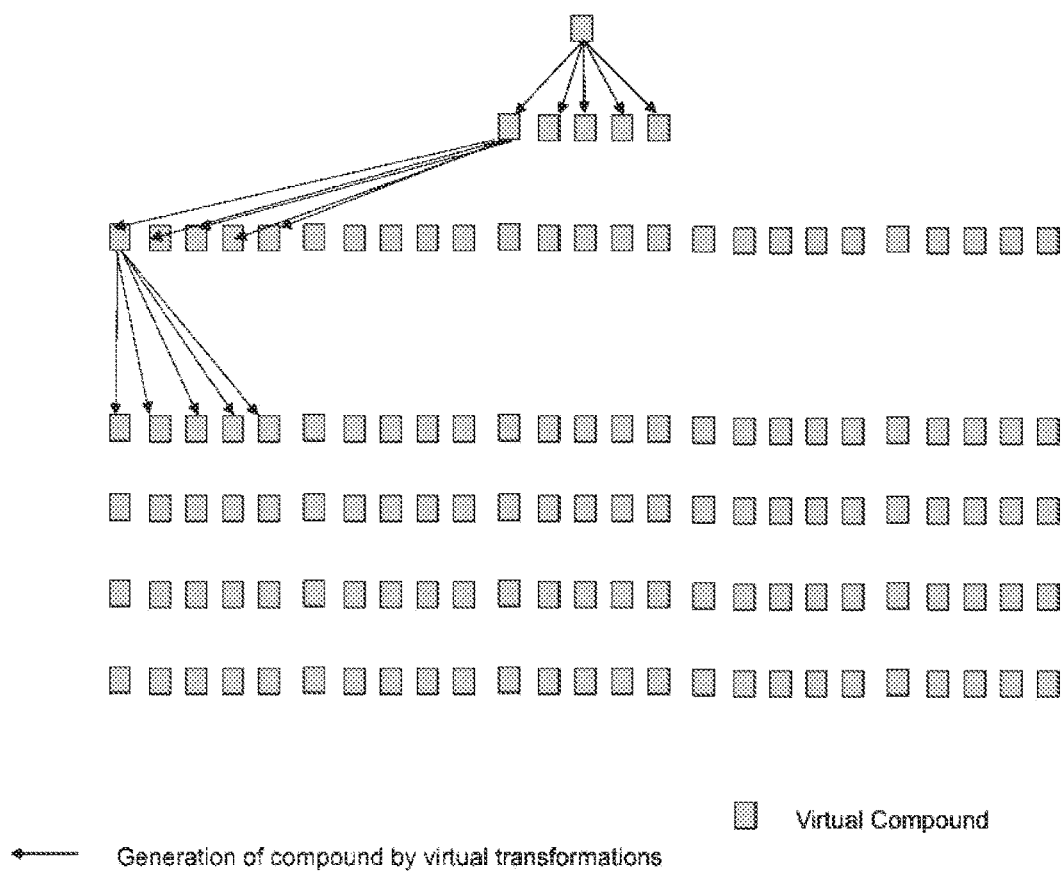
FIG. 1 illustrates the combinatorial expansion of virtual molecules by successive rounds of molecular transformation.

Prior to setting forth the detailed description of the invention, a number of definitions are provided that will assist in the understanding of the invention.

By 'ideal', as used herein, e.g. in the context of an 'ideal molecule', it is meant a molecule having specifically defined, desired properties or parameters. An ideal molecule in the context of the invention has parameters (or properties) that correspond exactly to the set of n achievement objectives that have been defined. In other words, the ideal molecule is the target molecule to which the method of the invention is directed. An ideal molecule does not necessarily correspond to a definable chemical structure: in fact, it may not be physically possible to actually design and synthesise a molecule having all of the exact properties of the ideal molecule. Hence, in contrast, an 'optimised' molecule is used herein to mean a designed or evolved molecule that satisfies (internally) predefined parameters that identify it as having achieved an acceptable predicted performance level (or a desired predicted set of activities or properties), but not necessarily the parameters of the n achievement objectives. In the context of the invention, therefore, an optimised molecule is one which has met the predefined requirements of the system/method of the invention: which for some applications may relate to the discovery of a lead molecule for further investigation or optimisation. For the avoidance of doubt, therefore, by 'optimised' (c.f. 'ideal'), it is not intended to suggest that the molecule has evolved to a point from which it would be physically impossible to arrive at an even more optimal molecule (e.g. by in vitro synthesis) having still more desirable properties.

By 'iterations' in the context of the invention, it is meant the number of cycles of population generation ($G_n$) and evaluation that are performed after the assessment of the initial parent population ($P_{parent}$). Thus, each iteration involves one round of chemical transformations to generate a new pool of molecules for assessment, and hence a new generation of molecules.

By 'transformation' it is meant the substitution, deletion or addition (and so on) of at least one and possibly more than one entity, such as a chemical bond, atom, moiety or group of bonds, atoms or moieties. Suitably, the transformations are real transformations in the sense that they are transformations that are achievable and preferably have already been achieved by (organic) chemical synthesis. Thus, a 'transformant' or transformed molecule is a new chemical structure that has been created or derived by transforming another molecule or chemical structure. A database of transformations is a plurality of such transformations, and may include a null-transformation (i.e. where the starting molecule is not transformed).

In accordance with the invention, the term 'molecule' or 'molecules' is used interchangeably with the terms 'compound(s)' and 'drug(s)', and sometimes a 'chemical structure'. The term 'drug' is typically used in the context of a pharmaceutical, pharmaceutical composition, medicament or the like, which has a known or predicted physiological or in vitro activity of medical significance; but such characteristics and qualities are not excluded in a molecule of the invention. The term 'therapeutic' is used interchangeably with 'pharmaceutical'. Therapeutics may include compositions as well as compounds and molecules.

In the context of the present invention, the terms 'individual', 'subject', or 'patient' are used interchangeably to indicate a human or other animal that may be suffering from a medical condition and may be responsive to a molecule, pharmaceutical drug, medical treatment or therapeutic treatment regime of the invention. An individual may be a human subject or an animal.

Molecular Design by Evolutionary Optimisation

Molecular or drug design can be considered a multi-dimensional optimisation problem that uses the hypothesis generation and experimentation cycle to advance knowledge. Each compound design can be considered a hypothesis which is falsified in experimentation. The experimental results are represented as structure-activity relationships, which construct a landscape of hypotheses as to which chemical structure is likely to contain the desired characteristics. The process of drug design is also an optimisation problem as each project starts out with a product profile— i.e. target function—of desired, specified attributes. The medicinal chemistry solution—a desired drug candidate profile—can also be accurately described, for example, "an oral, rule-of-five compliant, inhibitor of phosphodiesterase 5 with 100-fold selectivity over phosphodiesterases and with no structural alerts present". However, even though the objective can be accurately described, it has previously been an expensive and difficult challenge to find an optimal solution. One particular difficulty with this type of problem is to effectively navigate the vast space of feasible solutions, assessing those molecules found along the way.

Some significant benefits of the invention in generating and ranking drug-like compounds resides in the details of the methodology, for example: in the method of assessment/evaluation of proposed molecules; the selection strategy for the targeting of useful molecules; and in the manner of transforming molecules to generate new, useful and, importantly, practical molecules. The results presented herein, such as in the design and identification of phosphodiesterase 5 (PDE5) inhibitors and dopamine D2 and/or dopamine D4 antagonists, represent a major advance over the prior art and validate the method of the invention.

The methods described herein have a number of advantages over the previously disclosed methods for automated drug design. For instance, the invention has utility in the design and identification of lead compounds for a desired pharmaceutical target. Alternatively, the invention has utility in the optimisation and prioritisation of drugs from a lead compound. In another useful embodiment, the method of the invention has been shown to generate novel compounds having useful polypharmacology. Furthermore, the method of the invention can be used to propose one or more new, optimised molecules or chemical structures having desired activities from a starting point of either a single molecule or a group of molecules. One important application of the invention is in selectively optimising a side activity (or a weak or off-target activity) of a known drug into a new primary activity (e.g. selective optimisation of side activities, see Wermuth's SOSA).

Another significant advantage of the method of the invention is that it can encompass the entire drug/molecular design cycle, including: virtual compound generation; assessment of drug-like (ADMET) properties (from one of more methods of prediction); and assessment of predicted biological activities (single or multiple predictions), using one or more methods of predicting biological activity (e.g. Bayesian activity models, virtual screening, 3D-docking, pharmacophore modelling). Accordingly, the method can be completely automated such that, once a set of n achievement objectives ($O^A_{1-n}$) and an initial parent population ($P_{parent}$) of at least one molecule has been defined, the method may not require further input from a user in order to obtain predicted optimal molecules that have achieved the minimum predefined set of parameter/properties required.

In accordance with the present invention, the first step in the design of optimised molecules having a particular utility is to define a set of one or more (i.e. 'n') achievement objectives. As indicated above, the set of n achievement objectives define an ideal molecule which has exactly the set of parameters desired. The number and type of achievement objectives is chosen on a case by case basis, according to the type of molecule required. By way of non-limiting example, the achievement objectives may include: activity, specificity and/or selectivity; solubility, toxicity and/or bioavailability; route of administration; polypharmacology; pharmacokinetics; synthetic accessibility; 3D or electronic shape; chemical similarity; and structural novelty. In some embodiments the method of the invention may be extended to include one or more of docking score and 3D shape similarity to a drug/lead molecule.

Once the achievement objectives have been defined, the next step is typically the generation (or selection) of an initial parent population ($P_{parent}$) of molecules from which the evolutionary design process is based. Depending on the design strategy that the user wishes to undertake, the method can operate with a variety of different libraries of chemical structure starting points. By way of non-limiting example, possible initial populations of molecules include:

(a) a single chemical structure, such as a drug or a lead compound;
(b) a single compound which is a drug or a drug lead with a known or predicted biological activity against one or more of the desired objectives;
(c) a series of chemical analogues;
(d) a series of chemical analogues which are drugs or drug leads with known or predicted biological activity against one or more of the desired objectives;
(e) a library of diverse or random compounds;
(f) a chemical structure database;
(g) a library of compounds with known activities against one or more of the desired objectives; and/or
(h) a library of compounds (diverse or analogues) where each distinct population has a known or predicted biological property against one or more of the desired objectives, but lacking known or predicted activity against the full set of desired objectives.

The method of the invention beneficially employs a database of chemical transformations, which are applied to parent populations ($P_{patent}$) of molecules in order to produce a new generation ($P_G$) of transformed molecules. There are typically a plurality of possible transformations that might be used. Suitably, all molecules of the parent population are transformed so as to generate a large library size of new molecules in the new or next generation. More suitably, all transformation are applied to each molecule of the parent population. By way of example, FIG. 1 depicts the combinatorial explosion of molecules that is achieved by generation of virtual compounds by successive rounds of chemical transformations. However, it will be appreciated that some transformations will not be possible on some molecules (e.g. required functional groups, moieties, or bonds may not be present), so that the number of molecules in the new generation generally does not equal the number of molecules in the parent population multiplied by the number of transformations. The database of transformations may also beneficially include a null-transformation so that all molecules of the parent population are also present in the new generation of molecules.

Any suitable database of chemical transformations may be used in accordance with the invention. For example, the chemical transformation database may comprise a manually curated database of chemical transformations, a database of chemical reactions or a library of genetic algorithm operators such as chemical structure mutations and crossovers. The Database can be represented in standard chemical Reaction Formats such as MDL RXN or Daylight SMIRKS.

For example, a genetic algorithm may be used to transform the molecules. A genetic algorithm may replace one atom type with another, one functional group with another, or one type of bond with another. Equally, the genetic algorithm may add or remove atoms, groups or bonds, so as to generate an enormous number of alternative molecules, rapidly, for screening. However, the genetic algorithm is generally not based on real-life experience in the art and, therefore, it may be that a significant proportion of the molecules in the mew generation are not practical molecules, for instance, it may be impossible to synthesis the molecules (or at least it may be extremely difficult to do so). A disadvantage of such a database is that unless the populations of molecules are additionally screened from a synthetic point of view in each generation, it may be that a large proportion of the processing power of the system is wasted on those impossible or impractical molecules. It may also be that the eventually selected optimised molecules cannot be synthesised.

An improvement is to use (optionally in combination with a genetic algorithm), a database of real chemical transformations, i.e. transformations that can be achieved in the laboratory.

Such a database may be generated from the knowledge and real-life experiences of medicinal and organic chemists; thus providing a resource of known chemical transformations. Another and complementary method of producing a useful database is to systematically mine the literature in the field of chemical/organic synthesis. By compiling information on chemical transformations that have been reported in publications (throughout the world), the database can be more extensive than it might be were it solely based on the recollection of scientists. Transformations based on real-life experiences are also beneficial because they can involve global changes that encompass groups of atoms rather than simply individual atoms and bonds. Hence, these transformations often require two, three or more reaction steps—as opposed to the simple atom, group or bond changes or deletions of a genetic algorithm. Although the real-life transformations may be more complex than those from a genetic algorithm, ultimately they might be more achievable and, importantly, more chemically intuitive and relevant.

Advantageously, the database of transformations is a proprietary database comprising transformations reported in the literature (e.g. written publications in fields including chemical, medicinal and organic synthesis) optionally including transformations known or identifiable by the person of skill in the art. The database may additionally include a null-transformation and/or other useful simple transformations well known to the person skilled in the art.

In one embodiment, the database of chemical transformations is created by combining input from human knowledge and an iterative systematic mining of the medical literature. Beginning with a seed set of common chemical transformation derived from human medicinal chemistry knowledge, transformations are then encoded in RXN format. Consistent sets of structure-activity-relationships (SAR) for a compound analogue series against a common target are identified. Such common sets may be best represented by a set of compounds from an individual publication (e.g. journal article or patent) as they might be the results of a coherent SAR project. To identify transformations missing from the database, it is attempted to generate computational examples of each represented analogue series in the publication by systematically applying the transformations of the existing database to each of the structures in the publication. If the existing database fails to generate any particular compound, from the selected staring compound(s), then the transformation required to generate that compound is highlighted a potentially missing from the database. The systematic application of this iterative method enables the identification of the majority of chemical transformations that have been undertaken by medicinal chemists (and reported in the literature).

Any number of transformations can be included in the database, and the more unique transformations the greater the possibilities for generating novel structures for assessment. The database should be large enough to allow a sufficient number of transformed molecules to be generated (and then assessed), in order that one or more predicted optimised molecule may be identified. For example, the database may include at least 100 real-life transformations, at least 200, at least 300, at least 400 or at least 500 transformations. Advantageously, the database may contain up to 1000 transformations or more. In one embodiment, the chemical database generated as described above includes at least approximately 432 unique transformations, in another embodiment the database includes approximately 665 transformations.

Generally, the next step in the method is to generate a population of transformed molecules ($P_{Transformed}$) by applying the transformations to the parent population of molecules. In some embodiments, all of the molecules from the preceding generation (or iteration) are included in the starting population from which a new population (or generation) of transformed molecules is generated. However, in some embodiments the preceding transformed population is filtered or otherwise screened so that the parent population to be transformed comprises only a subset of the preceding transformed population. Typically all of the available transformations in the database are applied to the parent molecules, such that a plurality of (new) transformed molecules may be derived from each molecule in the parent population. Where the database includes a null-transformation, the transformed population of molecules further includes each member of the parent population.

The population of transformed molecules ($P_{Transformed}$) is then evaluated to identify useful molecules. In some embodiments, all of the molecules of the transformed population are evaluated against one or more of the defined achievement objectives ($O_{1-x}$). It can be advantageous to evaluate the transformed population of molecules against less than the full set of achievement objectives ($O^A_{1-n}$) in order to reduce the computational power required to perform the method, and also to increase the speed of the evaluation process. This can be particularly beneficial during early rounds/iterations of the process, for example, because: it is unlikely that an optimised molecule will be achieved at an early stage in the method (enabling a more rapid sampling); or to focus/direct the method towards selecting for particular properties in particular generations (e.g. to generate a population of molecules having one desired property, such as high binding affinity, before optimising those molecules for the complete set of properties); or when the population of molecules to be evaluated is particularly large. In all cases, however, in the final generation or iteration of the process, the final population of molecules to be assessed should be evaluated against all of the n achievement objectives ($O^A_{1-n}$), to ensure that the final optimised molecules can be accurately evaluated and ranked, as required. The evaluation process includes the calculation of predicted physical parameters relevant to each of the objectives, as discussed elsewhere herein.

When it is desired to reduce a population size, the method of the invention may beneficially include one or more filters (F). The filters are generally adapted to remove unwanted/undesirable molecules so as to reduce the number of molecules in one or more generations/populations. Suitably, the filters are not random filters, but are designed to identify and remove structures that are predicted to fail specified criteria for molecules of the invention.

Advantageously, the filters are applied so as to remove the undesirable molecules (and hence, decrease the population size) prior to evaluation, thereby to reduce the burden on the computer processor, the time taken to perform the evaluation, and to improve efficiency.

The filters (F) can be defined according to any appropriate criteria for selecting (or filtering) desirable (wanted) from undesirable (unwanted) molecules. For example, one useful filter is adapted to remove duplicate molecules. Another filter may be based on the molecular properties defined by Lipinski (Lipinski, C. A. et al. (1997), *Advanced Drug Delivery Reviews*, 23, 3-25) and/or Veber (Veber, D. F. et al. (2002), *J. Med. Chem.*, 45, 2615-2623). Yet another useful filter may be based on the unwanted group definition (Brenk, R. et al. (2008), *Chem Med Chem*, 3, 435-444) and/or the reactive group definition (as encoded by the HTS component collection from Accelrys Pipeline Pilot Version 7.5). Other filters that may be used are 'drug like' molecular properties filters that are known in medicinal chemistry and drug design. Absorption, distribution, metabolism and excretion (ADME) properties can be predicted by a number of commercially available algorithms and these properties are useful for defining appropriate filters for use in the invention. In practice, an unwanted group filter can be slower to process than filters based on, for example, HTS, Lipinski and/or GSK, and so this filter may only be applied at the end of the method, e.g. under the 'end-if' condition, rather than in every iteration. In some embodiments a set of filters is applied during each iteration (or to each generation of molecules) to reduce the population size of each generation. A suitable set of filters comprises: Lipinski's Rule of Five, a total polar surface area filter, and a number of rotatable bonds filter. Typically, the duplicate molecule filter is applied in each generation/iteration of the process. Optionally the unwanted groups filter may also be applied.

Typically, the next step is to carry out an evaluation or assessment of each of the molecules or individuals (I) remaining in the population to be evaluated. The evaluation or assessment of molecules may be based on one or more selected objective ($O_{1-x}$), which in some embodiments may be the full set of n achievement objectives ($O^4_{1-n}$). As already noted, however, in some embodiments x may be less than n, such that only a select number of the achievement objectives are used for the evaluation in any particular iteration or cycle of the method.

A powerful feature of the invention is the employment of a strategy function (S) to guide the selection and evolution of molecules. By simply changing the strategy function, the invention can be applied to a diverse range of drug discovery/design applications in order to optimise molecules against diverse sets of objectives to have varied properties and applications. Apart from guiding the evolution of molecules, like the filters (F), the strategy function (S) can also be implemented to reduce the number of molecules in a population. Initially, at least one target activity (e.g. 1, 2, 3 or more) for the strategy function is selected. The target activity is used as an intermediate means of evaluating molecules of the invention and as a means for weighting or guiding the selection of optimised molecules.

Therefore, the selected target activity may usefully be based on or related to one or more of the achievement objectives. For example, the target activity may be an activity that indicates compliance with an achievement objection, such as binding affinity for a target molecule; or it may be an activity that indicates non-compliance with an achievement objective, such as binding affinity or selectivity for a non-target molecule. The predicted 'target activity' (Prediction 1) of each molecule in the evaluated population for the first target activity is calculated, along with the mean predicted target activity ([Prediction 1]Mean) over the population of evaluated molecules and the standard deviation of the predicted target activity ([Prediction 1]StdDev.

In order to find optimised molecules having good activity for a first target activity, the compounds generated in one or more iterations can be filtered using the strategy function (S) based on predicted first target activity (Prediction 1). The strategy function may be used to partition the molecules in the evaluated population between a first population ($P_{elite}$) of those that have an suitably high predicted first target activity and therefore satisfy the strategy function, and a second population ($P_{non-elite}$) of those that have a relatively low predicted first activity and therefore fail the strategy function. In one embodiment, the strategy function is:

Prediction 1>[Prediction 1]Mean+[Prediction 1]StdDev

Thus, a molecule satisfies the strategy function if its predicted first target activity of higher than the mean predicted first target activity plus the standard deviation of the predicted first target activity; otherwise a molecule falls the strategy function.

One or more predicted target activities (Prediction 1 to n) may be used in one or more strategy functions in order to direct the evolution and selection of useful molecules. Where two predicted target activities are defined, the strategy function may take the form:

Prediction 1>[Prediction 1]Mean+[Prediction 1]StdDev
and
Prediction 2>[Prediction 2]Mean+[Prediction 2]StdDev By way of example, to optimise a molecule into a useful pharmaceutical drug against a defined target molecule, the first target activity may be predicted binding activity against the target molecule (Prediction 1); and the second target activity may be predicted ADME score (Prediction 2). The above strategy function can then be used to optimise each generation of molecules towards an increase in both first and second target activities.

In another embodiment, to identify an optimised molecule where the objective is to increase the activity against a first target molecule (i.e. Prediction 1) but to improve selectivity over a second target molecule (i.e. Prediction 2), the following strategy function may be employed:

Prediction 1>[Prediction 1]Mean+[Prediction 1]StdDev
Selectivity=Prediction 1−Prediction 2

The evaluated molecules are then ranked in descending order according to selectivity and the first N molecules identified as satisfying the strategy function.

In another embodiment it may be desirable to evolve a molecule having optimised polypharmacology against two or more (N) defined target molecules. The predicted target activities are then Prediction 1 to Prediction N, and a suitable strategy function may be:

Prediction 1>[Prediction 1]Mean+[Prediction 1]StdDev
. . . and . . .
Prediction N>[Prediction N]Mean+[Prediction N]StdDev Molecules can be further selected and ranked according to their polypharmacology using the function:

Polypharmacology=Product of Predictions 1 to N

Molecules may then be ranked in descending order of polypharmacology score and the first N molecules selected as satisfying the strategy function.

The above are non-limiting examples of possible strategy functions (S) for use in accordance with the methods of the invention. The person of skill in the art can readily devise alternative strategy functions (S) according to system requirements. In an alternative aspect of the invention, an achievement objective need not be predefined by the user, but may instead be defined by the system, for example, at the end of a predefined number of iterations, or after a predefined period of time (as previously described). In this aspect, the system may itself determine an achievement objective having regard to the predicted properties of randomly evolved molecules. For instance, the objective may be determined following an analysis of the predicted activities of the final population of molecules across a wide profile of activity models, thereby selecting an objective for which predicted useful molecules have randomly evolved. In practice, the method may involve analysing an initial population of one or more molecule against the available models of parameter prediction (e.g. all available Bayesian models), and then generating one or more subsequent populations of transformants with no predefined strategy or achievement objective(s) to guide those iterations. After a predetermined number of iterations, the resultant population of molecules may then be assessed against one or more, and conveniently all available models for parameter prediction (e.g. Bayesian model) at the disposal of the system. In this regard, the methods of the invention can assess Bayesian models for at least 1000 targets. Furthermore, the method of the invention may then select the 'Achievement Objective' for which there is demonstrated the greatest improvement between the initial population and $n^{th}$ generation. Alternatively, the objective may be defined according to the most interesting parameter profile determined, e.g. as judged by reference to a predefined list of medically/therapeutically important molecular target profiles. Thereafter, the method of this aspect of the invention may finish, or alternatively that profile may be selected as the Achievement Objective and the Strategy function for the calculation and selection of one or more further iterations.

As indicated above, the strategy function may be used to select a particular advantageous sub-group of the existing molecules to take through to the next iteration. For example, it may be used to identify the molecules in a population that meet one or more specified and predefined predicted target activities. As a consequence, the strategy function may also be used to reduce the number of molecules taken through to the next iteration, by removing the molecules having the least potential for satisfying the achievement objectives. Having evaluated the molecules of the invention and applied a strategy function, the sub-population ($P_{elite}$) of molecules that satisfies the function and the sub-population ($P_{non-elite}$) that falls the strategy function are identified. The molecules taken through to the next round or iteration of the method ($P_{select}$) can then be selected in any suitable manner. In one embodiment, only the members of $P_{elite}$ are selected for the next round of the evolution process. In another embodiment, a sample of molecules (i.e. a further sub-population) of the population $P_{non-elite}$ are also selected for the next iteration and combined with the population $P_{elite}$. Advantageously, the sub-population of molecules from the population $P_{non-elite}$ is selected at random ($P_{random}$). Accordingly, in a preferred embodiment the population of molecules taken into the next iteration of transformation and evaluation ($P_{select}$) is $P_{elite}+P_{random}$. By applying a strategy function, the approach has the advantage of identifying and focussing the evolutionary strategy on those molecules having the greatest potential for reaching the achievement objectives. Furthermore, including a sub-population of molecules that fail the strategy function (particularly a random population), serves to increase the variability in the genetic pool of molecules retained in the evolution process, and has thus been found to enhance the potential for generating new molecules having optimised parameters for the relevant achievement objectives. In this regard, simply because a particular molecule does not satisfy a strategy function does not mean that a corresponding transformed molecule will not satisfy the strategy function and ultimately lead to an optimised combination of physical parameters.

Having selected the population of molecules for further assessment ($P_{select}$), the relevant parameters for each member (or individual, $I_1$-$I_n$) in the population ($P_{select}$-$P_{G+1}$) are calculated or predicted for each of the selected Objectives ($O_{1-x}$). Each member of the population can then be evaluated against the objectives ($O_{1-x}$)—or more suitably against all n of the Achievement Objectives ($O^A_{1-n}$)—to determine whether or not the current population of molecules ($P_{G+1}$) fulfils the predetermined requirements of the selected objectives or the Acheivement Objectives. Once a population ($P_{G+1}$) of molecules is found to include either: an optimised molecule; a predetermined number of optimised molecules; or a predetermined proportion of optimised molecules, the 'Stop condition' is met and a final evaluation and ranking phase is initiated. Thus, the Stop condition can be defined to suit the requirements of the system for identifying a single optimised molecule or a group of molecules. However, if the Stop condition is not met, then the population of molecules ($P_{G+1}$) is taken through a further iteration of transformation and evaluation.

To evaluate molecules, the invention uses one or more methods for predicting biological activity of a chemical structure/molecule, for example: one-dimensional (1 D) Bayesian SEA, two-dimensional (2D) similarity, and/or three-dimensional (3D) docking. The method may in addition or alternatively evaluate molecules according to one or more methods for predicting drug-like and ADMET properties. Any suitable predictive activity and/or ADME models may be used in accordance with the invention.

By way of example, the method may use any algorithm known in the art to calculate, score or predict a defined biological, chemical or pharmacological activity for a specified target, assay or protein structure. Methods such as Bayesian activity modelling (e.g. Nidhi et al., (2006), Prediction of biological targets for compounds using multiple-category Bayesian models trained on chemogenomics databases, *J. Chem. Info. Modeling,* 46, 1124-1133; and Paolini et al., (2006), Global mapping of Pharmacological Space, *Nature Biotech.* 24(7), 805-815); or other chemical ligand similarity methods, such as the Similarity Ensemble Approach (SEA) (Kaiser et al., (2007), Relating protein pharmacology by ligand chemistry, 25(2), 197-206); or 3D docking methods (e.g. FlexX, GOLD, DOCK, AutoDOCK, and GLIDE) may be used. In a beneficial embodiment of the invention, Bayesian activity modelling (implemented in Pipeline Pilot version 7.5, as described by Nidhi et al., and Paolini et al.) is employed to predict the molecular target activity or specificity and/or biological assay activities of molecules.

Similarly, the system can use any available algorithm to calculate, score and/or predict a potential ADME score and/or 'drug-like' properties. Particularly suitable examples that may be used to calculate relevant properties of the molecules include: Optibrium's Stardrop; Accelrys Pipeline Pilot ADME Component collections; desirability functions; ADMET Rules of Thumb (Gleeson (2008), *J. Med. Chem.,* 51(4), 817-834); and/or toxicity rules (Pfizer, (2008) *Bioorg. Med. Chem. Letters,* 18, 4872-4875). However, the invention is not limited to these specific programs; other programs that calculate properties such as an ADME score or a predicted biological activity (SEA) can also be used in accordance with the invention. In a particularly suitable embodiment of the present invention the ADME scoring function used is Optibrium's Stardrop.

Optionally, additional information may also be included to help in analysing structures and obtaining useful predictions of relevant chemical properties. For example, structure-activity relationship information relating chemical structures to actual biological activity derived from published literature, experimental screening data or virtual screening information may be employed. Chemical Knowledge obtained in this way may then be encoded as rules or probablistic filers, such as Lipinski's Rule of Five, Gleeson's ADMET Rules of Thumb, Pfizer's toxicity probabilities, Leeson's lipophilicity, Hopkins's ligand efficiency, Shoichet's aggregation, and Pipeline Pilot ADMET guidelines. Alternatively, specific rules derived for a particular project, such as the need for CNS penetration, the specific requirement for a 'pro-drug' structure moiety etc. can be encoded.

Having evaluated the molecules of the invention using predictive algorithms (as above) against the predefined target objectives or the full set of achievement objectives, it is beneficial to measure the predicted performance of each molecule against the objectives and/or to be able to rank each molecule relative to the others in the evaluated population.

Figure 2:
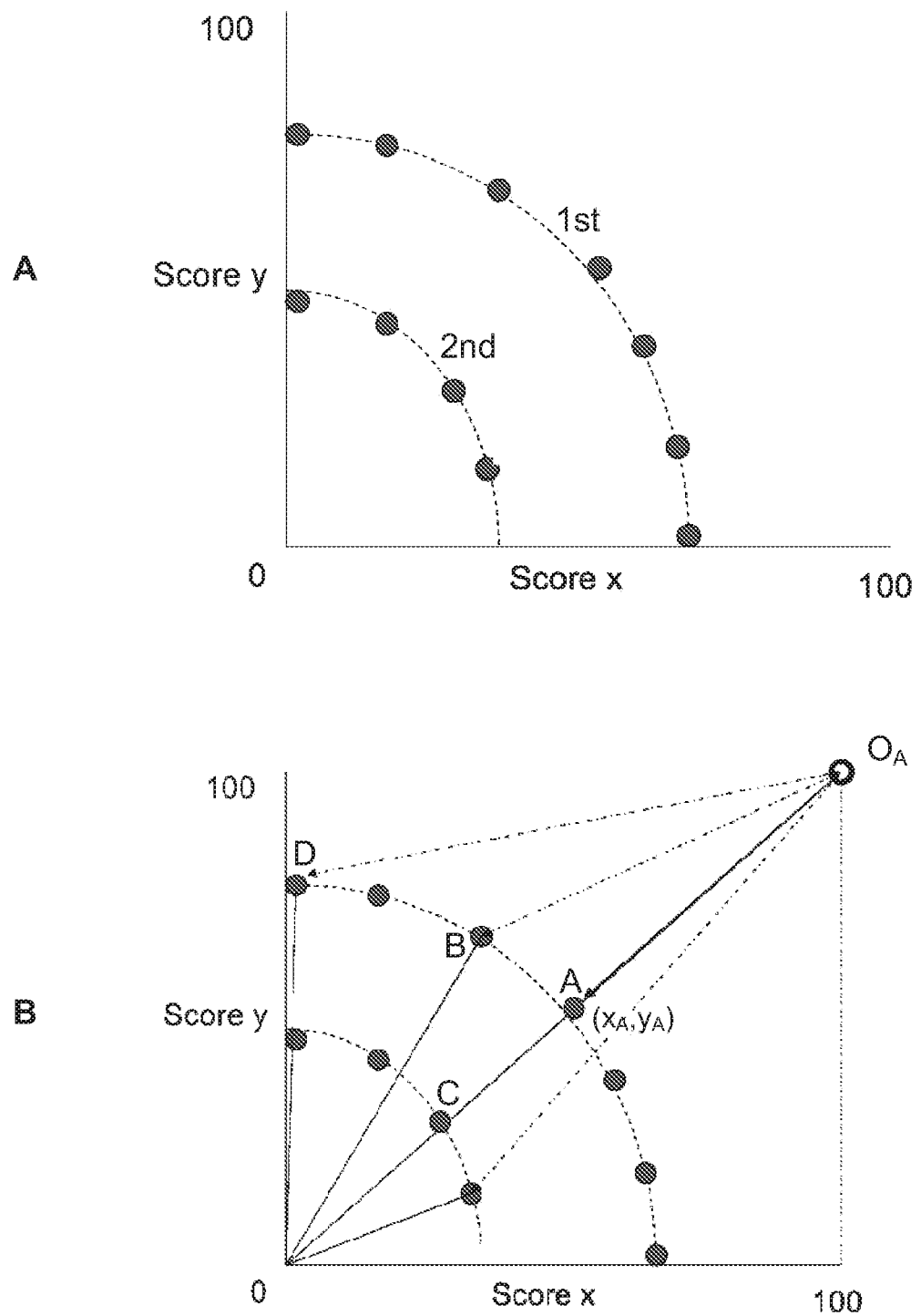
FIG. 2 illustrates how virtual molecules may be arranged according to Pareto frontier ranking relative to a set of two achievement objectives, score x, score y (A); and how virtual molecules may be assessed and ranked according to vector distance and Pareto ranking from the achievement objectives showing how molecules on a lower Pareto frontier may be closer to the achievement objectives than molecules on a higher Pareto frontier (B)

One way of evaluating a population of molecules against a target objective is to use Pareto frontier ranking. A Pareto algorithm may be used to identify non-dominated points in a population. Following identification of the first Pareto frontier, the subsequent frontiers (e.g. second, third and fourth) may be identified and the individuals in the population can be scored accordingly (FIG. 2A). A convenient system for assigning Pareto ranking is implemented in Accelrys Pipeline Pilot.

While Pareto ranking may be used to identify non-dominated members in a population, it cannot prioritise solutions on the same frontier, or prioritise the entire population relative to a defined set of objectives. Accordingly, Pareto ranking prioritises molecules (by frontier) according to a selected individual parameter, thereby identifying possible groups of molecules; but it does not take into consideration other parameters and factors that can influence the overall performance of a molecule. Since, Pareto ranking does not provide any comparison of molecules within and between frontiers or take account of other parameters of the molecules, the frontier ranking itself does not generally reflect the actual proximity of each molecule to the defined achievement point. Hence, systems such as those based solely on Pareto frontier ranking, are biased towards selecting molecules that have one advantageous property at the expense of other important properties (e.g. ADMET score), and this means that far greater post-design evaluation (e.g. expensive, labour and time consuming laboratory assessment work) is required to identify useful molecules that have the desired characteristics. For these reasons, such methods and systems cannot truly identify optimised molecules.

In contrast, a goal-type criterion can readily be employed when a linear distance from a given target value (which can be changed between the interactions) is to be minimised. Thus, a particular advantage of the invention is that it employs a vector distance (VD) evaluation of molecules to a defined achievement point, in order to prioritise compounds against a desired objective or set of objectives. The use of vector distance evaluation of molecules to a achievement or target point is beneficial because, amongst other things, it provides a simple linear measure of the distance between each molecule and the achievement point, and it can equally take into consideration other relevant parameters of the evaluated molecules. In this way, the vector distance measurement provides a clear, unambiguous measurement that reflects the actual proximity of a molecule to the achievement objectives. Vector distance optimisation can be used by defining an achievement scalarising function (ASF), for example, as demonstrated below.

In addition to vector distance measurement, the invention my further comprise Pareto frontier ranking (FIG. 2B). In this regard, by further evaluating molecules according to Pareto frontier, the method of the invention is able to use vector distance to prioritise and compare compounds within the same and different Pareto frontier against the one or more achievement objectives, thereby prioritising molecules from the entire population, if desired. Accordingly, in a preferred embodiment of the invention, molecules from each generation are evaluated by Pareto ranking and vector distance (VD) to the various predicted and calculated parameters (such as predicted biological activity and ADMET properties), in order to identify optimised molecules.

Furthermore, the combined use of Pareto ranking and vector distance during the evolutionary process enables the prioritisation and selection of molecules having different Pareto rankings, which may allow for the blending of unpredictable but ultimately beneficial properties and activities, and/or may also allow molecules from a lower Pareto frontier to be selected ahead of less useful molecules (overall) from a higher Pareto frontier. As shown in FIG. 2B, the highest ranking molecule A ($x_A, y_A$) in the population can be readily identified by its linear proximity to the achievement point $O_A$. Compound C on the second Pareto frontier is closer by vector distance to the achievement point than compound D on the first Pareto frontier, and may be prioritised ahead of compound D, to provide useful molecular properties that might otherwise be missed. Accordingly, in some embodiments the invention prioritises molecules within the same Pareto frontier according to vector distance from the target objective; and in other embodiments, the invention prioritises molecules from different Pareto frontiers (e.g. from first, second and third frontiers) according to vector distance from the target objective. In the final iteration of the method, i.e. when the stop condition has been satisfied, it may be particularly advantageous to prioritise the highest ranking molecules (by vector distance) from more than one Pareto frontier (e.g. from first and second, first to third, or first to fourth frontiers) to ensure that the best overall molecules are selected. By way of example, the molecules closest to the achievement point by vector distance may be selected irrespective of their Pareto ranking. In other cases, the selection may be deliberately biased towards the first Pareto frontier: for instance, of the molecules selected at least the first 50% may be taken from the first Pareto frontier and the remainder selected irrespective of frontier ranking.

Figure 3:
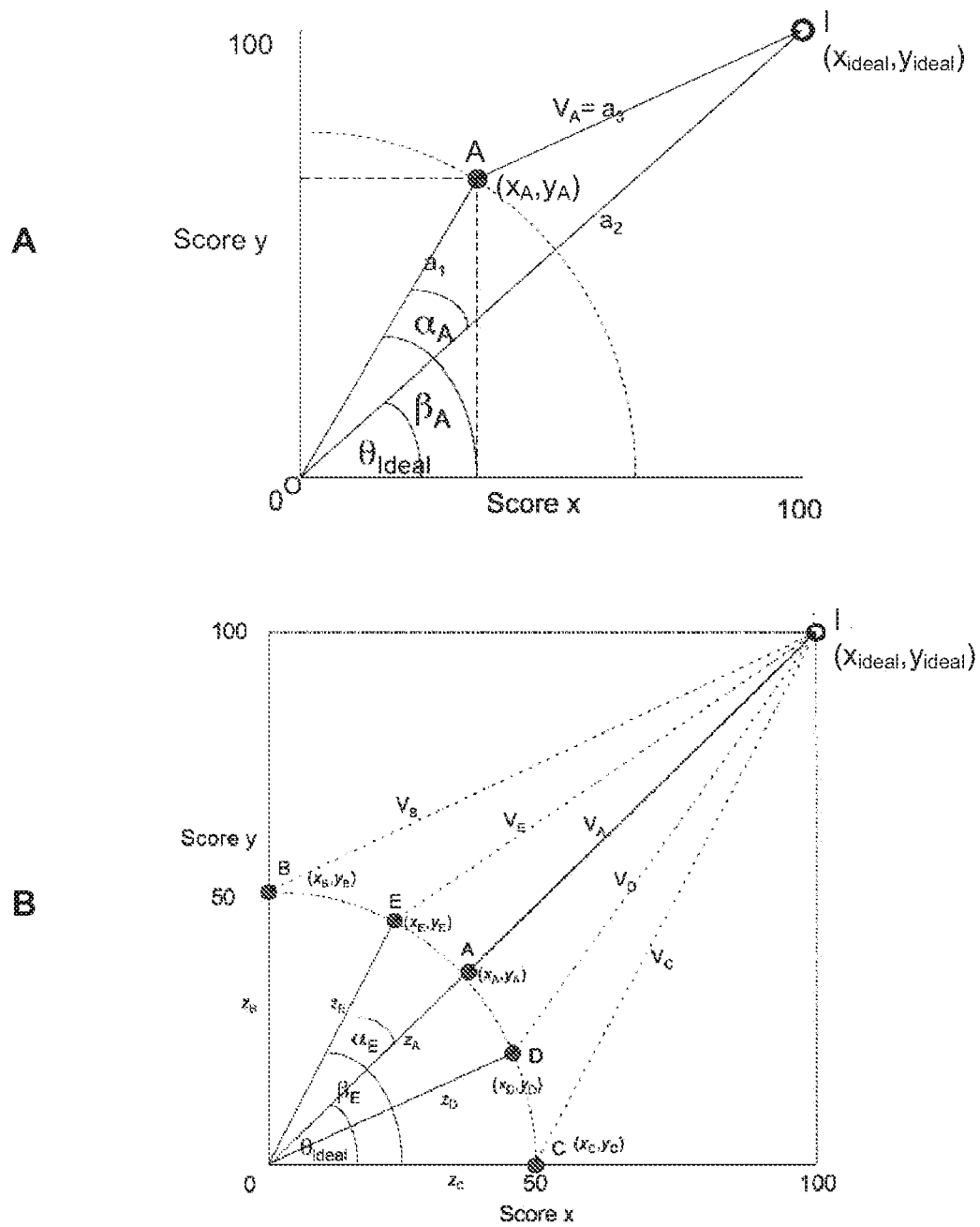
FIG. 3 illustrates how in accordance with the invention, vector distance from virtual compounds to an ideal molecule defined by the parameters of the achievement objectives ($x_{ideal}$, $y_{ideal}$) may be calculated (A); and the analysis and ranking of different molecules on a Pareto frontier (B)

Vector distance to the achievement objective (or point) may be calculated using any suitable system or algorithm, for example, using trigonometry or vector notations. With reference to FIG. 3A, in trigonometry notation, an ideal point I (with coordinates $x_{ideal}$, $y_{ideal}$—i.e. where there are two objective coordinates), can be defined as the achievement scalarising function. $V_A$ is the vector distance (V) from the ideal point to molecule A (with coordinates $x_A$, $y_A$). Then:

$$V_A = \sqrt{((x_A^2 + y_A^2) + (x_{ideal}^2 + y_{ideal}^2) - 2(\sqrt{(x_A^2 + y_A^2)})(\sqrt{(x_{ideal}^2 + y_{ideal}^2)})\cos \alpha_A)}$$

Where: $\alpha_A = \beta_A - \theta$
$z_A = \sqrt{(x_A^2 + y_A^2)}$
$\cos \beta_A = \sqrt{(x_A^2 + z_A^2 - y_A^2)/2x_A z_A}$
$z_{ideal} = \sqrt{(x_{ideal}^2 + y_{ideal}^2)}$
$\cos \theta = \sqrt{(x_{ideal}^2 + z_{ideal}^2 - y_{ideal}^2)/2x_{ideal} z_{ideal}}$ In vector notation, $V_A$ is the vector distance (V) from the ideal point I (with coordinates $x_{ideal}$, $y_{ideal}$, $z_{ideal}$—i.e. where there are 3 objective coordinates), to molecule A (with coordinates $x_A$, $y_A$, $z_A$), is equal to the modulus of the vector AI.

Then:

$$V_A = \sqrt{((x_{ideal} - x_A)^2 + (y_{ideal} - y_A)^2 + (z_{ideal} - z_A)^2)}$$

Where there are more than 3 objective coordinates in the achievement point the vector distance calculation can be generalised as:

$$V_A = \sqrt{\sum_{p=1}^{n} (x_I^p - x_A^p)^2}$$

where the ideal point has the coordinates $(x_I^1, \ldots, x_I^n)$, and molecule A the coordinates $(x_A^1, \ldots, x_A^n)$.

The vector distance can be calculated for any molecules of interest to the achievement point defined by the ideal molecule (see FIG. 3B). Table 1 below illustrates how the above calculations may be used to determine the proximity of molecules (e.g. molecules A to E) to the ideal molecule (I), and thus identify one or more optimised molecules. In this example, the ranked molecules lie on the same Pareto frontier, and molecule A is found to be the closest (most optimal) molecule to the ideal molecule and, hence, most closely satisfies the achievement objectives.

TABLE 1 trigonometric measurements of molecules on the same Pareto frontier.

|   | V | x | y | α | β | $\theta_{ideal}$ | z | $z_{ideal}$ |
|---|---|---|---|---|---|---|---|---|
| A | 91.42 | 35.36 | 35.36 | 0 | 45 | 45 | 50 | 141.421 |
| B | 111.8 | 0 | 50 | 45 | 90 | 45 | 50 | 141.421 |
| C | 111.8 | 50 | 0 | -45 | 0 | 45 | 50 | 141.421 |
| D | 95.97 | 45.32 | 21.13 | -20 | 25 | 45 | 50 | 141.421 |
| E | 95.97 | 21.13 | 45.32 | 20 | 65 | 45 | 50 | 141.421 |

In some embodiments of the Invention, the Stop condition is satisfied after a predefined number of iterations/generations of population generation, transformation and evaluation (e.g. 3, 4, 5 or more iterations). In other embodiments, however, the evaluation can be used to determine when the Stop condition is met. For example, the Stop condition can be defined as a maximum distance of one or more molecules to the one or more achievement objectives ($O_{1-x}$), or to the full set of achievement objectives ($O^A_{1-n}$). In other words, the Stop condition may be satisfied once a molecule is identified as having a vector distance of less than a predetermined number to the target. The maximum vector distance before the Stop condition is met may be chosen according to the number and/or type of the achievement objectives or accordingly to the strategy or application concerned. For example, the maximum vector distance may be approximately 110, 100, 95, 90, 80, 70, 60 or 50 from the ideal molecule. In still other embodiments, the Stop condition may be activated once a predetermined number of molecules (e.g. at least approximately 3, 5, 10, 20, 50, or 100), have reached or surpassed the predetermined maximum vector distance from the achievement objectives.

Once the Stop condition has been met, it is important to rank the molecules of the population according to each molecule's vector distance to the full set n of achievement objectives ($O^A_{1-n}$). To rank the final population of molecules, the predicted parameters of each individual member ($I_1$-$I_n$) in the population is calculated for each (1-n) of the predefined achievement objectives ($O^A_{1-n}$). This then allows the vector distance and optionally the Pareto rank for each individual in the final population to be calculated to the complete set of n achievement objectives ($O^A_{1-n}$), as described above.

Optionally, before and/or after the evaluation of vector distance and/or Pareto ranking, one or more filters (F) may be applied. The filters are conveniently used, as already explained, to remove undesirable molecules from the population, thereby helping to focus the method on those molecules perceived to be most useful, reducing the number of molecules to be further considered and, hence, reducing the computer processing demand of the system.

Finally, the molecules remaining in the final population may be prioritised, according to predefined criteria, to identify or select optimised molecules. Typically, each Individual in the population is prioritised according to vector distance to the combined set of achievement objectives ($O^A_{1-n}$). Once the molecules have been prioritised or ranked (e.g. $1^{st}$ to $100^{th}$), the first n molecules may be defined as optimised molecules and selected—possibly for further analysis (e.g. for synthesis and biological/chemical and/or pharmaceutical evaluation. 1 2, 5, 10, 20, 50, 100 or more molecules may be defined as optimised molecules and selected for such further analysis.

In some embodiments, the method of the invention encompasses all of the above features so as to enable the design of optimised drugs in an automated process.

The evolutionary algorithm of the invention may comprise the following steps:
1.0 Start
   1.1 Define Achievement Objective ($O^A_{1-n}$)
   1.2 Generation G=0
   1.3 Selection of Initial Population of molecules $P_{G=0}=(I_1-I_n)$
   1.4 $P_{G=0}=P_{Parent}$
   1.5 Calculate parameters for each Individual ($I_1$-$I_n$) for each of the selected Objectives ($O_{1-x}$)
   1.6 Calculate Vector Distance and Pareto Rank to Achievement Objectives ($O^A_{1-n}$) for each Individual in the Population
2.0 If Stop condition is not satisfied
   2.1 Generate new Population ($P_{Transformed}$) by applying all Transformations (T) to all members of the Population ($P_{Parent}$)
   2.2 Remove all members that fail defined Filters (F)
   2.3 $P_G = P_{Parent} + P_{Transformed}$
   2.4 Remove all duplicates to produce a Population ($P_G$) of unique members
   2.5 Calculate parameters for each Individual (I) of $P_G$ for each of the selected Objectives ($O_{1-x}$)
   2.6 Select Individuals with calculated Objective parameters that satisfy the Strategy rule (S) into Elitist Population ($P_{Elite}$)
   2.7 Select members with predicted parameters that fail the Strategy rule (S) into Non-Elitist Population ($P_{Non-Elite}$)
   2.8 Selective N random members of $P_{Non-Elite}$ to form a Random Population ($P_{random}$)
   2.9 Merge $P_{Elite} + P_{random}$ to create a new population $P_{select}$ 2.10 $P_{G+1}=P_{select}$
2.11 Calculate parameters for each Individual ($I_1$-$I_n$) in $P_{G+1}$ for each of the selected Objectives ($O_{1-x}$)
2.12 Evaluate Vector Distance and Pareto Rank to the Objectives ($O_{1-x}$) for each individual in $P_{G+1}$
2.13 $P_{parent}=P_{G+1}$
2.14 Generation G=G+1
3.0 End If
3.1 Calculate parameters for each Individual ($I_1$-$I_n$) for each of the Achievement Objectives ($O^4_{1-n}$)
3.2 Calculate Vector Distance and Pareto Rank to the Achievement Objective ($O^4_{1-n}$) for each Individual in the final population
3.3 Apply Filters (F)
3.4 Prioritise each Individual by Vector Distance to Achievement Objectives ($O^4_{1-n}$)
In an alternative embodiment, in one or more iterations, the calculations and evaluations in steps 2.11 and 2.12 above are based on the full set of n Achievement Objectives ($O^4_{1-n}$).

Having identified optimised molecules for potential use in the desired applications, the method may optionally further include assessing the prioritised compounds for novelty against databases of known molecules (e.g. using a chemical structure similarity), and/or assessing the synthetic accessibility of prioritised molecules (e.g. by passing the resultant molecular structures through a retrosynthetic scoring system such as CEASAR). In this way, the method can be still further directed towards the selection of useful and desirable molecules.

Figure 4:
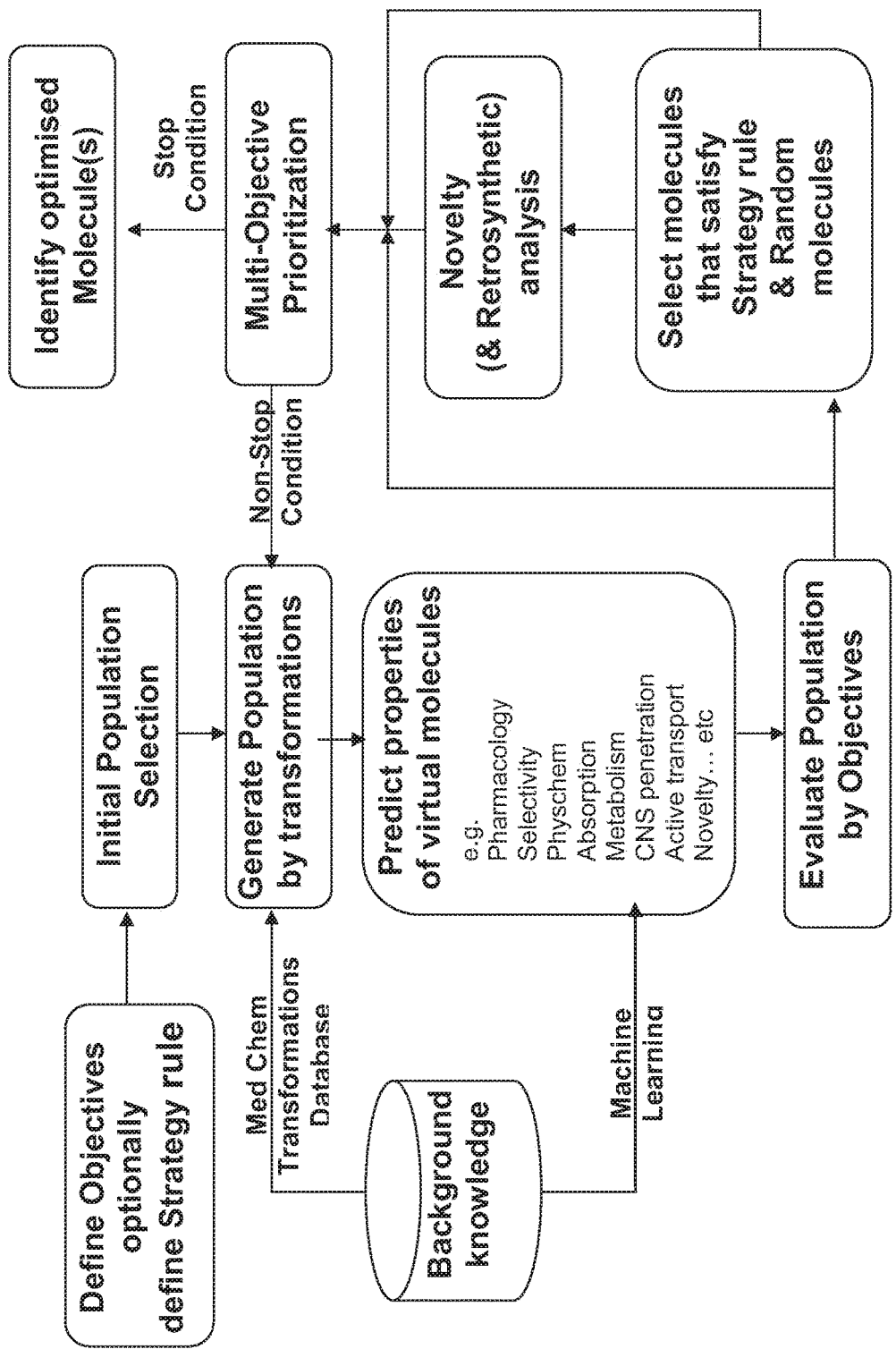
FIG. 4 is a flow diagram illustrating the steps in a general method of the invention.

Thus, a general way of carrying out the invention can be illustrated with reference to FIG. 4. First, the achievement objectives and optional strategy rule are defined. The initial population of molecules for evolution and evaluation is selected. Background knowledge is used to generate a database of chemical transformations for producing virtual transformed molecules. Background knowledge may also be used for the assessment and prediction of molecular and activity properties. A first generation of transformed molecules is produced by applying a set of molecular transformations to the initial population of molecules. In the next step one or more properties of each virtual molecule are predicted and the population of molecules is then evaluated against the predefined achievement objectives. Optionally, the strategy rule is applied to the evaluated molecules and the molecules that satisfy the strategy rule are selected for later prioritisation along with one or more randomly selected members of the population that failed the strategy rule. A novelty and retrosynthetic analysis of the selected population may be performed to analyse the structures that have been selected. Finally in this iteration of the method, the remaining molecules are prioritised against the achievement objectives. If the stop condition is not satisfied, the method takes the non-stop condition route and a further population of transformants is produced.

In summary, the method of the invention beneficially comprises one or more of the following aspects:
(a) a library or database of chemical transformations (e.g. stored as chemical reactions, such as in RXN or SMIRKS format);
(b) a method for applying chemical transformations to a chemical structure to produce a new chemical structure (e.g. methods such as RXN and SMIRKS);
(c) one or more methods for predicting biological activity of chemical structures (e.g. 1D Bayesian SEA, 2D similarity, 3D docking);
(d) one or more method for predicting drug-like and ADMET properties (e.g. Optibrium's Stardrop or Accelrys Pipeline Pilot ADME Collection of algorithms);
(e) a method for closed loop iteration for the successive generation of novel compounds by applying a library of chemical transformations to each member of the parent population of chemical structures;
(f) a strategy function definition for the selection of members of each iterative generation;
(g) a method for ranking and prioritising chemical structures against a desired set of objectives, (e.g. using a combination of Pareto ranking and vector distance measurement).

These and other beneficial features provide increased flexibility and utility to the method of the invention, for example: it can be applied to successfully operate with a single input compound (such a known drug or lead compound), or an entire database of compounds; the input structures are not limited by molecular mass (i.e. not only small molecules or fragments); and the strategy function enables the algorithm to be easily directed towards a wide range of drug discovery approaches. Non-limiting examples of applications for the potential drug discovery strategies and approaches, of the invention include:

(1) Cost reduction in getting a dug to clinical trials and/or to market: by identifying and optimising (by iterative rounds of in silico molecular evolution and selection), small molecule drug-like compounds and thereby reducing the number of compounds that must be synthesised in order to optimise a project from a lead to a candidate drug.

(2) Expediting the process of alternative drug identification: novel compounds with superior pharmacological profiles to existing on-the-market pharmaceutical agents can be identified and optimised.

(3) Multi-target drug design/design of compounds with polypharmacology: by identifying and optimising (by iterative rounds of in silico evolution and selection), small molecule drug-like compounds that may be active against more than one drug target.

(4) Lead identification: for a series of chemical analogues the drug-likeness and the potential of molecules for optimisation can be explored in silico before experimental testing to improve efficiency and eliminate compounds having a low probability of success.

(5) Selective optimisation of a side, weak or off-target activity of a known drug into a new primary activity (e.g. SOSA).

Dosage Forms, Medicaments and Pharmaceuticals

In accordance with the invention, the compounds and molecules may be manufactured into medicaments or may be formulated into pharmaceutical compositions. When administered to a subject, an agent, including inhibitors, of the invention is suitably administered as a component of a composition that comprises a pharmaceutically acceptable vehicle. The molecules, compounds and compositions of the invention may be administered by any convenient route, for example, methods of administration include intradermal, intramuscular, intraperitoneal, intravenous, subcutaneous, intranasal, epidural, oral, sublingual, intranasal, intravaginal, transdermal, rectally, by inhalation, or topically, to the skin. Administration can be systemic or local. Delivery systems that are known also include, for example, encapsulation in liposomes, microparticles, microcapsules, capsules, etc., and can be used to administer the compounds of the invention. Any other suitable delivery systems known in the art is also envisioned in use of the present invention. The mode of administration may be left to the discretion of the practitioner.

Acceptable pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and colouring agents may be used. When administered to a subject, the pharmaceutically acceptable vehicles are preferably sterile. Water is a suitable vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The medicaments and pharmaceutical compositions of the invention can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical vehicles are described in Remington's Pharmaceutical Sciences, Alfonso R. Gennaro ed., Mack Publishing Co. Easton, Pa., 19th ed., 1995, see for example pages 1447-1676.

Suitably, the compounds of the invention are formulated in accordance with routine procedures as a pharmaceutical composition adapted for oral administration (more suitably for human beings). Compositions for oral delivery may be in the form of tablets, lozenges, aqueous or oily suspensions, granules, powders, emulsions, capsules, syrups, or elixirs, for example. Thus, in one embodiment, the pharmaceutically acceptable vehicle is a capsule, tablet or pill. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. When the composition is in the form of a tablet or pill, the compositions may be coated to delay disintegration and absorption in the gastrointestinal tract, so as to provide a sustained release of active agent over an extended period of time. Selectively permeable membranes surrounding an osmotically active driving compound are also suitable for orally administered compositions. In these dosage forms, fluid from the environment surrounding the capsule is imbibed by the driving compound, which swells to displace the agent or agent composition through an aperture. These dosage forms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. Typically, compositions for intravenous administration comprise sterile isotonic aqueous buffer. Where necessary, the compositions may also include a solubilising agent.

Where the invention provides more than one active agent for use in combination, generally, the agents may be formulated separately or in a single dosage form, depending on the prescribed most suitable administration regime for each of the agents concerned.

The molecules and pharmaceutical compositions of the invention may be formulated and suitable for administration to the central nervous system (CNS) and/or for crossing the blood-brain barrier (BBB).

Figure 15:
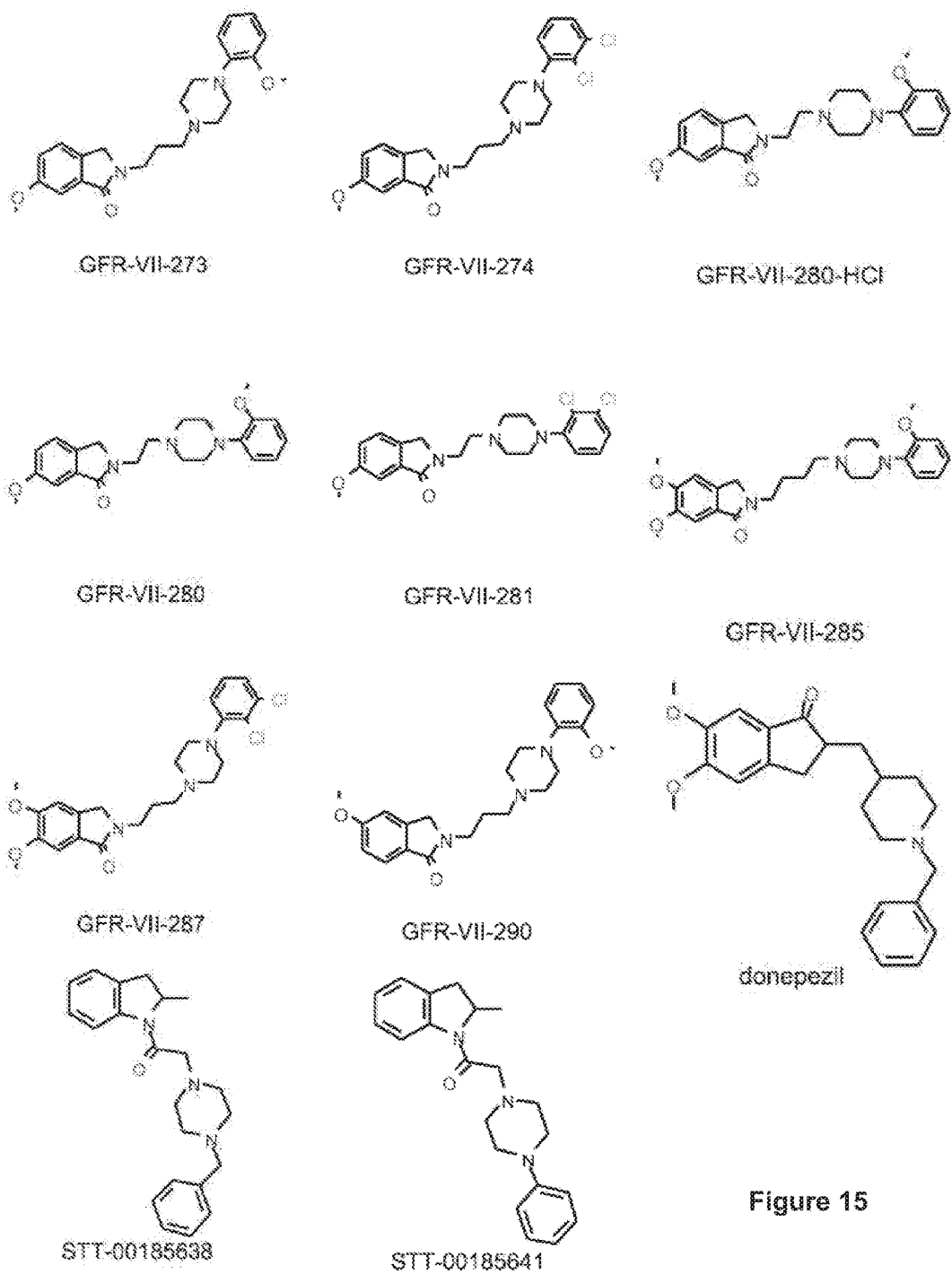
FIG. 15 illustrates the structures of compounds of the invention selected as having predicted activity for binding to and antagonising the dopamine D2 and dopamine D4 receptors, including: donepezil (starting molecule), the isoindolinones series evolved as dopamine D2 ligands: GFR-VII-273, GFR-VII-274, GFR-VII-280, GFR-VII-281, GFR-VII-285, GFR-VII-287, GFR-VII-290; and the 2,3-dihydro-indol-1-yl series evolved as dopamine D4 ligands: STT-00185638 and STT-00185641.

Selected molecules according to the invention are shown in FIG. 15.

Diseases and Conditions

The molecules, compounds, therapeutic agents and pharmaceutical compositions of the invention may be evolved, selected and optimised to have activity against any desired target molecule. Typically, the target molecule is a protein or peptide. The target molecule may be a wild-type or a mutated protein or peptide, such as may be associated with a disease or condition. Beneficially, the disease or condition is in a mammal, and more suitably in a human subject.

The molecule or pharmaceutical may be suitable for single target therapy or for polypharmacology. Antagonists of dopamine D2 and/or dopamine D4 identified in accordance with the invention may be useful in the treatment of diseases and conditions such as schizophrenia, Parkinson disease and/or myoclonus dystonia.

The method of the invention is particularly beneficial in evolving and optimising molecules having beneficial polypharmacology. By way of example, suitable polypharmacology (multi-target) protein combinations against which molecules of the invention can be optimised include: (1) phosphodiesterase 5 and endothelin A receptor; phosphodiesterase 5 and endothelin B receptor; and phosphodiesterase 5, endothelin A receptor and endothelin B receptor. A molecule that inhibits phosphodiesterase 5 and antagonises one or both of endothelin A receptor and endothelin B receptor may be suitable for the treatment of pulmonary hypertension; (2) an inhibitor of IKK2 and COX2 may be useful in treating cancer; (3) and inhibitor of p38 alpha MAP kinase and COX2 may be useful in the reduction and treatment of pain; (4) a combination of a 5HT1A receptor agonist and a dopamine D2 receptor antagonist may be useful as an antipsychotic drug; (5) 5HT1A receptor and NERT; 5HT1A receptor and SERT; 5HT1A receptor and NERT and SERT; 5HT1A receptor and Dopamine D3 receptor; 5HT1A receptor and Dopamine D4 receptor; and 5HT1A receptor and alpha 2A receptor. An antagonist of the 5HT1A receptor and/or the Dopamine D3 receptor and/or the Dopamine D4 receptor and/the alpha 2A receptor optionally in combination with an inhibitor of NERT and/or SERT may be useful as an antidepressive medicament; (6) Dopamine D3 receptor and Dopamine D4 receptor; acetylcholinesterase and Dopamine D3 receptor; and acetylcholinesterase and Dopamine D4 receptor. An antagonist of the Dopamine D3 receptor and/or the dopamine D4 receptor optionally in combination with an inhibitor of acetylcholinesterase may be useful in cognition enhancement.

Alternatively, the method of the invention may be used to optimise molecules to have the required activity against one or more of the above target molecules. In this case, the invention encompasses suitable combinations of the molecules of the invention to treat any of the above diseases or conditions. Further, the use of a molecule or pharmaceutical of the invention in the simultaneous, separate or sequential treatment of one of the above diseases or conditions is also envisaged.

The invention will now be described by way of the following non-limiting examples.

EXAMPLES

Unless otherwise defined, all technical and scientific terms used herein have the same meaning as commonly understood by one of ordinary skill in the art to which this invention belongs. Where common molecular biology techniques are described it is expected that a person of skill in the art would have knowledge of such techniques, for example from standard texts such as Sambrook J. et al., (2001) *Molecular Cloning: a Laboratory Manual*, Cold Spring Harbor Press, Cold Spring Harbor, N.Y.

Unless otherwise specified, the practice of the present invention will employs conventional techniques in medicine, pharmacology and biochemistry, which are within the capabilities of a person of ordinary skill in the art.

Example 1

Optimisation of Tadalafil from Lead Compound

This example demonstrates the optimisation and selection of a new drug from a lead compound: specifically, the design, selection and optimisation of the approved drug tadalafil from its lead compound.

Tadalafil, chemical name (6R,12aR)-6-(1,3-Benzodioxol-5-yl)-2-methyl-2,3,6,7,12,12a-hexa hydropyrazino[1',2':1,6]pyrido[3,4-b]indole-1,4-dione, is a phosphodiesterase 5 (PDE-5) inhibitor, which is approved for the treatment of erectile dysfunction. The optimisation of tadalafil from its hydantoin lead compound, 2-Butyl-5-(4-methoxyphenyl)-5,6,11,11a-tetrahydro-1 H-imidazo[1',5':1,6]pyrido[3,4-b]indole-1,3(2H)-dione, is described Daugan A. et al. (2003), *J. Med. Chem.*, 46(21), pp 4533-4542 (Compound 2a). Daugan A. et al. report that a medicinal chemistry strategy identified the optimum compound, tadalafil through the synthesis of at least 48 compounds in a series of structure activity exercises from the lead compound.

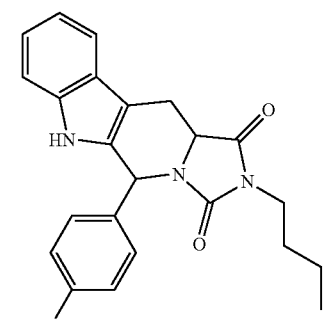

Compound 2a

Hydantoin lead

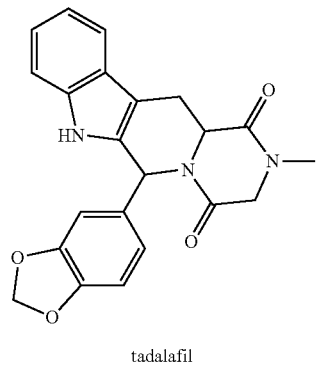

Compound 12a tadalafil

To demonstrate the utility of the invention in lead optimisation, the method of the invention was applied to the optimisation of the hydantoin lead compound, compound 2a.

Chemical Transformation Library

The chemical transformation database was encoded in a library 432 unique reactions. The lead optimisation strategy was carried out over 3 iterations (generations), starting from a single molecule, compound 2a. Over the 3 generations, beginning with a single molecule, 388,974 unique compounds were designed. The uniqueness of the compounds was assessed by comparison of the canonical tautomer SMILES (calculated using Accelrys Pipeline Pilot version 7.5).

Objective Scoring Method for PDE-5

In order to prevent biasing the system with knowledge that was not available to the authors of Daugan et al. in 2003, only published phosphodiesterase-5 structure-activity data up to 1999 (e.g. information available from *J. Med. Chem.* and *Bioorg. Med. Chem. Letts* articles—as available in the Starlite and WoMBAT databases) was used to construct the Bayesian models that were employed as objective scoring functions in analysis. Furthermore, the information used for the Bayesian models explicitly excluding the lead optimisation data reported in Daugan et al. itself. In this way, the information and power of the system was limited to same background knowledge on PDE-5 inhibitors as Daugan et al., when the original lead optimisation project was conducted.

Figure 5:
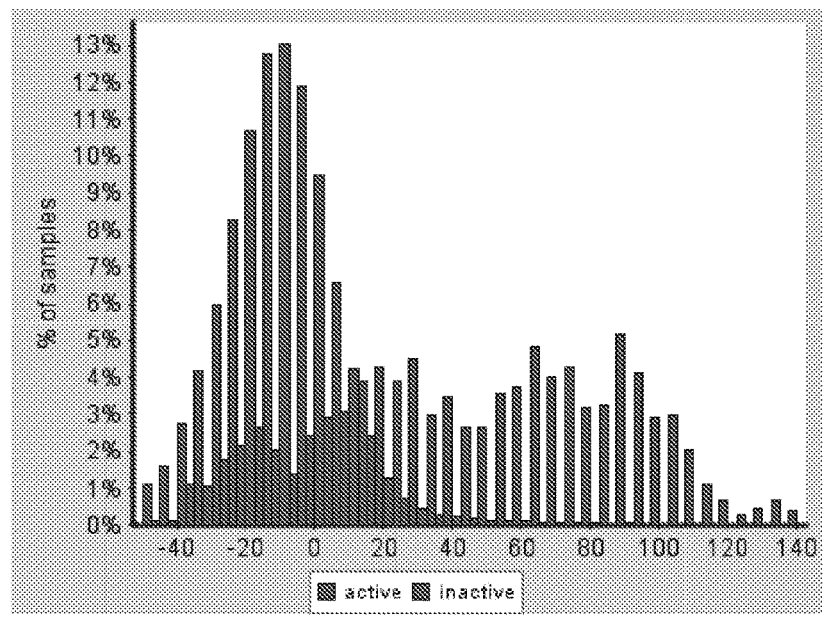
FIG. 5 is a graph showing the repartition of the compounds depending of their score for the Bayesian model of activity against PDE5.

Biological activity for the designed compounds was predicted using a Laplacian Naïve Bayesian model, built following the methods described by Nidhi et al. (2006, Prediction of biological targets for compounds using multiple-category Bayesian models trained on chemogenomics databases, *J. Chem. Info. Modeling*, 46, 1124-1133). Two models were built using Starlite and Wombat data: Starlite data contains 1010 PDE5A inhibitors (293,465 inactive) with an activity (inhibition constant) of less than 10 µM (Ki or IC50); and Wombat contains 832 PDE5 inhibitors compounds (372,045 inactive). The models were built using ECFP_6 as descriptors and using the Learn Molecular Categories component from Accelrys Pipeline Pilot. The AUC value for the Bayesian Model was 0.90190. The statistics for the quality of the model at different cut offs are shown in Table 2. The repartition of the known actives and inactives used to build the model, showing the distribution of score, is displayed in FIG. 5.

TABLE 2

Quality statistics depending on score cut-off for the PDE-5 Bayesian model

| tn | tp | fp | fn | Total_Accuracy | Positive_Recall | Negative_Recall | Precision | Enrichment_Factor | Sum_Score | score |
|---|---|---|---|---|---|---|---|---|---|---|
| 7609 | 1023 | 17536 | 50 | 0.32924 | 0.9534 | 7.0913 | 0.055122 | 1.3469 | 1.2826 | −20 |
| 19784 | 928 | 5361 | 145 | 0.78999 | 0.86486 | 18.438 | 0.14756 | 3.6055 | 1.6549 | 0 |
| 23128 | 862 | 2017 | 211 | 0.91502 | 0.80336 | 21.555 | 0.29941 | 7.3159 | 1.7184 | 10 |
| 23549 | 851 | 1596 | 222 | 0.93066 | 0.7931 | 21.947 | 0.34777 | 8.4976 | 1.7238 | 12.25 |
| 23924 | 826 | 1221 | 247 | 0.94401 | 0.7698 | 22.296 | 0.40352 | 9.8597 | 1.7138 | 15 |
| 24388 | 787 | 757 | 286 | 0.96022 | 0.73346 | 22.729 | 0.50972 | 12.455 | 1.6937 | 20 |
| 24779 | 695 | 366 | 378 | 0.97162 | 0.64772 | 23.093 | 0.65504 | 16.006 | 1.6193 | 30 |
| 25002 | 553 | 143 | 520 | 0.97471 | 0.51538 | 23.301 | 0.79454 | 19.414 | 1.4901 | 50 |
| 25094 | 389 | 51 | 684 | 0.97197 | 0.36253 | 23.387 | 0.88409 | 21.602 | 1.3345 | 70 |

Objective Scoring Method for ADME Properties

Predicted ADME properties for the generated virtual compounds were scored using the StarDrop ADMET properties calculation and scoremax was defined as the maximum score (out of the four prediction profiles). The full description of the properties can be found in the supplementary information.

In addition to predicting ADME properties, StarDrop was also used to generate scoring functions to define a profile for the compounds (e.g. intravenous/oral CNS/non-CNS compound). Details of the model methods and results can be found in Obrezanova et al., (2008, Automatic QSAR modelling of ADME properties: Blood-brain barrier penetration and aqueous solubility, *J. Computer-Aided Mol. Design* 22, pp 431-440); and Obrezanova, et al., (2007, Gaussian processes: A method for automatic QSAR modelling of ADME properties, *J. Chem. Info. Modelling* 47, pp 1847-1857).

To compare the score of the virtual compounds the scoring functions were applied to a set of drugs extracted from Drugstore. A full report with scoring properties and repartition can be found in the supplementary information.

Iterative Evolution of Compound Generations

The 432 transformations were applied systematic to the single lead compound to produce a first generation of 120 unique compounds which fulfilled the normal valency criteria and produced only one product from each transformation. The library of transformations (transformation database) was then systematically applied to each member of the subsequent populations until the Stop Condition was satisfied. In total, the system was run for 3 iterations and the results analysed. The number of unique compounds produced in each iteration is shown in Table 3. Thus, in total 388974 compounds were generated.

TABLE 3

Number of Unique Compounds Generated in each iteration

| Generation/Iteration | Number of Compounds per generation |
|---|---|
| 0 | 1 |
| 1 | 120 |
| 2 | 7914 |
| 3 | 380940 |

The final population of compounds was filtered following their molecular properties as defined by: (i) the HTS filter (for active groups), as encoded by the HTS component collection (Accelrys Pipeline Pilot Version 7.5); (ii) Rule of Five filter described by Lipinski et al. (1997, Experimental and computational approaches to estimate solubility and permeability in drug discovery and development settings, *Advanced Drug Delivery Reviews*, 23, 3-25); (iii) GSK rules described by Veber et al. (2002, Molecular Properties that Influence the Oral Bioavailability of Drug Candidates, *J. Med. Chem.*, 45, pp 2615-2623); and (iv) the unwanted group definition of Brenk et al. (2008, Lessons learnt from assembling screening libraries for drug discovery for neglected diseases, *Chem Med Chem* 3, pp 435-444). The filters used are 'drug like' molecular properties filters that are used commonly in medicinal chemistry and drug design and do not rely on predictive models. Alternatively, ADME (absorption, distribution, metabolism and excretion) properties can be predicted by any number of commercially available algorithms and can be used as an alternative filtering method.

Figure 6:
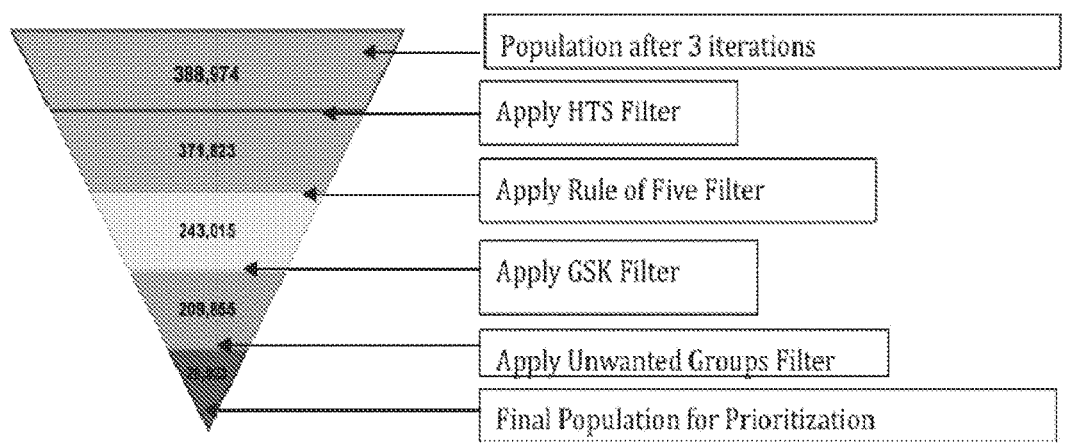
FIG. 6 is a schematic representation of the reduction in the number of members in the final population of molecules optimised against PDE5, by applying successive filters. After applying the filters the final population size for evaluation is reduced from 388974 to 29923 molecules, representing a reduction to 7.7% of the original population size.

By applying the set of filters sequentially, as shown in FIG. 6, the final generation of molecules was reduced from an initial population of 388974 members to a filtered population of 29923 members (representing 7.7% of the total data set). The HTS, Rule of Five and GSK rule filters are fast to process compared to the unwanted group definition and, therefore, the unwanted group filter was applied as the last filter to the already reduced final population size.

For comparison, in an alternative Example the same achievement objectives were used in a parallel algorithm which employed a transformation database comprising approximately 700 unique transformations. In view of the significant increase in population size between successive iterations and in comparison to the above-described algorithm, filters were applied during each iteration so as to reduce the population size of each generation of molecules. In this alternative example, the filters of Lipinski's Rule of Five, Unwanted Groups, Total Polar Surface Area and Number of Rotatable Bonds were applied to each of the first, second and third generations of molecules, so that the number of molecules for evaluation in each generation was reduced to a desired readily manageable amount as shown in Table 4.

TABLE 4

Number of unique compounds generated in each iteration with filters applied to intermediate (i.e. first and second) generations

| Generation/Iteration | Number of Compounds per generation |
|---|---|
| 0 | 1 |
| 1 | 11 |
| 2 | 1284 |
| 3 | 100408 |

Objective Scoring of Results

Figure 7A:
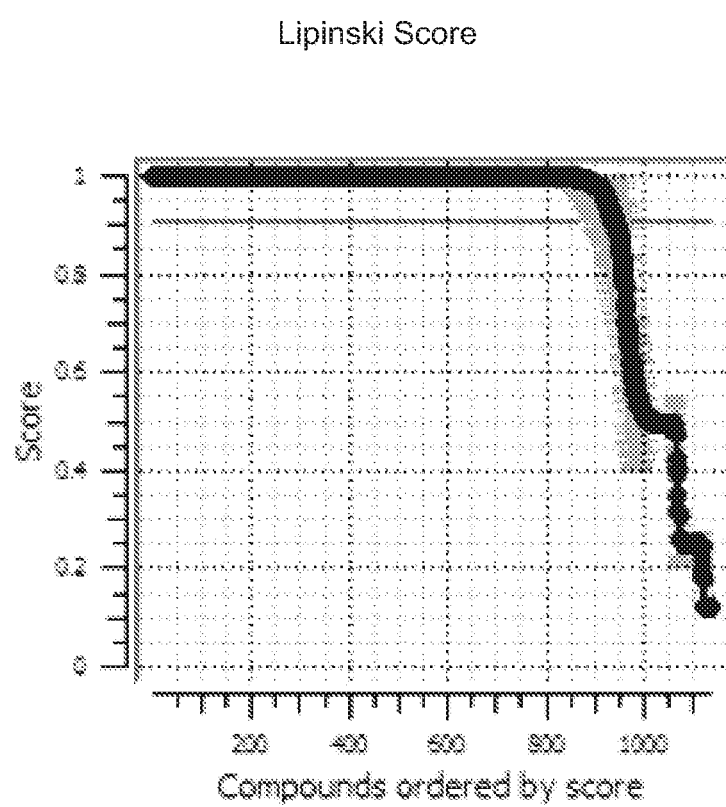
FIG. 7 illustrates the Lipinski score distribution (A) and the ADME score distribution (B) for virtual molecules optimised against PDE5.
Figure 7B:
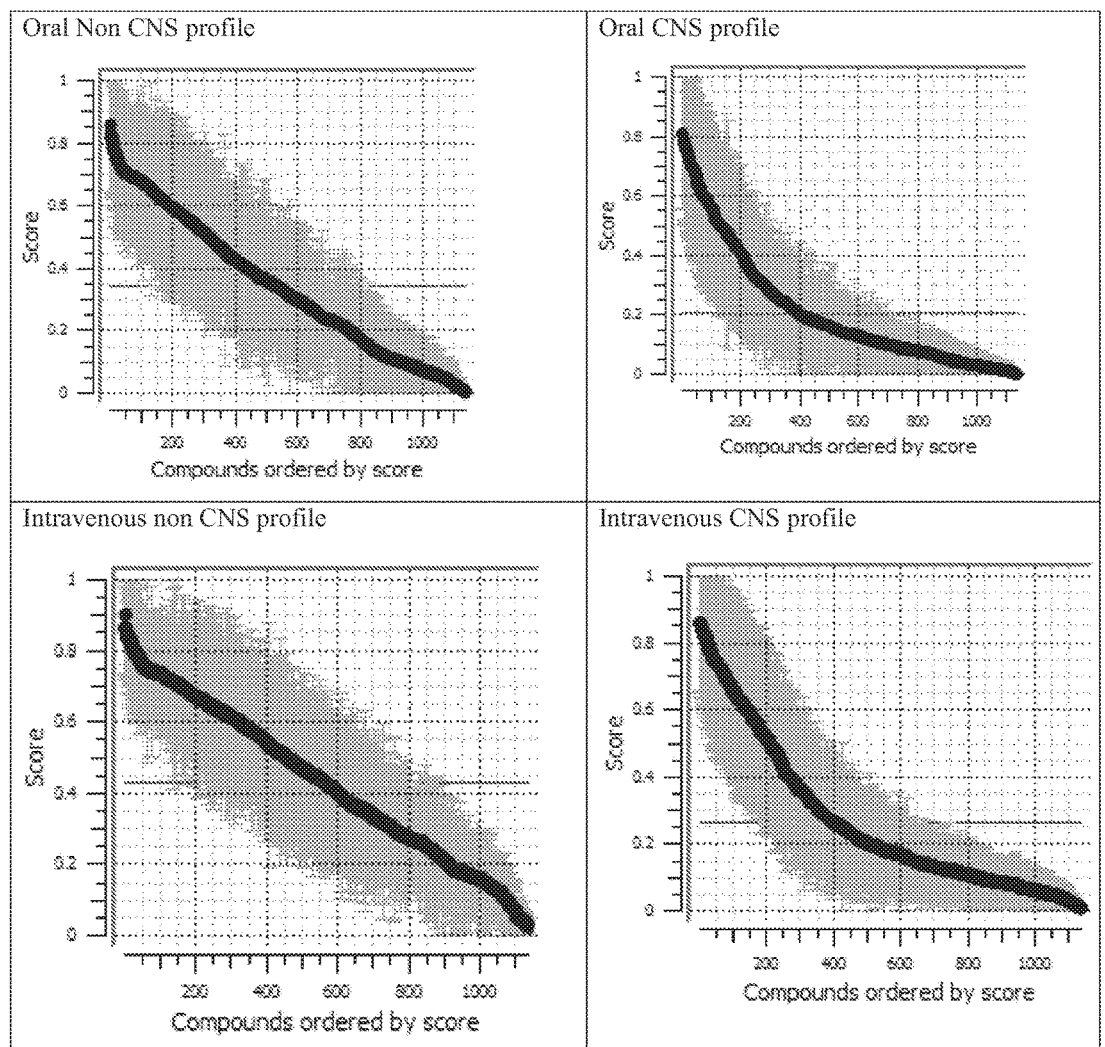

After all filters had been applied to the final population, the ADMET score distribution for the remaining population of 29,923 virtual compounds was calculated. FIG. 7A displays the results of the test for compliance to Lipinkis's Rules (where full compliance=1), and FIG. 7B demonstrates the results for the four scoring functions: (i) oral non-CNS profile; (ii) oral CNS profile; (iii) intravenous non-CNS profile; and (iv) intravenous CNS profile.

A 'consensus score' selected as the highest individual score against any ADME profile was used to represent the drug-like nature of the compounds.

As a comparison, the predicted ADME scores for tadalafil and its hydantoin lead molecule (Daugan A. et al.) are shown in Table 5, in which the standard deviation is indicated in brackets.

TABLE 5

Predicted ADME scores for tadalafil and its reported lead compound

| Molecule | Oral non CNS | Oral CNS | Intravenous non CNS | Intravenous CNS | Lipinski Score |
|---|---|---|---|---|---|
| Lead | 0.052 (0.057) | 0.018 (0.025) | 0.094 (0.075) | 0.032 (0.034) | 0.944 (0.158) |
| Tadalafil | 0.311 (0.177) | 0.088 (0.070) | 0.425 (0.183) | 0.120 (0.082) | 1.000 (0.001) |

Figure 8:
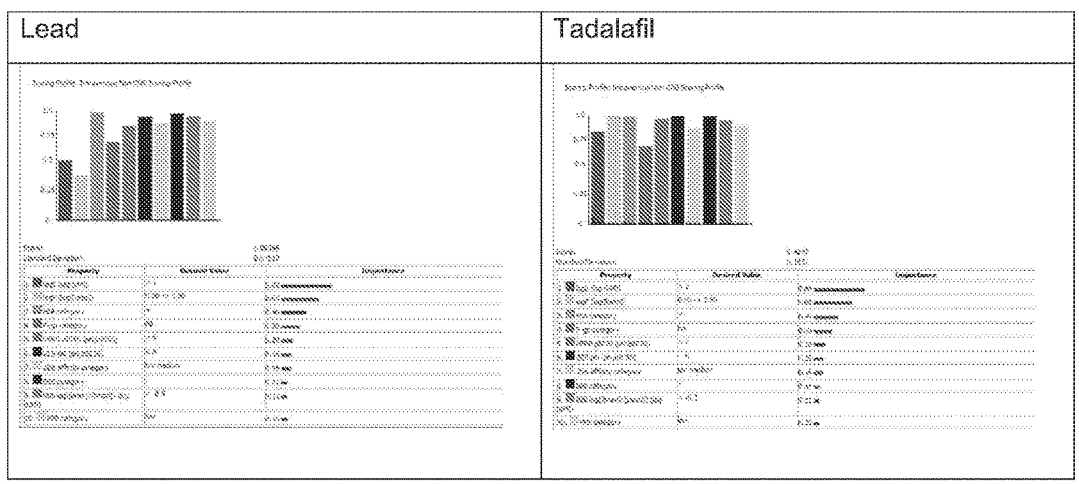
FIG. 8 illustrates the analysis of the intravenous non-CNS scoring profile (highest ADME score) for the lead compound and tadalafil in the evolution of molecules to target PDE5.

The full ADME analysis of the intravenous non-CNS scoring profile (highest ADME score) for the lead compound and tadalafil is shown in FIG. 8.

Interestingly, a comparison of the ADME scoring functions and Bayesian activity models for the population of molecules did not show a linear correlation between the two objectives.

Automatic Design of Tadalafil

The results of the automated molecular evolution strategy reveal tadalafil as one of the 388974 compounds generated by the method described. Moreover, tadalafil was also present in the final filtered population of 29923 virtual compounds. The reaction scheme below (Scheme I) illustrates one way in which a series of three reaction/transformation steps present in the transformation database of the invention, are able to transform the original hydantoin lead compound to the known drug tadalafil.

Figure 9:
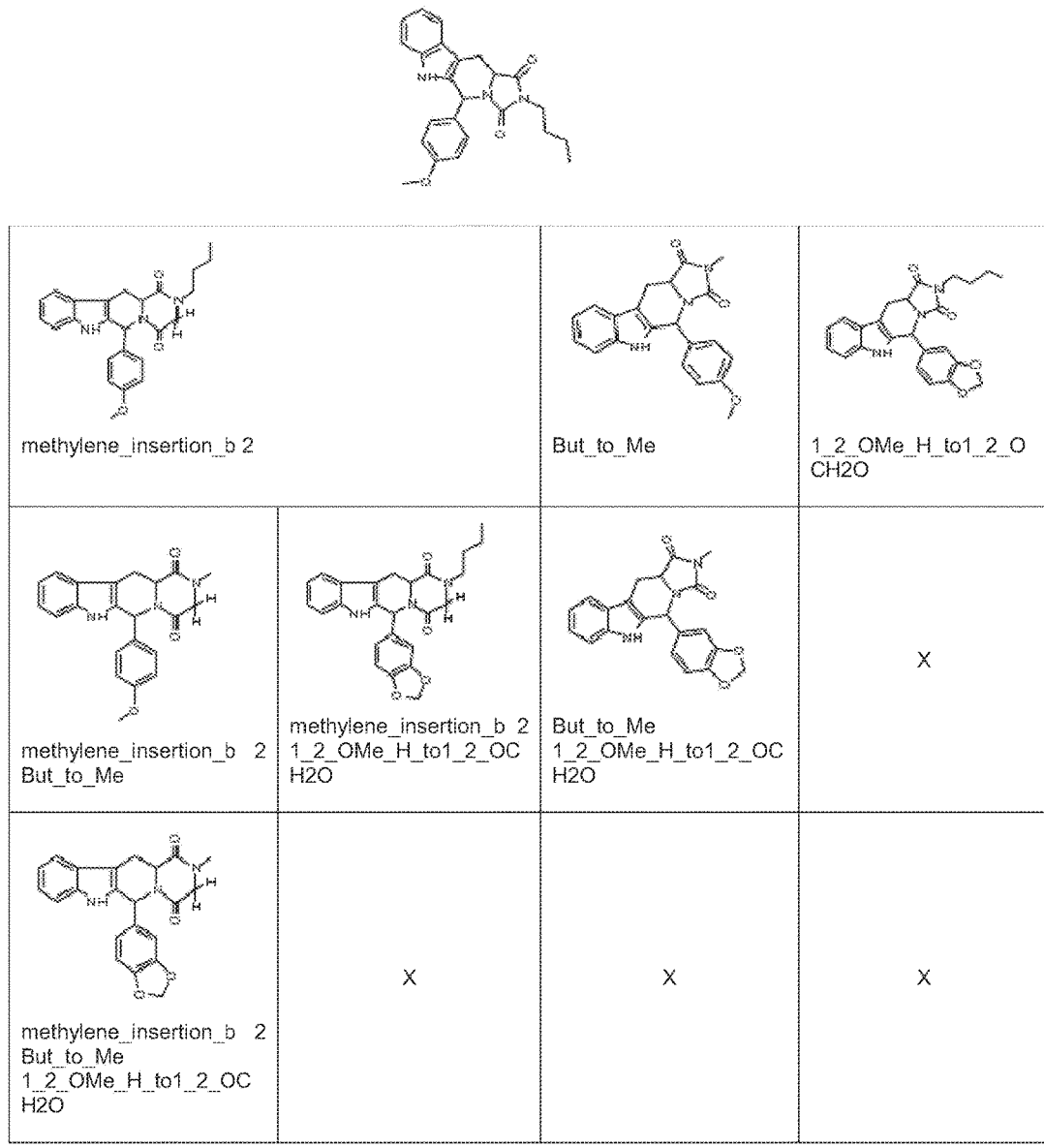
FIG. 9 is an evolution tree to illustrate how tadalafil was transformed from the lead compound in the optimisation of molecules against the PDE5 target.

Tadalafil may also be generated in this Example by performing the same reactions/molecular transformations as those shown in reaction Scheme I, but in a different order, as illustrated by the tadalafil evolution tree in FIG. 9. The evolution tree illustrates the lead compound (top centre) and the sequential transformations that result in the generation of tadalafil (bottom left). Duplicate molecules were removed by the duplicate molecule filter at each iteration, as indicated by "X" in the evolution tree, such that only one path actually generates tadalafil.

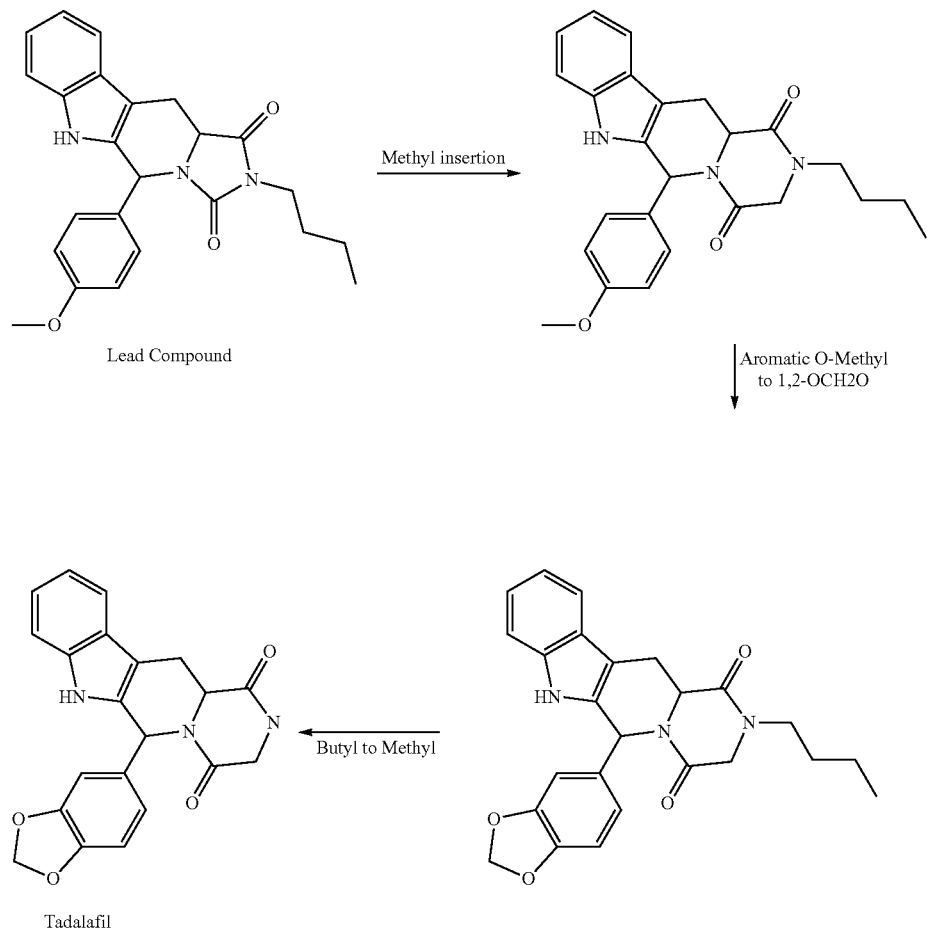

Scheme I

Prioritisation of Optimisation Results

For each compound two scores were assigned: (1) a score for predicted biological activity (using the Bayesian Model with published PDE5 data up to 1999 as described above); and (2) a prediction of ADME properties—the maximum score against any one of four ADME models as calculated by the commercial ADME prediction package (StarDrop, Optibrium Ltd, Cambridge UK).

For each compound two ranking scores were calculated: a Pareto rank and a Vector Distance to a defined Achievement Objective. In this Example, the Achievement Objective was defined as a Bayesian PDE5 Score of 100 and a normalised (ADME ScoreMax×100) ADME score of 50.

Interestingly, with respect to overall predicted biological activity in the population of virtual molecules, tadalafil was not the predicted highest ranking active compound in the Bayesian model, and neither was it the highest ranking most drug-like compound according to the ADME scoring function.

Pareto ranking of the final filtered population of 29923 compounds identified 44 non-dominated compounds in the first Pareto frontier. Tadalafil was on the first Pareto front, and therefore, in the top 44 compounds of the population according to Pareto ranking.

Figure 10:
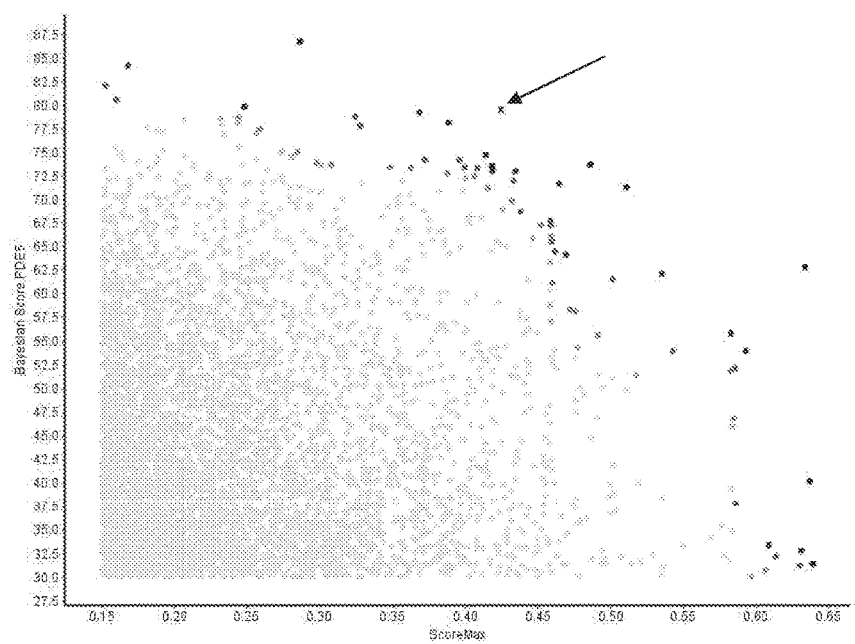
FIG. 10 illustrates the relative positions of the virtual molecules generated for binding to PDE5, assessed according to the achievement objectives of ADME score and Bayesian activity model against PDE5. The position of tadalafil in the population of virtual molecules is indicated by an arrow.

The vector distance of each virtual compound in the population to the defined Achievement Objective (i.e. Bayesian PDE5 Score=100, Normalised Maximum ADME Score=50) was also determined. These data demonstrated that tadalafil (with predicted scores: Bayesian PDE5 score=80, Normalised Maximum ADME Score=42.47), had a vector distance to the Achievement Object of 51, which was the shortest distance in the entire final population of virtual compounds. Accordingly, measurement of vector distance alone identified the approved PDE-5 drug, tadalafil as the predicted first ranked molecule in the final population generated and selected by the molecular evolution process. The position of tadalafil in the population of virtual molecules, as assessed by Bayesian PDE5 score and ADME score is indicated by an arrow in FIG. 10.

Therefore, according to the prioritisation scheme of the invention, tadalafil was ranked first in the entire virtual library of 38894 structures.

Model Building Methods:

Databases

StARlite database (version 31) was used for this study. StARlite is a database of bioactive molecules containing around 440,000 compounds with around 2,000,000 endpoints published in medicinal literature over the last 30 years. The data was processed for this Example by keeping only compounds with an activity which standard unit is nM and is inside the group of (IC50/Ki/Kd/EC50) with a protein target. Some custom filter were then applied (like activity>0).

Compounds were also standardized, and a unique tautomer form was kept, using the Pipeline Pilot components.

The drug targets: phosphodiesterase 5 (PDE5), and Phosphodiesterase 5a (PDE5a), were considered as a single unique target, PDE5. Only compounds where a recorded activity more potent that 10 µM affinity or inhibitory value (as defined by either IC50 or Ki or EC50 or Kb or Kd) against a PDE5 protein were included. If a compound had no PDE5 activity the target is assigned to 'none'.

The StARlite database also contains information on the publications in which the compounds are described, so it is possible to separate compounds according to the year of publication. In our study, tadalafil was released as a drug in 1999, however the article was published in two parts in 2003, hit to lead (Daugan et al., 2003, J. Med. Chem., 46(21), pp 4533-4542), and lead to drug (Daugan et al., 2003, J. Med. Chem., 46(21), pp 4525-4532).

Therefore, the data was split into two for generation of models: "training set"—compounds made before 1999 and including the hit to lead paper; and "test set"—containing every compound including those published after 1999, but excluding the information in the lead to drug paper. The first data set contained 75,961 molecules, and the second data set contained 138,091 molecules.

Descriptors

The descriptors used are structural information with the Extended Connectivity Fingerprint (ECFP; Rogers & Hahn (2010), J. Chemical Information and Modeling, 50, pp 742-54). These types of descriptors have been used in other studies with good results (Glick et al., 2006, Enrichment of high-throughput screening data with increasing levels of noise using support vector machines, recursive partitioning, and laplacian-modified naive bayesian classifiers, J. Chemical Information and Modelling, 46, pp 193-200; Hert et al., 2004, Comparison of topological descriptors for similarity-based virtual screening using multiple bioactive reference structures, Org. Biomol. Chem., 2, pp 3256-3266; Klon et al., 2004, Finding More Needles in the Haystack: A Simple and Efficient Method for Improving High-Throughput Docking Results. J. Med. Chem., 47, pp 2743). A neighbourhood of size 6 was selected to match the parameters used in the study of Nidhi et al. (2006, Prediction of biological targets for compounds using multiple-category Bayesian models trained on chemogenomics databases, J. Chemical Information and Modeling, 46, pp 1124-1133).

Bayesian Model

The Bayesian models were built according to the methods describe by Nidhi et al. (2006). A review of the application of Bayesian activity predictions in drug discovery can be found in Bender (2011)—to be published (Bender, 2011, Bayesian methods in virtual screening and chemical biology, Methods in Molecular Biology, Clifton, N.J., 672, pp 175-196.

The models were built using standard methods in the Accelrys's Pipeline Pilot software (Xia et al., 2004, Classification of Kinase Inhibitors Using a Bayesian Model, J. Med. Chem., 47, pp 4463-4470), which automatically creates a Laplacan-modified Bayesian model for PDE5. It is a two-category model; good molecules are considered to be the active PDE5 compounds, the other compounds are considered the bad molecules. A compound is considered "active" if the activity (e.g. binding affinity/inhibition constant) is below 10 µM.

Once the model has been built it can be used to calculate a score for PDE5, and a high score provides more confidence of binding.

Validation

For validation, the data was split into two: compounds were clustered and split using the cluster ID to which they belong, with even numbers in the validation training set and odd numbers in the test set. The distribution of unique compounds, active and inactive for each set is in Table 6.

TABLE 6

Distribution of unique compounds for each data set

| Set | Active | Inactive |
| --- | --- | --- |
| Validation Training | 477 | 75,484 |
| Validation Test | 885 | 137,206 |
| Whole Set | 1362 | 212,690 |

Test and training set statistics were assessed using a score cut-off maximising the Sum Score parameter as described in Prathipati et al., (2008), Global Bayesian Models for the Prioritization of Antitubercular Agents. *J Chemical Information and Modeling*, 48, pp 2362-2370; and a score cut-off maximising the MCC parameter as described in Cannon et al., (2008), A Novel Hybrid Ultrafast Shape Descriptor Method for use in Virtual Screening, *Chem. Central J.* 2, pp 3.

The following parameters were measured:
TN=true negative, TP=true positive, FP=false positive, FN=false negative
N=total number of compounds
Total accuracy=(TP+TN)/(N)
Sensitivity=TP/(TP+FN)
Specificity=TN/(FP+TN)
False positive (FP) rate=FP/(FP+TN)
False negative (FN) rate=FN/(TP+FN)
Precision=TP/(TP+FP)
Enrichment factor=Precision/((TP+FN)/(N))
Sum Score=Total Accuracy+Sensitivity
Matthews correlation coefficient (MCC)=((TP*TN−FP*FN)/sqrt((TP+FP)*(TP+FN)*(TN+FP)*(TN+FN)))
F measure=2*Precision*Sensitivity/(Precision+Sensitivity)
ROC score=area under ROC curve independent of score cut-off (Triballeau, et al., (2005), Virtual screening workflow development guided by the "receiver operating characteristic" curve approach. Application to high-throughput docking on metabotropic glutamate receptor subtype 4. *J. Med. Chem.*, 48, pp 2534-2547.

Calculation

Virtual molecules can be processed by assigning each compound a score for PDE5, and then ranking the population of compounds from best (highest score) to worst (lowest score).

Example 2

Selective Optimisation of a Side Activity of a Known Drug into the Primary Activity of a New Compound The most successful strategy to date for drug discovery has been the modification of one drug to create a new drug. The molecular exploration of existing compounds by structural modification to create new compounds with new activities has been proposed as a strategy, for example, by Wermurth (2004, *J. Med. Chem.,* 47(6), 1303-1314; and Wermuth, (2006), *Drug Discovery Today*, 11(3/4), 160-164). This strategy, i.e. where the secondary weak activity of a drug for a target is optimised to create a new compound with improved activity against that side target, has been termed "Selective Optimisation of Side Activities" (SOSA). Typically the original primary activity is reduced as a result of the optimisation process.

In this Example compounds with new biological activity profiles are designed from an existing known drug, donepezil, an acetylcholinesterase inhibitor approved for the treatment of Alzheimer's disease. This Example describes how, in two parallel methods of the invention, donepezil was evolved into optimised ligands for dopamine D2 and dopamine D4, respectively. Two evolutionary strategies were run independently against the desired target profiles (i.e. either dopamine D2 or dopamine D4 molecular targets) using donepezil as the initial starting point for both campaigns. At the time this Example was carried out no public information was available on the binding affinity of donepezil for either dopamine D2 or dopamine D4 receptors.

Objective Activity Scoring Method

Structure-activity data used to create the Bayesian activity models (see FIG. 11) was extracted from the EBI Starlite database (2008) and from reports in the journals: *J. Med. Chem.* (1980-2008) and *Bioorg. Med. Chem. Letts* (1990-2008). As shown in FIG. 11, three activity models were created, for dopamine D2 (A), dopamine D4 (B)—the two new target molecules, and acetylcholinesterase (C), the initial target molecule. The activity score against Model 1 (either dopamine D2 or D4 receptor) is used in the Strategy to select compounds from each generation with an improved score. Model 2 is used only to monitor the activity and not used in the selection process. The starting structure, donepezil scored 9.0 for the dopamine D2 receptor model and 26.0 against the dopamine D4 receptor model. The experimental receptor profiling of donepezil subsequently revealed the percentage inhibition of the dopamine D2 and D4 receptors to be 18.6% and 89.2%, respectively. The Ki binding affinities of donepezil to the dopamine D4 receptor was determined to be 614 nM, whilst the binding affinity of donepezil to the dopamine D2 receptor was too weak to measure in the assay used. All compound receptor binding profiles and Ki determinations were generously provided by the National Institute of Mental Health's Psychoactive Drug Screening Program, Contract # HHSN-271-2008-00025-C (NIMH PDSP).

Chemical Evolution Strategy

The chemical transformation set was encoded in a library of approximately 700 unique reactions. The System was run over 6 iterations (generations) using the drug donepezil, an acetylcholinestrase inhibitor approved for the treatment of Alzheimer's disease as the initial seed compound against each strategy. The Strategies was set to optimise, independently, the activity against the Dopamine D4 Objective only (as defined by the Dopamine D4 Bayesian Model) and the Dopamine D2 Objective only (as defined by the Dopamine D2 Bayesian Model) only. The predictive acetylcholinestrase activity (as calculated by the acetylcholinestrase Bayesian Model) was monitored throughout the process but played no part in the generational selection of compounds.

For each generated compound Prediction 1 is defined as the value calculated in the Dopamine_Receptor_ECFP Bayesian Model. The Strategy employed was:

Prediction 1>[Prediction 1]Mean+[Prediction 1]StdDev

Where the compounds selected has a calculated Prediction 1 value greater than the mean plus standard deviation of the entire set of compounds generated for the entire population at that iteration.

For each iteration the top 10000 compounds with the highest predicted values that passed the defined filters plus 500 random chosen compounds (selected as defined in the above algorithm) were selected as the parent compounds for the subsequent generation of transformations.

Objective Scoring of ADME Properties

The ADME scoring objective was not employed as part of the evolution strategy but calculated on the final population with a Prediction 1 (i.e. dopamine D4 or dopamine D2) score greater than 90. ADME scores were generated using the Stardrop program (as described previously) with the maximum score from any one of the four predicted functions (as described above) as the ADME score for the compound.

Prioritisation of Optimisation Results: Dopamine D4 Optimisation

For each compound two method ranking scores were calculated: a Pareto front and a Vector Distance to a defined Achievement Objective. The Achievement Objective was defined as a Bayesian D4 Score of 140 and a normalised (ADME ScoreMax×100) ADME score of 50.

Figure 12:
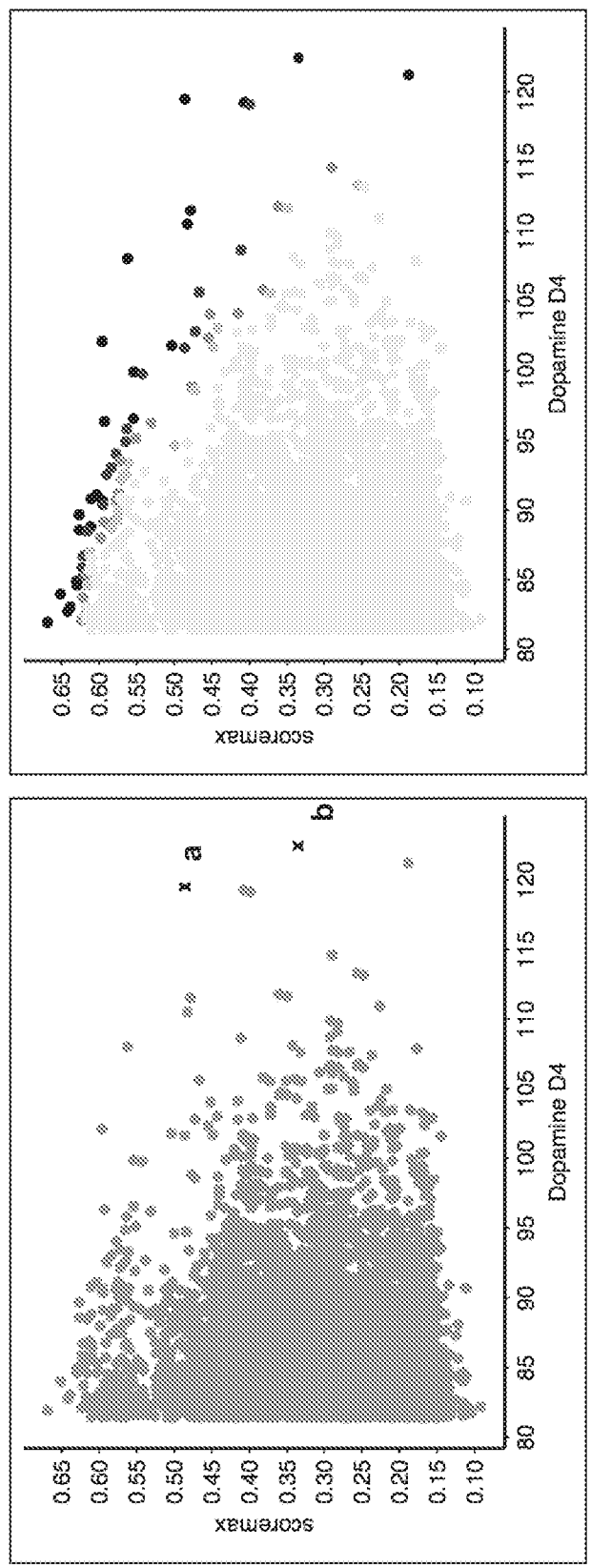
FIG. 12 shows the optimisation of compounds for binding to dopamine D4 (A). Bayesian score for predicted dopamine D4 activity (x-axis) and maximum predicted ADME score, normalised (y-axis). The compounds STT-00185641 (a) and STT-00186538 (b) are identified with an "X". (B) The same dataset as in FIG. 12(A) with molecules of each Pareto front identified by colour. The first Pareto front (Pareto Front=1) is coloured black; the second Pareto front (Pareto Front=2) is coloured dark grey; and third Pareto front (Pareto Front=3) is coloured light grey. The compounds STT-00185641 and STT-00186538 are positioned on the first Pareto front.
Figure 13:
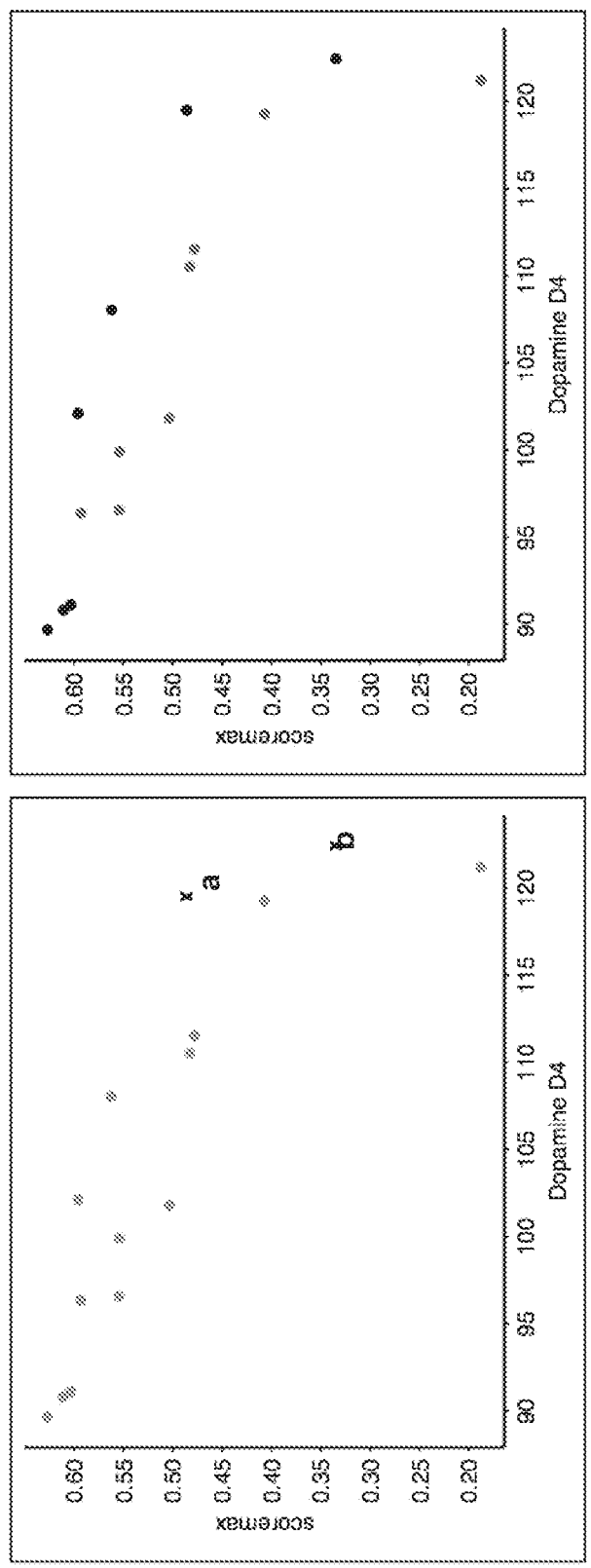
FIG. 13 shows the top 15 compounds of the optimisation depicted in FIG. 12, as determined by vector distance to the achievement objectives, Bayesian Dopamine D4 Score=140 and ADME ScoreMax=50 (A). Compounds STT-00185641 (a) and STT-00186538 (b) are each identified by an "X". (B) The same dataset as in FIG. 13(A) where each Pareto Front is coloured separately. All 15 prioritised compounds lay on the first Pareto front (black) or the second Pareto front (grey).

The results are shown in the Tables 6 and 7 and FIGS. 12 and 13. Since the acetyicholinesterase activity was not selected for, the predicted activity against the original target decreased through each subsequent generation of compounds while predicted dopamine D4 activity tended to increase for individuals in the populations.

FIG. 12(A) shows the entire final population of 50,000 compounds generated by the optimisation of donepezil against the dopamine D4 objective and the ADME objective. The x-axis represents the Bayesian score for predicted dopamine D4 activity and the y-axis represents the maximum predicted ADME score, normalised. The higher the score in each prediction, the higher the predicted likelihood of compounds having good dopamine D4 receptor binding activity and/or good pharmacokinetic properties, respectively. Based on the results, two compounds were selected for experimental testing, STT-00185641 and STT-00186538 (marked (a) and (b) respectively on the graph). The same dataset is shown in FIG. 12(B), except the compounds on each of the first three Pareto fronts are identified: first Pareto front (black); second Pareto front (dark grey); and third Pareto front (light grey). It can be seen that the compounds STT-00185641 and STT-00186538 are both positioned on the first Pareto front. With reference to FIGS. 13(A) and 13(B), the top 15 compounds with the shortest vector distances to the Achievement Objective scores (Bayesian Dopamine D4 Score=140 and ADME ScoreMax=50) were prioritised and are indicated on the graph. These 15 molecules are located either on the first (black) or second (dark grey) Pareto fronts (see Table 7).

Table 7 shows the data for the ten compounds prioritised in the first Pareto front of molecules optimised from donepezil against the dopamine D4/ADME achievement objectives. The vector distance of each molecule to the first achievement objective (D4-140, ADME=50) is listed. In addition to vector distance, the dopamine D4 activity is indicated in the corresponding column and the predicted activity for other targets for each compound are listed in the 'Side Effects' column with their corresponding Bayesian Model score. The Bayesian models marked as High Confidence are those for which there is an unambiguous assignment of the compounds to molecular target in the original literature from which the data was derived. The All Compound models are constructed from all the activity data points assigned to that target, including data where the exact molecular target assignment may be ambiguous, in the original literature. Data for the 15 prioritised dopamine D4 antagonists optimised from donepezil are reported in Table 8. The compounds are ordered according to predicted dopamine D4 Bayesian activity scores, with the highest scoring compound listed first. The vector distance to the first Achievement Objective (D4=140, ADME=50) is also listed. Compounds were prioritised on the basis of vector distance. In addition to the objective dopamine D4 activity, the predicted activity for other targets for each compound are listed in the 'Side Effects' column with their corresponding Bayesian Model score.

By ranking the compounds generated in the method according to Bayesian activity models scoring, compound STT-00185638 had the highest predicted score. However, by prioritising the compounds by the shortest vector distance to the first Achievement Objective (D4=150, ADME=50) the compounds are ordered by STT-00185641 (vector distance=30.525), compound 6_3 (distance=32.107) and compound STT-00185638 (distance=32.132). Notably, twelve of the top fifteen compounds belong to a 2,3-dihydro-indol-1-yl chemotype. To confirm the efficacy of the model and the actual activity of the prioritised compounds, compounds STT-00185641 and STT-00185638, which both belong to the 2,3-dihydro-indol-1-yl class, were selected for testing (see Table 9).

TABLE 7

Predicted data parameters for 10 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 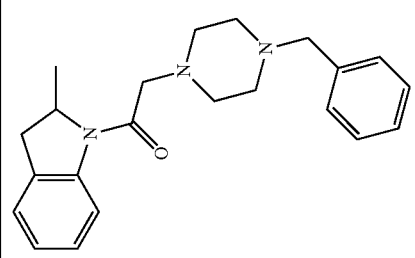 STT-00185638 | 1 | IntraCNS: 0.2941 IntraNonCNS: 0.3348 OralCNS: 0.1931 OralNonCNS: 0.2198 | 122 | 32.132 | Dopamine D4 receptor Dopamine D2 receptor Alpha-1b adrenergic receptor Alpha-1d adrenergic receptor Alpha-1a adrenergic receptor | 109.34 69.356 64.376 63.186 61.775 | Dopamine D4 receptor Dopamine D2 receptor Sigma opioid receptor Tripeptidyl aminopeptidase Muscarinic acetylcholine receptor M3 | 113.05 68.085 28.964 25.603 22.679 |
| 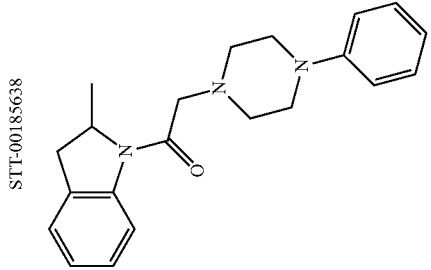 STT-00185641 | 1 | IntraCNS: 0.4859 IntraNonCNS: 0.4296 OralCNS: 0.305 OralNonCNS: 0.2697 | 120 | 30.525 | Dopamine D4 receptor Alpha-1b adrenergic receptor Alpha-1d adrenergic receptor Alpha-1a adrenergic receptor Dopamine D2 receptor | 111.40 78.039 77.379 75.630 75.396 | Dopamine D4 receptor Dopamine D2 receptor Tripeptidyl aminopeptidase Serotonin 7 (5-HT7) receptor Voltage-gated T-type calcium channel alpha-1G subunit | 111.87 73.205 28.276 26.928 23.279 |

TABLE 7-continued

Predicted data parameters for 10 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 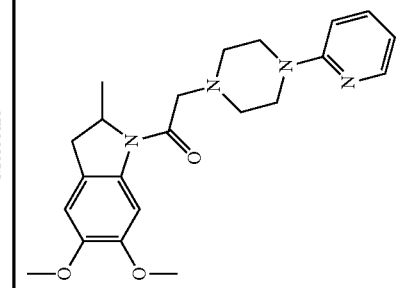 6_20 | 1 | IntraCNS: 0.2914 IntraNonCNS: 0.5624 OralCNS: 0.1842 OralNonCNS: 0.3439 | 108 | 42.421 | Dopamine D4 receptor Dopamine D2 receptor Alpha-1b adrenergic receptor Alpha-1d adrenergic receptor Alpha-1a adrenergic receptor | 95.705 61.300 60.691 60.318 59.138 | Dopamine D4 receptor Dopamine D2 receptor Dopamine D3 receptor Alpha-2a adrenergic receptor Serotonin 1a (5-HT1a) receptor | 99.193 62.014 25.692 15.274 13.511 |
| 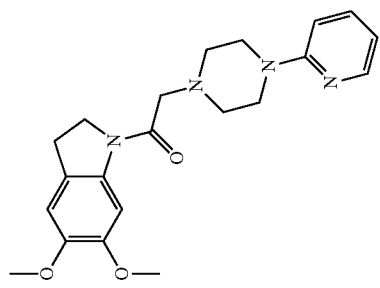 6_105 | 1 | IntraCNS: 0.3022 IntraNonCNS: 0.5962 OralCNS: 0.2021 OralNonCNS: 0.3857 | 102 | 48.856 | Dopamine D4 receptor Dopamine D2 receptor Alpha-1b adrenergic receptor Alpha-1d adrenergic receptor Alpha-1a adrenergic receptor | 89.974 61.139 54.336 53.900 52.634 | Dopamine D4 receptor Dopamine D2 receptor Dopamine D3 receptor Cytochrome P450 1A2 Multidrug resistance-associated protein 1 | 94.130 62.130 32.173 30.064 17.502 |

TABLE 7-continued

Predicted data parameters for 10 virtual molecules on the first Pareto front of the population optimised in the dopamine D4 activity model

| Molecule | ParetoFront | ScoreD | Vector Distance (D4 = 140, ADME = 50) | SideEff_AllCpds | Dopamine D4 SideEffScore_AllCpds | SideEff_HighConfidence | SideEffScore_HighConfidence |
|---|---|---|---|---|---|---|---|
| 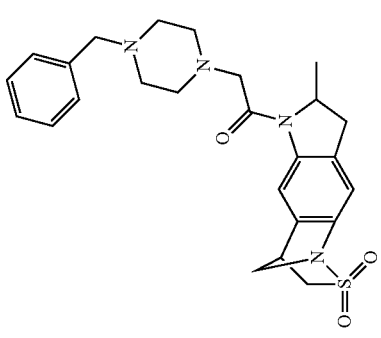 6_1227 | 1 | IntraCNS: 0.2306 IntraNonCNS: 0.6034 OralCNS: 0.1511 OralNonCNS: 0.3781 | 59.799 | Dopamine D4 receptor Dopamine D2 receptor Alpha-1b adrenergic receptor Alpha-1d adrenergic receptor Alpha-1a adrenergic receptor | 77.842 46.770 44.836 43.720 42.412 | Dopamine D4 receptor Dopamine D2 receptor Sigma opioid receptor Muscarinic acetylcholine receptor M3 Voltage-gated T-type calcium channel alpha-1G subunit | 81.378 46.449 28.703 22.463 19.383 |
| 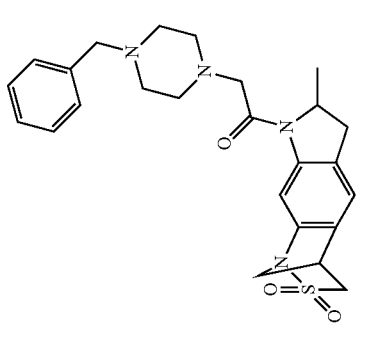 6_1306 | 1 | IntraCNS: 0.2335 IntraNonCNS: 0.611 OralCNS: 0.1544 OralNonCNS: 0.3862 | 60.235 | Dopamine D4 receptor Dopamine D2 receptor Alpha-1b adrenergic receptor Alpha-1d adrenergic receptor | 77.393 46.453 43.489 42.358 41.007 | Dopamine D4 receptor Dopamine D2 receptor Sigma opioid receptor Muscarinic acetylcholine receptor M3 Voltage-gated T-type calcium channel alpha-1G subunit | 80.996 45.508 28.574 22.322 19.363 |

TABLE 7-continued

Predicted data parameters for 10 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 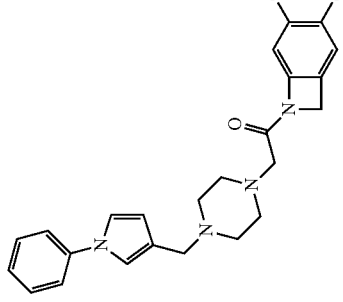 6_1692 | 1 | IntraCNS: 0.1981<br>IntraNonCNS: 0.6268<br>OralCNS: 0.1339<br>OralNonCNS: 0.4097 | 90 | 61.653 | Dopamine D4 receptor<br>Dopamine D2 receptor<br>Dopamine D3 receptor<br>Alpha-1b adrenergic receptor<br>Alpha-1d adrenergic receptor | 78.697<br>56.558<br>37.199<br>20.079<br>19.223 | Dopamine D4 receptor<br>Dopamine D2 receptor<br>Dopamine D3 receptor<br>Cytochrome P450 3A4<br>Serotonin 7 (5-HT7) receptor | 78.972<br>40.185<br>23.535<br>17.047<br>13.150 |
| 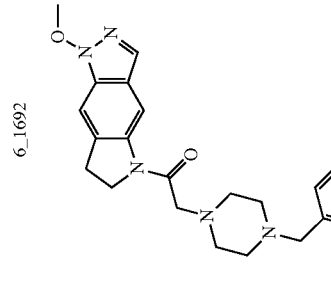 6_4855 | 1 | IntraCNS: 0.193<br>IntraNonCNS: 0.6302<br>OralCNS: 0.131<br>OralNonCNS: 0.4136 | 85 | 66.404 | Dopamine D4 receptor<br>Dopamine D2 receptor<br>Alpha-1b adrenergic receptor<br>Alpha-1d adrenergic receptor<br>Alpha-1a adrenergic receptor | 69.655<br>40.028<br>28.697<br>27.559<br>26.522 | Dopamine D4 receptor<br>Dopamine D2 receptor<br>Muscarinic acetylcholine receptor M3<br>Sigma opioid receptor<br>Dopamine D3 receptor | 76.058<br>42.055<br>19.506<br>17.675<br>17.250 |

TABLE 7-continued

Predicted data parameters for 10 virtual molecules on the first Pareto front of the population optimised in the dopamine D4 activity model

| Molecule | ParetoFront | ScoreD | Vector Distance (D4 = 140, D4 ADME = 50) | SideEff_AllCpds | Dopamine D4 | SideEffScore_AllCpds | SideEff_HighConfidence | SideEffScore_HighConfidence |
|---|---|---|---|---|---|---|---|---|
| 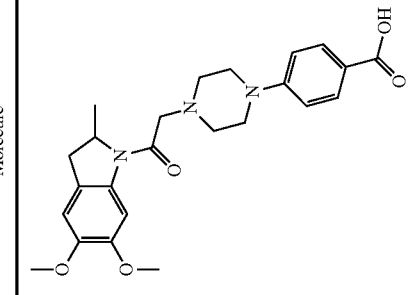 6_5889 | 1 | IntraCNS: 0.1716<br>IntraNonCNS: 0.6516<br>OralCNS: 0.1218<br>OralNonCNS: 0.4538 | 84 | 67.746 | Dopamine D4 receptor<br>Alpha-1b adrenergic receptor<br>Alpha-1d adrenergic receptor<br>Alpha-1a adrenergic receptor<br>Dopamine D2 receptor | 58.735<br>42.209<br>41.981<br>40.472<br>32.492 | Dopamine D4 receptor<br>Dopamine D2 receptor<br>Alpha-2c adrenergic receptor<br>Alpha-2b adrenergic receptor<br>Alpha-2a adrenergic receptor | 61.372<br>34.136<br>19.635<br>14.198<br>13.718 |
| 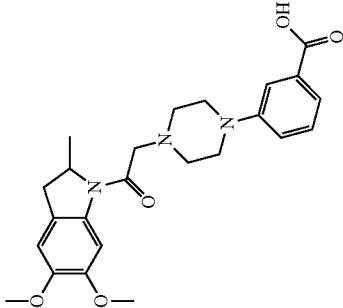 6_8977 | 1 | IntraCNS: 0.1767<br>IntraNonCNS: 0.669<br>OralCNS: 0.1295<br>OralNonCNS: 0.4813 | 82 | 70.140 | Dopamine D4 receptor<br>Alpha-1b adrenergic receptor<br>Alpha-1d adrenergic receptor<br>Alpha-1a adrenergic receptor<br>Dopamine D2 receptor | 56.438<br>45.058<br>44.607<br>43.875<br>32.680 | Dopamine D4 receptor<br>Dopamine D2 receptor<br>Alpha-2c adrenergic receptor<br>Plasminogen activator inhibitor-1<br>Alpha-1a adrenergic receptor | 59.207<br>34.537<br>16.362<br>13.679<br>11.255 |

TABLE 8

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 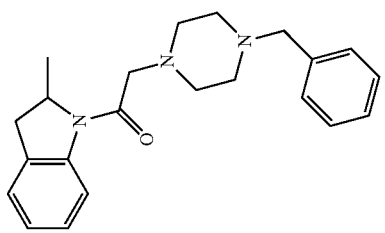 STI-0018638 | 1 | IntraCNS: 0.2941 IntraNonCNS: 0.3348 OralCNS: 0.1931 OralNonCNS: 0.2198 | 122 | 32.132 | Dopamine D4 receptor Dopamine D2 receptor Alpha-1b adrenergic receptor Alpha-1d adrenergic receptor Alpha-1a adrenergic receptor | 109.34 69.356 64.376 63.186 61.775 | Dopamine D4 receptor Dopamine D2 receptor Sigma opioid receptor Tripeptidyl aminopeptidase Muscarinic acetylcholine receptor M3 | 113.05 68.085 28.964 25.603 22.679 |
| 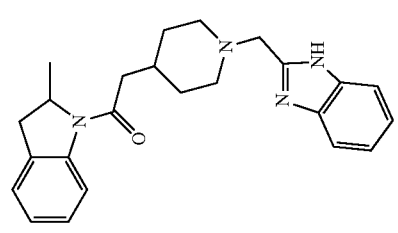 6_2 | 2 | IntraCNS: 0.06166 IntraNonCNS: 0.1881 OralCNS: 0.03675 OralNonCNS: 0.1009 | 121 | 42.445 | Dopamine D4 receptor Alpha-1b adrenergic receptor Alpha-1d adrenergic receptor Alpha-1a adrenergic receptor Dopamine D2 receptor | 116.75 66.970 65.541 63.334 43.587 | Dopamine D4 receptor Dopamine D2 receptor Tripeptidyl aminopeptidase Serotonin 3b (5-HT3b) receptor Serotonin 3a (5-HT3a) receptor | 119.19 43.027 43.016 14.206 14.012 |

TABLE 8-continued

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| STT-00185641 | 1 | IntraCNS: 0.4859<br>IntraNonCNS: 0.4296<br>OralCNS: 0.305<br>OralNonCNS: 0.2697 | 120 | 30.525 | Dopamine D4 receptor<br>Alpha-1b adrenergic receptor<br>Alpha-1d adrenergic receptor<br>Alpha-1a adrenergic receptor<br>Dopamine D2 receptor | 111.40<br>78.039<br>77.379<br>75.630<br>75.396 | Dopamine D4 receptor<br>Dopamine D2 receptor<br>Tripeptidyl aminopeptidase<br>Serotonin 7 (5-HT7) receptor<br>Voltage-gated T-type calcium channel alpha-1G subunit | 111.87<br>73.205<br>28.276<br>26.928<br>23.279 |
| 6_3 | 2 | IntraCNS: 0.09377<br>IntraNonCNS: 0.4071<br>OralCNS: 0.05872<br>OralNonCNS: 0.2466 | 119 | 32.107 | Dopamine D4 receptor<br>Alpha-1b adrenergic receptor<br>Alpha-1d adrenergic receptor<br>Alpha-1a adrenergic receptor<br>Dopamine D2 receptor | 111.85<br>53.574<br>52.473<br>50.378<br>29.399 | Dopamine D4 receptor<br>Dopamine D2 receptor<br>Tripeptidyl aminopeptidase<br>Serotonin 3b (5-HT3b) receptor<br>Serotonin 3a (5-HT3a) receptor | 112.48<br>31.268<br>22.603<br>15.364<br>15.114 |

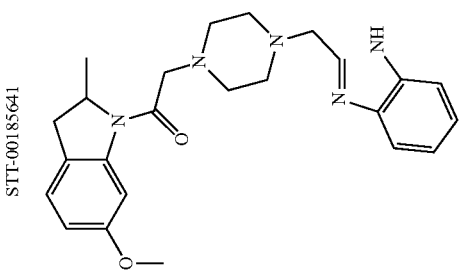

TABLE 8-continued

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 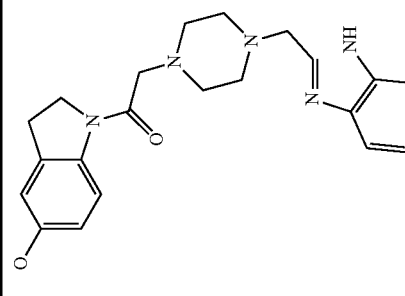 6_10 | 2 | IntraCNS: 0.1012<br>IntraNonCNS: 0.4784<br>OralCNS: 0.06927<br>OralNonCNS: 0.3167 | 112 | 38.547 | Dopamine D4 receptor<br>Alpha-1b adrenergic receptor<br>Alpha-1d adrenergic receptor<br>Alpha-1a adrenergic receptor<br>Dopamine D2 receptor | 104.13<br>40.519<br>39.428<br>37.282<br>28.267 | Dopamine D4 receptor<br>Dopamine D2 receptor<br>Cytochrome P450 1A2<br>Serotonin 3b (5-HT3b) receptor<br>Serotonin 3a (5-HT3a) receptor | 105.87<br>31.000<br>24.117<br>19.599<br>19.478 |
|  6_13 | 2 | IntraCNS: 0.1004<br>IntraNonCNS: 0.4826<br>OralCNS: 0.06895<br>OralNonCNS: 0.3206 | 111 | 39.515 | Dopamine D4 receptor<br>Alpha-1b adrenergic receptor<br>Alpha-1d adrenergic receptor<br>Alpha-1a adrenergic receptor<br>Dopamine D2 receptor | 102.60<br>48.396<br>47.118<br>45.061<br>26.738 | Dopamine D4 receptor<br>Dopamine D2 receptor<br>Cytochrome P450 1A2<br>Serotonin 3b (5-HT3b) receptor<br>Serotonin 3a (5-HT3a) receptor | 104.62<br>29.947<br>21.397<br>18.077<br>17.966 |

TABLE 8-continued

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 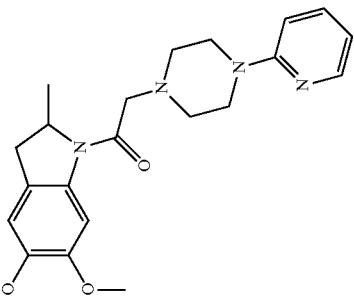 6_20 | 1 | IntraCNS: 0.2914<br>IntraNonCNS: 0.5624<br>OralCNS: 0.1842<br>OralNonCNS: 0.3439 | 108 | 42.421 | Dopamine D4 receptor<br>Dopamine D2 receptor<br>Alpha-1b adrenergic receptor<br>Alpha-1d adrenergic receptor<br>Alpha-1a adrenergic receptor | 95.705<br>61.300<br>60.691<br>60.318<br>59.138 | Dopamine D4 receptor<br>Dopamine D2 receptor<br>Dopamine D3 receptor<br>Alpha-2a adrenergic receptor<br>Serotonin 1a (5-HT1a) receptor | 99.193<br>62.014<br>25.692<br>15.274<br>13.511 |
| 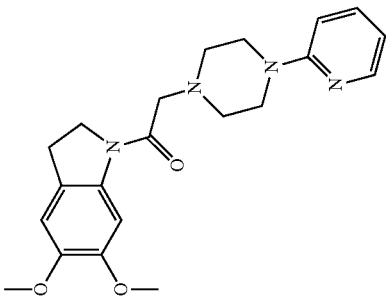 6_105 | 1 | IntraCNS: 0.3022<br>IntraNonCNS: 0.5962<br>OralCNS: 0.2021<br>OralNonCNS: 0.3857 | 102 | 48.856 | Dopamine D4 receptor<br>Dopamine D2 receptor<br>Alpha-1b adrenergic receptor<br>Alpha-1d adrenergic receptor<br>Alpha-1a adrenergic receptor | 89.974<br>61.139<br>54.336<br>53.900<br>52.634 | Dopamine D4 receptor<br>Dopamine D2 receptor<br>Dopamine D3 receptor<br>Cytochrome P450 1A2<br>Multidrug resistance-associated protein 1 | 94.130<br>62.130<br>32.173<br>30.064<br>17.502 |

TABLE 8-continued

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 6_110 | 2 | IntraCNS: 0.5038 IntraNonCNS: 0.4436 OralCNS: 0.3137 OralNonCNS: 0.1654 | 102 | 48.206 | Dopamine D4 receptor Alpha-1b adrenergic receptor Alpha-1d adrenergic receptor Dopamine D2 receptor Alpha-1a adrenergic receptor | 93.091 63.175 62.702 62.196 61.119 | Dopamine D4 receptor Dopamine D2 receptor Serotonin 7 (5-HT7) receptor Dopamine D3 receptor Sigma opioid receptor | 93.741 60.341 28.607 27.852 25.200 |
| 6_195 | 2 | IntraCNS: 0.09261 IntraNonCNS: 0.5541 OralCNS: 0.07287 OralNonCNS: 0.4279 | 100 | 50.377 | Dopamine D4 receptor Alpha-1b adrenergic receptor Alpha-1d adrenergic receptor Alpha-1a adrenergic receptor Dopamine D2 receptor | 69.240 37.294 36.236 35.369 34.637 | Dopamine D4 receptor Dopamine D2 receptor Sigma-1 receptor Voltage-gated L-type calcium channel alpha-1F subunit Glysine transporter 2 | 74.481 35.252 8.6011 7.1841 7.0327 |

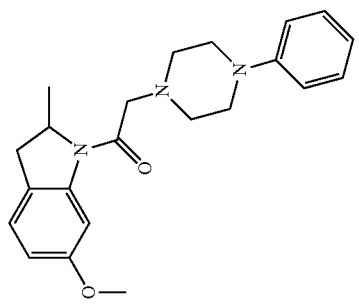

6_110

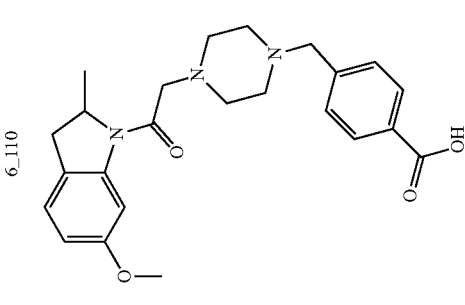

6_195

TABLE 8-continued

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 6_326 | 2 | IntraCNS: 0.2479 IntraNonCNS: 0.5544 OralCNS: 0.1674 OralNonCNS: 0.3533 | 97 | 53.718 | Dopamine D4 receptor Dopamine D2 receptor Dopamine D3 receptor Cytochrome P450 3A4 Alpha-1b adrenergic receptor | 83.136 54.749 40.910 20.934 18.867 | Dopamine D4 receptor Dopamine D3 receptor Dopamine D2 receptor Serotonin 7 (5-HT7) receptor Cytochrome P450 3A4 | 89.145 48.988 25.096 17.271 14.693 |
| 6_347 | 2 | IntraCNS: 0.2996 IntraNonCNS: 0.5929 OralCNS: 0.1991 OralNonCNS: 0.3812 | 96 | 54.438 | Dopamine D4 receptor Dopamine D2 receptor Alpha-1b adrenergic receptor Alpha-1d adrenergic receptor Alpha-1a adrenergic receptor | 83.481 55.234 50.881 50.537 49.170 | Dopamine D4 receptor Dopamine D2 receptor Serotonin 1a (5-HT1a) receptor Cytochrome P450 1A2 | 87.876 56.354 30.921 16.984 16.195 |

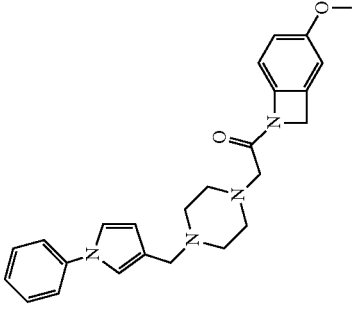

6_326

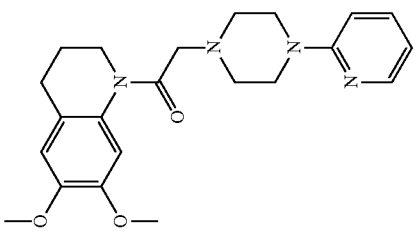

6_347

TABLE 8-continued

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 6_1306 | 1 | IntraCNS: 0.2335<br>IntraNonCNS: 0.611<br>OralCNS: 0.1544<br>OralNonCNS: 0.3852 | 91 | 60.236 | Dopamine D4 receptor<br>Dopamine D2 receptor<br>Alpha-1b adrenergic receptor<br>Alpha-1d adrenergic receptor<br>Alpha-1a adrenergic receptor | 77.393<br>46.453<br>43.489<br>42.358<br>41.007 | Dopamine D4 receptor<br>Dopamine D2 receptor<br>Sigma opioid receptor<br>Muscarinic acetylcholine receptor M3<br>Voltage-gated T-type calcium channel alpha-1G subunit | 80.996<br>45.508<br>28.574<br>22.322<br>19.363 |
| 6_1227 | 1 | IntraCNS: 0.2306<br>IntraNonCNS: 0.6034<br>OralCNS: 0.1511<br>OralNonCNS: 0.3781 | 91 | 59.799 | Dopamine D4 receptor<br>Dopamine D2 receptor<br>Alpha-1b adrenergic receptor<br>Alpha-1d adrenergic receptor<br>Alpha-1a adrenergic receptor | 77.842<br>46.770<br>44.836<br>43.720<br>42.412 | Dopamine D4 receptor<br>Dopamine D2 receptor<br>Sigma opioid receptor<br>Muscarinic acetylcholine receptor M3<br>Voltage-gated T-type calcium channel alpha-1G subunit | 81.378<br>46.449<br>28.703<br>22.463<br>19.383 |

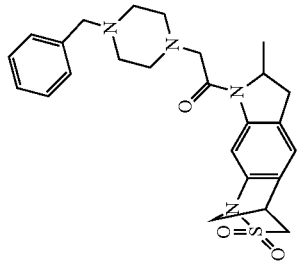

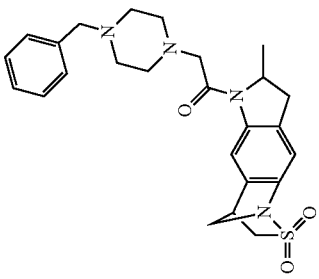

TABLE 8-continued

Predicted data parameters for 15 virtual molecules on the first Pareto front of the population optimised in the dopamine D4 activity model

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| | 1 | IntraCNS: 0.1981<br>IntraNonCNS: 0.6268<br>OralCNS: 0.1339<br>OralNonCNS: 0.4097 | 90 | 61.653 | Dopamine D4 receptor<br>Dopamine D2 receptor<br>Dopamine D3 receptor<br>Alpha-1b adrenergic receptor<br>Alpha-1d adrenergic receptor | 78.697<br>56.558<br>37.199<br>20.079<br>19.223 | Dopamine D4 receptor<br>Dopamine D3 receptor<br>Dopamine D2 receptor<br>Cytochrome P450 3A4<br>Serotonin 7 (5-HT7) receptor | 78.972<br>40.185<br>23.535<br>17.047<br>13.150 |

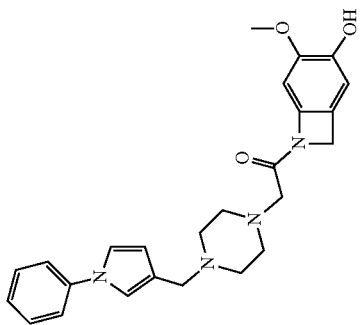

6_1692

TABLE 9

Prioritized compounds STI-0018541 and STI-0018538 selected for experimental determination of receptor binding activity

| Molecule | ParetoFront | ScoreD | Dopamine D4 | Vector Distance (D4 = 140, ADME = 50) | SideEff_AllCpds | SideEffScore_AllCpds | SideEff_HighConfidence | SideEffScore_HighConfidence |
|---|---|---|---|---|---|---|---|---|
| 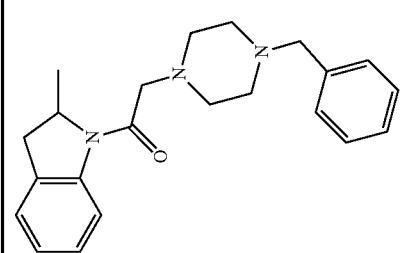 STI-0018638 | 1 | IntraCNS: 0.2941<br>IntraNonCNS: 0.3348<br>OralCNS: 0.1931<br>OralNonCNS: 0.2198 | 122 | 32.132 | Dopamine D4 receptor<br>Dopamine D2 receptor<br>Alpha-1b adrenergic receptor<br>Alpha-1d adrenergic receptor<br>Alpha-1a adrenergic receptor | 109.34<br>69.356<br>64.376<br>63.186<br>61.775 | Dopamine D4 receptor<br>Dopamine D2 receptor<br>Sigma opioid receptor<br>Tripeptidyl aminopeptidase<br>Muscarinic acetylcholine receptor M3 | 113.05<br>68.085<br>28.964<br>25.603<br>22.679 |
| 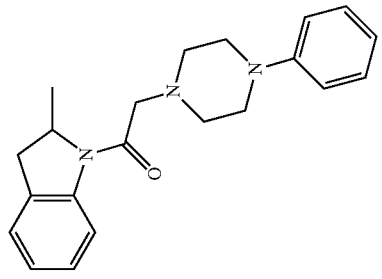 STI-0018641 | 1 | IntraCNS: 0.4859<br>IntraNonCNS: 0.4296<br>OralCNS: 0.305<br>OralNonCNS: 0.2697 | 120 | 30.525 | Dopamine D4 receptor<br>Alpha-1b adrenergic receptor<br>Alpha-1d adrenergic receptor<br>Alpha-1a adrenergic receptor<br>Dopamine D2 receptor | 111.40<br>78.039<br>77.379<br>75.630<br>75.396 | Dopamine D4 receptor<br>Dopamine D2 receptor<br>Tripeptidyl aminopeptidase<br>Serotonin 7 (5-HT7) receptor<br>Voltage-gated T-type calcium channel alpha-1G subunit | 111.87<br>73.205<br>28.276<br>26.928<br>23.279 |

Prioritisation of Optimisation Results: Dopamine D2 Optimisation

For each compound two method ranking scores were calculated: a Pareto front and a Vector Distance to a defined Achievement Objective. The Achievement Objective was defined as a Bayesian D2 Score of 100 and a normalised (ADME ScoreMax×100) ADME score of 50.

Figure 14:
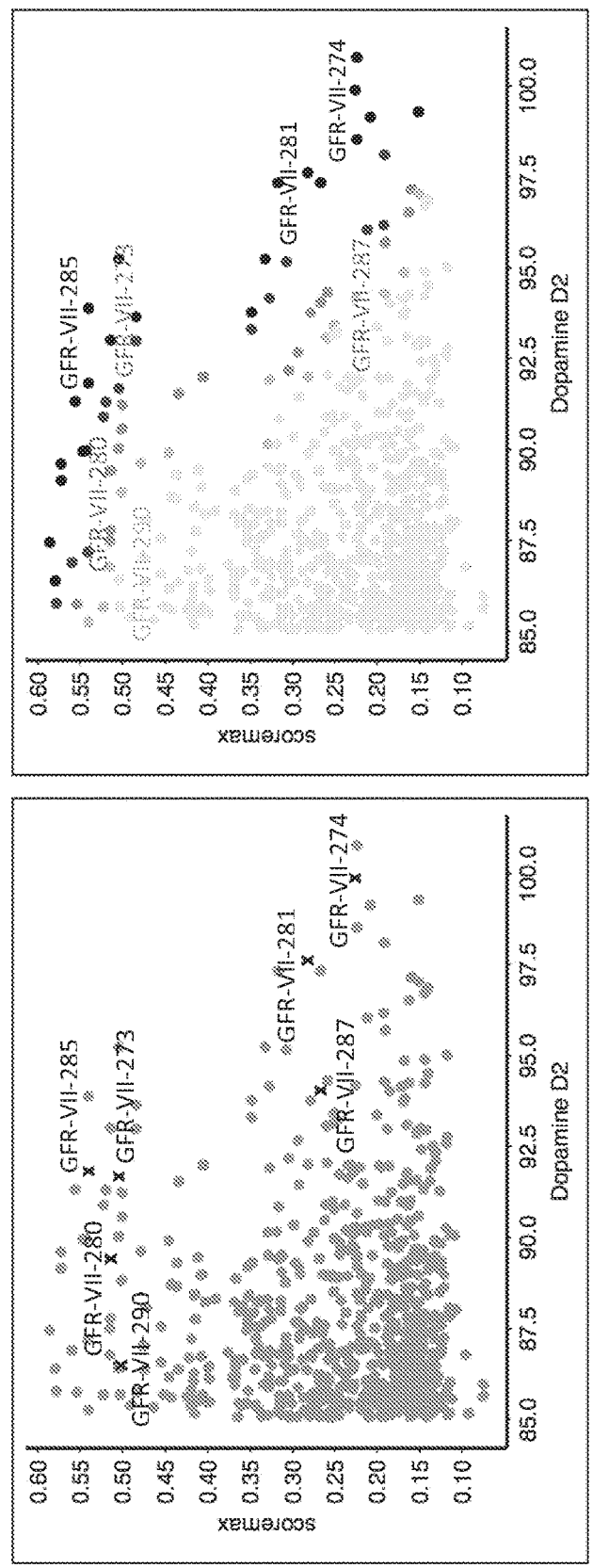
FIG. 14 shows the optimisation of compounds for binding to dopamine D2 (A). Bayesian score for predicted dopamine D2 activity (x-axis) and maximum predicted ADME score, normalised (y-axis). The 7 compounds selected for experimental evaluation are identified: GFR-VII-274, GFR-VII-281, GFR-VII-285, GFR-VII-273, GFR-VII-287, GFR-VII-280 and GFR-VII-290. (B) The same dataset as in FIG. 14(A) with molecules of each Pareto front identified by colour. The first Pareto front (Pareto Front=1) is coloured black; the second Pareto front (Pareto Front=2) is coloured dark grey; and third Pareto front (Pareto Front=3) is coloured light grey.

The results are shown in the Tables 10 and 11 and FIG. 14. Since the acetylcholinesterase activity was not selected for, the predicted activity against the original target decreased through each subsequent generation of compounds while predicted dopamine D2 activity tended to increase for individuals in the populations.

FIG. 14(A) shows the entire final population of 10,000 compounds generated by the optimisation of donepezil against the Dopamine D2 objective and the ADME objective. The x-axis represents the Bayesian score for predicted Dopamine D2 activity and the y-axis represents the maximum predicted ADME, normalised. The higher the score in each prediction, the higher the predicted likelihood of compounds having good dopamine D2 receptor binding activity and/or good pharmacokinetic properties, respectively. Based on the predicted activities 7 compounds (coloured black) and indicated by an "X" were selected for experimental testing. All 7 compounds belonged to the isoindolinone class. The same dataset is shown in FIG. 14(B) except the compounds on each of the first three Pareto fronts are identified: first Pareto front (black); second Pareto front (dark grey); and third Pareto front (light grey). In FIG. 14(B) the 7 compounds selected for experimental testing are labelled accordingly by their corresponding Pareto Front colour.

Table 10 shows the data for the twelve compounds prioritised in the first Pareto front of molecules optimised from donepezil against the dopamine D2/ADME achievement objectives. The vector distance of each molecule to the first achievement objective (D2=100, ADME=50) is listed. In addition to vector distance, the dopamine D2 activity is indicated in the corresponding column and the predicted activity for other targets for each compound are listed in the 'Side Effects' column with their corresponding Bayesian Model score. The Bayesian models marked as High Confidence are those for which there is an unambiguous assignment of the compounds to molecular target in the original literature from which the data was derived. The All Compound models are constructed from all the activity data points assigned to that target, including data where the exact molecular target assignment may be ambiguous, in the original literature.

Data for the 12 prioritised dopamine D2 antagonists optimised from donepezil are reported in Table 11. The compounds are ordered according to predicted dopamine D2 Bayesian activity scores, with the highest scoring compound listed first. The vector distance to the first Achievement Objective (D2=100, ADME=50) is also listed. As indicated, the 12 compounds with the shortest vector distances to the achievement objectives were located on the first and second Pareto fronts. In addition to the objective dopamine D2 activity, the predicted activity for other targets for each compound are listed in the 'Side Effects' column with their corresponding Bayesian Model score.

The seven prioritised compounds selected for experimental determination of receptor binding are displayed in Table 12. These compounds include three compounds on the first Pareto front (GFR-VII-274, GFR-VII-281, and GFR-VII-285) and the top two compounds with the shortest vector distances (GFR-VII-273 and GFR-VII-285) to the achievement objective. The remaining compounds GFR-VII-287, GFR-VII-280 and GFR-VII-290 were synthesised as they are close analogues of the two prioritised compounds on the basis of vector distance.

TABLE 10

Predicted data for 12 compounds on the first Pareto front of the population optimised in the dopamine D2 activity model

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| 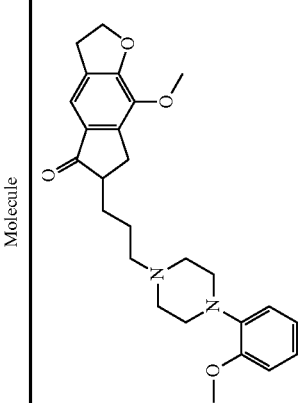<br>StarDropID 2430 | 1 | IntraCNS: 0.08958<br>IntraNonCNS: 0.2237<br>OralCNS: 0.05404<br>OralNonCNS: 0.1273 | 101 | 27.692 | Serotonin 1a (5-HT1a) receptor<br>Alpha-1b adrenergic receptor<br>Alpha-1d adrenergic receptor<br>Alpha-1a adrenergic receptor<br>Dopamine D2 receptor | 100.58<br>94.370<br>94.097<br>92.910<br>87.008 | Serotonin 1a (5-HT1a) receptor<br>Dopamine D2 receptor<br>Alpha-1b adrenergic receptor<br>Alpha-1a adrenergic receptor<br>Dopamine D3 receptor | 95.468<br>82.579<br>68.733<br>64.547<br>62.287 |
| 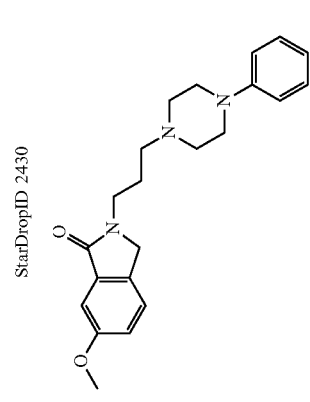<br>GFR-VII-274 | 1 | IntraCNS: 0.177<br>IntraNonCNS: 0.2258<br>OralCNS: 0.112<br>OralNonCNS: 0.1428 | 100 | 27.420 | Dopamine D2 receptor<br>Dopamine D3 receptor<br>Serotonin 1a (5-HT1a) receptor<br>Serotonin 2c (5-HT2c) receptor<br>Serotonin 2b (5-HT2b) receptor | 94.366<br>92.060<br>88.468<br>81.778<br>80.056 | Dopamine D2 receptor<br>Dopamine D3 receptor<br>Serotonin 1a (5-HT1a) receptor<br>Dopamine D4 receptor<br>Serotonin 2a (5-HT2a) receptor | 90.181<br>83.590<br>82.241<br>64.544<br>56.099 |
| 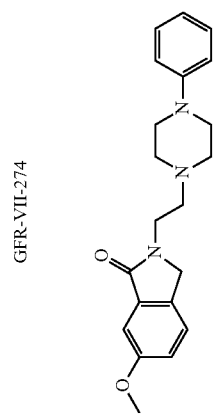<br>GFR-VII-281 | 1 | IntraCNS: 0.2209<br>IntraNonCNS: 0.2818<br>OralCNS: 0.1412<br>OralNonCNS: 0.1801 | 98 | 21.951 | Dopamine D2 receptor<br>Dopamine D3 receptor<br>Serotonin 1a (5-HT1a) receptor<br>Serotonin 2c (5-HT2c) receptor<br>Serotonin 2b (5-HT2b) receptor | 91.896<br>88.105<br>82.946<br>80.692<br>77.988 | Dopamine D2 receptor<br>Dopamine D3 receptor<br>Serotonin 1a (5-HT1a) receptor<br>Dopamine D4 receptor<br>Serotonin 2c (5-HT2c) receptor | 88.367<br>82.157<br>76.507<br>67.248<br>55.245 |

TABLE 10-continued

Predicted data for 12 compounds on the first Pareto front of the population optimised in the dopamine D2 activity model

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| StarDropID 1135 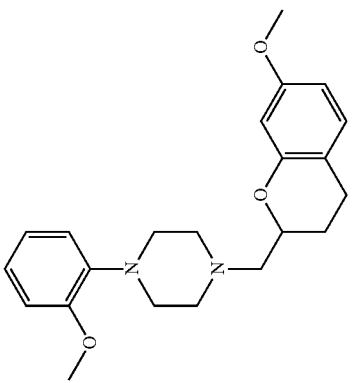 | 1 | IntraCNS: 0.2786<br>IntraNonCNS: 0.3175<br>OralCNS: 0.1711<br>OralNonCNS: 0.1168 | 97 | 19.236 | Serotonin 1a (5-HT1a) receptor<br>Alpha-1b adrenergic receptor<br>Alpha-1d adrenergic receptor<br>Alpha-1a adrenergic receptor<br>Dopamine D2 receptor | 100.80<br>96.764<br>96.472<br>95.503<br>92.225 | Serotonin 1a (5-HT1a) receptor<br>Dopamine D2 receptor<br>Dopamine D3 receptor<br>Dopamine D4 receptor<br>Alpha-1b adrenergic receptor | 94.122<br>90.621<br>63.428<br>58.849<br>57.556 |
| StarDropID 962 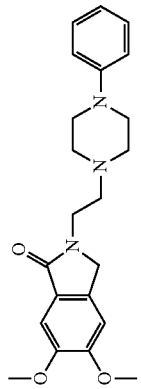 | 1 | IntraCNS: 0.1313<br>IntraNonCNS: 0.3326<br>OralCNS: 0.08423<br>OralNonCNS: 0.2013 | 95 | 18.653 | Dopamine D3 receptor<br>Dopamine D2 receptor<br>Alpha-1d adrenergic receptor<br>Alpha-1b adrenergic receptor<br>Alpha-1a adrenergic receptor | 88.015<br>85.432<br>77.784<br>77.448<br>76.007 | Dopamine D3 receptor<br>Dopamine D2 receptor<br>Dopamine D4 receptor<br>Serotonin 1a (5-HT1a) receptor<br>Serotonin 2c (5-HT2c) receptor | 86.820<br>82.506<br>63.656<br>62.581<br>53.491 |

TABLE 10-continued

Predicted data for 12 compounds on the first Pareto front of the population optimised in the dopamine D2 activity model

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| StarDropID 814 | 1 | IntraCNS: 0.1347<br>IntraNonCNS: 0.3487<br>OralCNS: 0.07791<br>OralNonCNS: 0.1903 | 94 | 17.690 | Alpha-1b adrenergic receptor<br>Alpha-1d adrenergic receptor<br>Alpha-1a adrenergic receptor<br>Serotonin 1a (5-HT1a) receptor<br>Alpha-2b adrenergic receptor | 94.785<br>94.437<br>93.738<br>84.421<br>81.306 | Serotonin 1a (5-HT1a) receptor<br>Dopamine D2 receptor<br>Alpha-1a adrenergic receptor<br>Alpha-1b adrenergic receptor<br>Alpha-1d adrenergic receptor | 79.137<br>76.615<br>72.597<br>71.565<br>70.640 |
| StarDropID 103 | 1 | IntraCNS: 0.4474<br>IntraNonCNS: 0.4839<br>OralCNS: 0.2855<br>OralNonCNS: 0.1849 | 94 | 10.238 | Serotonin 1a (5-HT1a) receptor<br>Alpha-1b adrenergic receptor<br>Alpha-1a adrenergic receptor<br>Alpha-1d adrenergic receptor<br>Serotonin 2b (5-HT2b) receptor | 99.306<br>87.888<br>87.633<br>87.614<br>83.427 | Serotonin 1a (5-HT1a) receptor<br>Dopamine D2 receptor<br>Alpha-1a adrenergic receptor<br>Alpha-1b adrenergic receptor<br>Alpha-1d adrenergic receptor | 94.919<br>78.325<br>70.892<br>66.370<br>65.866 |
| StarDropID 102 | 1 | IntraCNS: 0.4461<br>IntraNonCNS: 0.484<br>OralCNS: 0.2846<br>OralNonCNS: 0.1849 | 93 | 10.889 | Serotonin 1a (5-HT1a) receptor<br>Alpha-1b adrenergic receptor<br>Alpha-1d adrenergic receptor<br>Alpha-1a adrenergic receptor<br>Serotonin 2b (5-HT2b) receptor | 100.07<br>88.291<br>88.012<br>87.730<br>83.248 | Serotonin 1a (5-HT1a) receptor<br>Dopamine D2 receptor<br>Alpha-1a adrenergic receptor<br>Alpha-1b adrenergic receptor<br>Alpha-1d adrenergic receptor | 94.330<br>77.641<br>71.004<br>66.838<br>66.294 |

TABLE 10-continued

Predicted data for 12 compounds on the first Pareto front of the population optimised in the dopamine D2 activity model

| Molecule | ParetoFront | ScoreD | Dopa- mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| GfR-VII-285 | 1 | IntraCNS: 0.1903 IntraNonCNS: 0.54 OralCNS: 0.1187 OralNonCNS: 0.3367 | 92 | 9.1057 | Serotonin 1a (5-HT1a) receptor Alpha-1d adrenergic receptor Alpha-1b adrenergic receptor Alpha-1a adrenergic receptor Dopamine D2 receptor | 87.827 86.489 86.452 85.725 84.498 | Serotonin 1a (5-HT1a) receptor Dopamine D2 receptor Alpha-1a adrenergic receptor Dopamine D3 receptor Alpha-1d adrenergic receptor | 81.784 80.236 78.596 77.629 74.185 |
| StarDropID 23 | 1 | IntraCNS: 0.2045 IntraNonCNS: 0.5559 OralCNS: 0.1275 OralNonCNS: 0.3353 | 91 | 12.784 | Alpha-1b adrenergic receptor Alpha-1d adrenergic receptor Alpha-1a adrenergic receptor Serotonin 7 (5-HT7) receptor Serotonin 1a (5-HT1a) receptor | 89.538 89.508 88.672 80.790 79.727 | Dopamine D3 receptor Alpha-1a adrenergic receptor Dopamine D2 receptor Alpha-1d adrenergic receptor Serotonin 1a (5-HT1a) receptor | 79.689 78.960 78.834 74.884 72.890 |

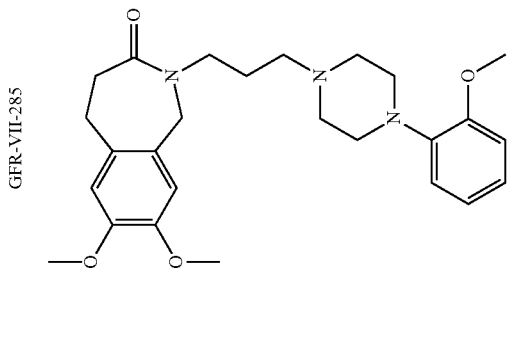

TABLE 10-continued

Predicted data for 12 compounds on the first Pareto front of the population optimised in the dopamine D2 activity model

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| StarDropID 15 | 1 | IntraCNS: 0.2106<br>IntraNonCNS: 0.5725<br>OralCNS: 0.1324<br>OralNonCNS: 0.348 | 90 | 15.072 | Alpha-1d adrenergic receptor<br>Alpha-1b adrenergic receptor<br>Alpha-1a adrenergic receptor<br>Dopamine D2 receptor<br>Dopamine D3 receptor | 88.236<br>87.918<br>86.775<br>78.472<br>76.593 | Alpha-1a adrenergic receptor<br>Alpha-1d adrenergic receptor<br>Dopamine D3 receptor<br>Dopamine D2 receptor<br>Alpha-1b adrenergic receptor | 80.178<br>78.977<br>78.204<br>77.561<br>71.989 |
| StarDropID 10 | 1 | IntraCNS: 0.2155<br>IntraNonCNS: 0.5858<br>OralCNS: 0.1367<br>OralNonCNS: 0.3594 | 87 | 17.611 | Alpha-1d adrenergic receptor<br>Alpha-1b adrenergic receptor<br>Alpha-1a adrenergic receptor<br>Dopamine D2 receptor<br>Dopamine D3 receptor | 84.904<br>84.668<br>83.499<br>77.269<br>75.866 | Dopamine D3 receptor<br>Alpha-1a adrenergic receptor<br>Dopamine D2 receptor<br>Alpha-1d adrenergic receptor<br>Alpha-1b adrenergic receptor | 76.525<br>76.337<br>76.106<br>74.894<br>69.051 |

TABLE 11

Predicted data for the 12 prioritised dopamine D2 antagonists listed according to predicted activity

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| 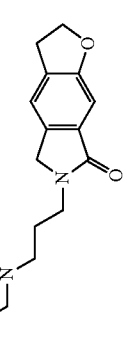 StarDropID 103 | 1 | IntraCNS: 0.4474 IntraNonCNS: 0.4839 OralCNS: 0.2855 OralNonCNS: 0.1849 | 94 | 10.238 | Serotonin 1a (5-HT1a) receptor Alpha-1b adrenergic receptor Alpha-1a adrenergic receptor Alpha-1d adrenergic receptor Serotonin 2b (5-HT2b) receptor | 99.306 87.888 87.633 87.614 83.427 | Serotonin 1a (5-HT1a) receptor Dopamine D2 receptor Alpha-1a adrenergic receptor Alpha-1b adrenergic receptor Alpha-1d adrenergic receptor | 94.919 78.325 70.892 66.370 65.866 |
| 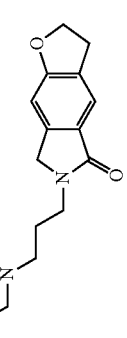 StarDropID 102 | 1 | IntraCNS: 0.4461 IntraNonCNS: 0.484 OralCNS: 0.2846 OralNonCNS: 0.1849 | 93 | 10.889 | Serotonin 1a (5-HT1a) receptor Alpha-1b adrenergic receptor Alpha-1d adrenergic receptor Alpha-1a adrenergic receptor Serotonin 2b (5-HT2b) receptor | 100.07 88.291 88.012 87.730 83.248 | Serotonin 1a (5-HT1a) receptor Dopamine D2 receptor Alpha-1a adrenergic receptor Alpha-1b adrenergic receptor Alpha-1d adrenergic receptor | 94.330 77.641 71.004 66.838 66.294 |

TABLE 11-continued

Predicted data for the 12 prioritised dopamine D2 antagonists listed according to predicted activity

| Molecule | ParetoFront | ScoreD | Dopa- mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| 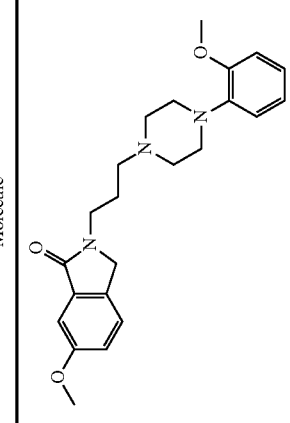<br>GFR-VII-273 | 2 | IntraCNS: 0.4886<br>IntraNonCNS: 0.5043<br>OralCNS: 0.3132<br>OralNonCNS: 0.3232 | 92 | 8.3358 | Serotonin 1a (5-HT1a) receptor<br>Alpha-1b adrenergic receptor<br>Alpha-1d adrenergic receptor<br>Dopamine D2 receptor<br>Alpha-1a adrenergic receptor | 97.115<br>85.469<br>85.316<br>84.906<br>84.657 | Serotonin 1a (5-HT1a) receptor<br>Dopamine D2 receptor<br>Serotonin 7 (5-HT7) receptor<br>Alpha-1a adrenergic receptor<br>Dopamine D3 receptor | 93.360<br>81.601<br>69.644<br>68.813<br>66.101 |
| 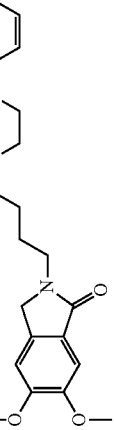<br>GFR-VII-285 | 1 | IntraCNS: 0.1903<br>IntraNonCNS: 0.54<br>OralCNS: 0.1187<br>OralNonCNS: 0.3367 | 92 | 9.1057 | Serotonin 1a (5-HT1a) receptor<br>Alpha-1d adrenergic receptor<br>Alpha-1b adrenergic receptor<br>Alpha-1a adrenergic receptor<br>Dopamine D2 receptor | 87.827<br>86.489<br>86.452<br>85.725<br>84.498 | Serotonin 1a (5-HT1a) receptor<br>Dopamine D2 receptor<br>Alpha-1a adrenergic receptor<br>Dopamine D3 receptor<br>Alpha-1d adrenergic receptor | 81.784<br>80.236<br>78.596<br>77.629<br>74.185 |
| 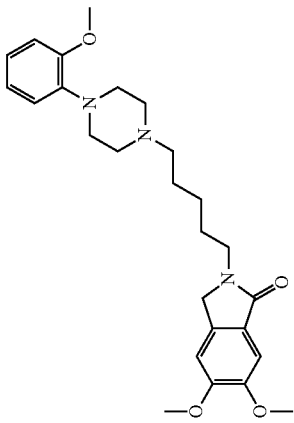<br>StarDropID 342 | 2 | IntraCNS: 0.1419<br>IntraNonCNS: 0.4054<br>OralCNS: 0.08821<br>OralNonCNS: 0.2438 | 92 | 13.820 | Alpha-1b adrenergic receptor<br>Alpha-1d adrenergic receptor<br>Serotonin 1a (5-HT1a) receptor<br>Alpha-1a adrenergic receptor<br>Alpha-2c adrenergic receptor | 86.075<br>85.994<br>85.029<br>84.987<br>84.779 | Alpha-1a adrenergic receptor<br>Serotonin 1a (5-HT1a) receptor<br>Dopamine D2 receptor<br>Alpha-1d adrenergic receptor<br>Dopamine D3 receptor | 79.950<br>79.569<br>79.427<br>76.516<br>74.739 |

TABLE 11-continued

Predicted data for the 12 prioritised dopamine D2 antagonists listed according to predicted activity

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| 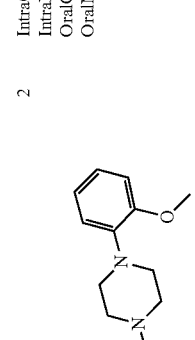 StarDropID 55 | 2 | IntraCNS: 0.179 IntraNonCNS: 05195. OralCNS: 0.1112 OralNonCNS: 0.3123 | 91 | 11.674 | Alpha-1d adrenergic receptor Alpha-1b adrenergic receptor Alpha-1a adrenergic receptor Serotonin 1a (5-HT1a) receptor Serotonin 2b (5-HT2b) receptor | 91.158 91.089 90.850 85.610 80.385 | Alpha-1a adrenergic receptor Alpha-1d adrenergic receptor Serotonin 1a (5-HT1a) receptor Dopamine D2 receptor Alpha-1b adrenergic receptor | 84.409 79.496 78.577 77.224 69.776 |
| 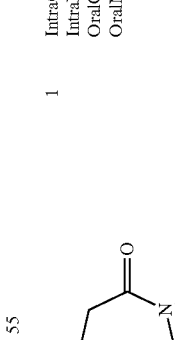 StarDropID 23 | 1 | IntraCNS: 0.2045 IntraNonCNS: 0.5559 OralCNS: 0.1275 OralNonCNS: 0.3353 | 91 | 12.784 | Alpha-1b adrenergic receptor Alpha-1d adrenergic receptor Alpha-1a adrenergic receptor Serotonin 7 (5-HT7) receptor Serotonin 1a (5-HT1a) receptor | 89.538 89.508 88.672 80.790 79.727 | Dopamine D3 receptor Alpha-1a adrenergic receptor Dopamine D2 receptor Alpha-1d adrenergic receptor Serotonin 1a (5-HT1a) receptor | 79.689 78.960 78.834 74.884 72.890 |

TABLE 11-continued

Predicted data for the 12 prioritised dopamine D2 antagonists listed according to predicted activity

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| StarDropID 51 | 2 | IntraCNS: 0.2541<br>IntraNonCNS: 0.5224<br>OralCNS: 0.1648<br>OralNonCNS: 0.3196 | 91 | 12.788 | Serotonin 1a (5-HT1a) receptor<br>Dopamine D2 receptor<br>Alpha-1b adrenergic receptor<br>Alpha-1d adrenergic receptor<br>Alpha-1a adrenergic receptor | 86.994<br>81.004<br>77.431<br>76.799<br>76.260 | Serotonin 1a (5-HT1a) receptor<br>Dopamine D2 receptor<br>Serotonin 7 (5-HT7) receptor<br>Alpha-1a adrenergic receptor<br>Alpha-1d adrenergic receptor | 84.485<br>74.159<br>70.738<br>61.885<br>57.894 |
| StarDropID 35 | 2 | IntraCNS: 0.1903<br>IntraNonCNS: 0.543<br>OralCNS: 0.1187<br>OralNonCNS: 0.3277 | 90 | 13.548 | Alpha-1d adrenergic receptor<br>Alpha-1b adrenergic receptor<br>Alpha-1a adrenergic receptor<br>Serotonin 1a (5-HT1a) receptor<br>Dopamine D2 receptor | 90.945<br>90.529<br>90.008<br>81.512<br>80.003 | Alpha-1a adrenergic receptor<br>Alpha-1d adrenergic receptor<br>Dopamine D2 receptor<br>Serotonin 1a (5-HT1a) receptor<br>Alpha-1b adrenergic receptor | 86.286<br>84.252<br>76.936<br>73.899<br>70.076 |

TABLE 11-continued

Predicted data for the 12 prioritised dopamine D2 antagonists listed according to predicted activity

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| StarDropID 29 | 2 | IntraCNS: 0.2047 IntraNonCNS: 0.5469 OralCNS: 0.1279 OralNonCNS: 0.3306 | 90 | 13.709 | Alpha-1b adrenergic receptor Alpha-1d adrenergic receptor Alpha-1a adrenergic receptor Serotonin 7 (5-HT7) receptor Dopamine D3 receptor | 94.926 94.799 93.759 87.574 80.260 | Serotonin 1a (5-HT1a) receptor Alpha-1a adrenergic receptor Dopamine D3 receptor Dopamine D2 receptor Alpha-1d adrenergic receptor | 79.185 78.926 76.784 76.453 75.058 |
| StarDropID 15 | 1 | IntraCNS: 0.2106 IntraNonCNS: 0.5725 OralCNS: 0.1324 OralNonCNS: 0.348 | 90 | 15.072 | Alpha-1d adrenergic receptor Alpha-1b adrenergic receptor Alpha-1a adrenergic receptor Dopamine D2 receptor Dopamine D3 receptor | 88.236 87.918 86.775 78.472 76.593 | Alpha-1a adrenergic receptor Alpha-1d adrenergic receptor Dopamine D3 receptor Dopamine D2 receptor Alpha-1b adrenergic receptor | 80.178 78.977 78.204 77.561 71.989 |

TABLE 11-continued

Predicted data for the 12 prioritised dopamine D2 antagonists listed according to predicted activity

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| StarDropID 16 | 2 | IntraCNS: 0.2105<br>IntraNonCNS: 0.5722<br>OralCNS: 0.1319<br>OralNonCNS: 0.3468 | 89 | 15.476 | Alpha-1b adrenergic receptor<br>Alpha-1d adrenergic receptor<br>Alpha-1a adrenergic receptor<br>Dopamine D3 receptor<br>Serotonin 1a (5-HT1a) receptor | 86.274<br>86.162<br>85.381<br>79.006<br>78.566 | Dopamine D3 receptor<br>Dopamine D2 receptor<br>Alpha-1a adrenergic receptor<br>Serotonin 1a (5-HT1a) receptor<br>Alpha-1d adrenergic receptor | 78.695<br>77.349<br>75.111<br>73.197<br>70.793 |

TABLE 12

Seven compounds selected for experimental determination of dopamine D2 receptor binding

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| 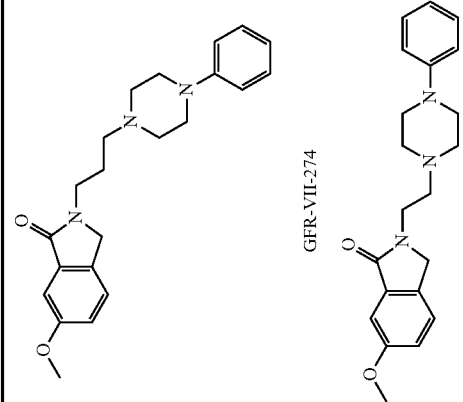<br>GFR-VII-274 | 1 | IntraCNS: 0.177<br>IntraNonCNS: 0.2258<br>OralCNS: 0.112<br>OralNonCNS: 0.1428 | 100 | 27.420 | Dopamine D2 receptor<br>Dopamine D3 receptor<br>Serotonin 1a (5-HT1a) receptor<br>Serotonin 2c (5-HT2c) receptor<br>Serotonin 2b (5-HT2b) receptor | 94.366<br>92.060<br>88.468<br>81.778<br>80.056 | Dopamine D2 receptor<br>Dopamine D3 receptor<br>Serotonin 1a (5-HT1a) receptor<br>Dopamine D4 receptor<br>Serotonin 2a (5-HT2a) receptor | 90.181<br>83.590<br>82.241<br>64.544<br>56.099 |
| 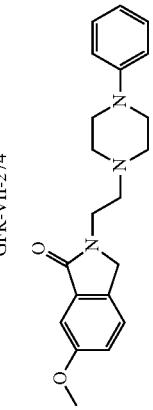<br>GFR-VII-281 | 1 | IntraCNS: 0.2209<br>IntraNonCNS: 0.2818<br>OralCNS: 0.1412<br>OralNonCNS: 0.1801 | 98 | 21.951 | Dopamine D2 receptor<br>Dopamine D3 receptor<br>Serotonin 1a (5-HT1a) receptor<br>Serotonin 2c (5-HT2c) receptor<br>Serotonin 2b (5-HT2b) receptor | 91.896<br>88.105<br>82.946<br>80.692<br>77.988 | Dopamine D2 receptor<br>Dopamine D3 receptor<br>Serotonin 1a (5-HT1a) receptor<br>Dopamine D4 receptor<br>Serotonin 2c (5-HT2c) receptor | 88.367<br>82.157<br>76.507<br>67.248<br>55.245 |

TABLE 12-continued

Seven compounds selected for experimental determination of dopamine D2 receptor binding

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| GFR-VII-287 | 3 | IntraCNS: 0.1052<br>IntraNonCNS: 0.2665<br>OralCNS: 0.06694<br>OralNonCNS: 0.1696 | 94 | 24.098 | Dopamine D2 receptor<br>Dopamine D3 receptor<br>Alpha-1b adrenergic receptor<br>Alpha-1d adrenergic receptor<br>Alpha-1a adrenergic receptor | 91.970<br>87.902<br>78.910<br>78.894<br>77.729 | Dopamine D3 receptor<br>Dopamine D2 receptor<br>Serotonin 1a (5-HT1a) receptor<br>Dopamine D4 receptor<br>Serotonin 2a (5-HT2a) receptor | 88.252<br>84.319<br>68.316<br>60.952<br>51.540 |
| GFR-VII-273 | 2 | IntraCNS: 0.4886<br>IntraNonCNS: 0.5043<br>OralCNS: 0.3132<br>OralNonCNS: 0.3232 | 92 | 8.3358 | Serotonin 1a (5-HT1a) receptor<br>Alpha-1b adrenergic receptor<br>Alpha-1d adrenergic receptor<br>Dopamine D2 receptor<br>Alpha-1a adrenergic receptor | 97.115<br>85.469<br>85.316<br>84.906<br>84.657 | Serotonin 1a (5-HT1a) receptor<br>Dopamine D2 receptor<br>Serotonin 7 (5-HT7) receptor<br>Alpha-1a adrenergic receptor<br>Dopamine D3 receptor | 93.360<br>81.601<br>69.644<br>68.813<br>66.101 |
| GFR-VII-285 | 1 | IntraCNS: 0.1903<br>IntraNonCNS: 0.54<br>OralCNS: 0.1187<br>OralNonCNS: 0.3367 | 92 | 9.1057 | Serotonin 1a (5-HT1a) receptor<br>Alpha-1d adrenergic receptor<br>Alpha-1b adrenergic receptor<br>Alpha-1a adrenergic receptor<br>Dopamine D2 receptor | 87.827<br>86.489<br>86.452<br>85.725<br>84.498 | Serotonin 1a (5-HT1a) receptor<br>Dopamine D2 receptor<br>Alpha-1a adrenergic receptor<br>Dopamine D3 receptor<br>Alpha-1d adrenergic receptor | 81.784<br>80.236<br>78.596<br>77.629<br>74.185 |

TABLE 12-continued

Seven compounds selected for experimental determination of dopamine D2 receptor binding

| Molecule | ParetoFront | ScoreD | Dopa-mineD2 | Vector Distance (D2 = 100, ADME = 50) | SideEff_AllCpds | SideEffScore_AllCpds | SideEff_HighConfidence | SideEffScore_HighConfidence |
|---|---|---|---|---|---|---|---|---|
| GFR-VII-280-HCl | 3 | IntraCNS: 0.5006<br>IntraNonCNS: 0.514<br>OralCNS: 0.3233<br>OralNonCNS: 0.332 | 89 | 10.689 | Serotonin 1a (5-HT1a) receptor<br>Alpha-1d adrenergic receptor<br>Alpha-1b adrenergic receptor<br>Alpha-1a adrenergic receptor<br>Dopamine D2 receptor | 91.593<br>84.206<br>84.007<br>82.934<br>82.436 | Serotonin 1a (5-HT1a) receptor<br>Dopamine D2 receptor<br>Alpha-1a adrenergic receptor<br>Alpha-1d adrenergic receptor<br>Dopamine D3 receptor | 87.625<br>79.787<br>70.080<br>69.259<br>64.668 |
| GFR-VII-290 | 5 | IntraCNS: 0.4839<br>IntraNonCNS: 0.5045<br>OralCNS: 0.3102<br>OralNonCNS: 0.3234 | 86 | 13.556 | Serotonin 2b (5-HT2b) receptor<br>Alpha-1d adrenergic receptor<br>Alpha-1b adrenergic receptor<br>Alpha-1a adrenergic receptor | 92.252<br>81.455<br>80.341<br>80.120<br>79.413 | Serotonin 1a (5-HT1a) receptor<br>Dopamine D2 receptor<br>Serotonin 7 (5-HT7) receptor<br>Alpha-1a adrenergic receptor<br>Dopamine D3 receptor | 88.545<br>76.244<br>69.436<br>68.227<br>67.286 |

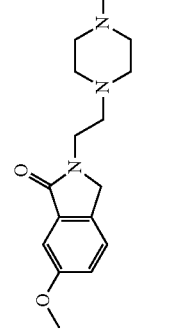

Experimental Confirmation of Predicted Results

This Example was designed to generate optimised new compounds with significant dopamine D2 binding affinity from the weak predicted dopamine receptor activity of the drug donepezil.

In agreement with the low predicted activity score (Dopamine D2 Bayesian Activity Score=9) donepezil displays a very weak affinity for the dopamine D2 receptor of only 18.6% inhibition, which was deemed too low to determine a Ki binding affinity. In contrast the evolved optimised compound 6_38 (GFR-VII-285) exhibits 96.2% inhibition of the dopamine D2 receptor and a binding affinity (or inhibition constant) of Ki=156 nM.

Furthermore, the system predicts that the biological profile of GFR-VII-285 will exhibit receptor binding to 5-HT-1A, Alpha1A, Alpha1B, Alpha1D and dopamine D1 receptors and, indeed, potent affinity for these receptors is also observed. Thus, the method of the invention is successful in evolving molecules having optimized dopamine D2 activity (i.e. with significantly higher affinity for the dopamine D2 receptor than the starting molecule. In addition, the method was also successful at correctly predicting the broader biological activity profile of the evolved virtual compounds.

In addition to optimising the activity of molecules against the dopamine D2 receptor, this Example further demonstrates the utility of the invention in generating and selecting molecules having optimised dopamine D4 receptor binding affinity, from a starting point of donepezil, which has weak predicted dopamine receptor activity. The measured binding affinities/inhibition constant of donepezil is 614 nM (Ki) for this target. To contrast with donepezil, two of the optimised dopamine D4 inhibiting compounds were selected for experimental profiling. Compound 6_1 (STT-00185638)—which exhibited the highest predicted dopamine D4 score—was ranked on the first Pareto front and had the third shortest distance to the achievement objective. This compound was found to be a potent and selective D4 antagonist, with a Ki=9.5 nM, which is a 65-fold increase in affinity over donepezil. The compound STT-00185641 appeared to be inactive as a dopamine D4 ligand. A summary of the actual binding profiles of selected optimised molecules in comparison to donepezil is displayed in Table 13.

TABLE 13

Summary of optimisation results of selected molecules

| Structure | Dopamine D2 & D4 Bayesian Score | Ki (nM) D2 D4 | Off Target Predictions | Off Target Ki (nM) |
|---|---|---|---|---|
| Donepezil | D2: 9.0<br>D4: 26.3 | D2: inactive<br>D4: 614 | Alpha1A: −5.7<br>Alpha1D: −8.5<br>D4: 26.3 | Alpha1A: 1463<br>Alpha1D: 1918<br>D4: 614 |
| STT-00185638 | D2: 67.7<br>D4: 112.1 | D2: 2457<br>D4: 9.5 | 5HT1A: −9.8<br>Alpha1A: −18.8<br>D1: 6.3 | 5HT1A: 7082<br>Alpha1A: 2057<br>D1: 6364 |
| GFR-VII-285 | D2: 79.4<br>D4: 52.3 | D2: 156<br>D4: 436 | 5HT1A: 81.7<br>Alpha1A: 78.6<br>Alpha1B: 66.4<br>Alpha1D: 74.6<br>D1: 47.4 | 5HT1A: 23<br>Alpha1A: 0.9<br>Alpha1B: 19.3<br>Alpha1D: 4.4<br>D1: 531 |

The primary and secondary radioligand assay results for donepezil and the isoindolinone series of compounds evolved as dopamine D2 antagonists (GFR-VII-266, GFR-VII-269, GFR-VII-273, GFR-VII-274, GFR-VII-280, GFR-VII-281, GFR-VII-285, GFR-VII-287, GFR-VII-290), and the 2,3-dihydro-indol-1-yl series evolved as dopamine D4 antagonist (STT-00185638 and STT-00185641) are shown in Table 14; and the predicted profiles for the screened compounds are shown in Tables 15 (biological activity) and 15 (ADME properties).

Table 14 shows the calculated primary and secondary radioligand binding assay results for the selected compounds. The compounds were tested for their activity profiles against the receptors: 5HT1a, Alpha1a, Alpha1b, Alpha1d, and dopamine D1, D2, D3, D4 and D5. In the primary radiobinding assay, percent inhibition of radioligand binding is calculated as a % inhibition=100%−% radioactivity bound. The radioligands used in the assays were: for 5HT-1a, [3H]8-OH-DPAT; for dopamine D1, [3H]SCH233930; for dopamine D2, [3H]N-methylspiperone; for dopamine D3, [H]N-methyispiperone; for dopamine D4, [H]N-methylspiperone; for dopamine D5, [3H]SCH233930; for Alpha 1A, [3H]Prazosin; for Alpha 1B, [3H]Prazosin; and for Alpha 1D, [3H]Prazosin. The secondary binding assays to determine the inhibition constant (K) was calculated by applying the Cheng-Prusoff approximation: Ki=IC50/(1+[ligand]/KD) where [ligand] equals the assay radioligand concentration and D equals the affinity constant of the radioligand for the target receptor. All compound receptor binding profiles and Ki determinations were generously provided by the National Institute of Mental Health's Psychoactive Drug Screening Program, Contract # HHSN-271-2008-00025-C(NIMH PDSP). Full details of the assay protocols are described in the NIMH PDSP Protocol Book, see for example, (http://pdsp.med.unc.edu/UNC-CH%20Protocol%20Book.pdf). The method used is briefly set out at the end of this Example.

In contrast with Table 14, Table 15 displays the predicted Bayesian activities of donepezil and the selected compounds for the receptors with the highest predicted activity, as above (5HT1a, Alpha1a, Alpha1b, Alpha1d, dopamine D1, D2, D03, D4 and D05). Similarly, Table 16 indicates the ADME predictions for donepezil and the selected compounds against a range of pharmcokinetic profiles. ADME scores were calculated using Stardrop by Optibrium Ltd, as previously described.

All of the selected evolved dopamine D2 compounds exhibited significantly improved binding affinity for dopamine D2 receptor compared to donepezil, the starting structure. In general the predicted 'off-target' profiles of 5-HT1A, Alpha1A, Alpha1B, Alpha1D and dopamine D4 were also confirmed by experiment. Significantly, the predicted dopamine D4 antagonist STT-00185638 exhibited potent affinity for dopamine D4 receptor with low affinities for other receptors, assayed.

Examples of the structural evolution of donepezil from an acetylcholinesterase inhibitor into a dopamine D2 (GFR-VII-285) or a dopamine D4 (STT-00185638) inhibitor, respectively, by successive generation of chemical transformations according to the invention are shown in Tables 17 and 18, respectively. Notably, each successive compound generated demonstrated an increase in the respective predicted dopamine D2 or dopamine D4 Bayesian score, which was set as the primary objective of the optimisation criteria.

In more detail, the transformation from Donepezil to the selected dopamine D2 ligand (GFR-VII-285, 6_38) is illustrated stepwise in Table 17. The sequential chemical transformations that together evolved and optimised GFR-VII-285 are indicated under the heading 'reaction name'. The increase in predicted dopamine D2 activity (calculated using a high confidence dopamine D2 Bayesian model) for each successive generation of compounds is evidenced by the decline in the predicted Bayesian Activity score for acetylcholinesterase activity (AChE). The predicted pharmacokinetics scores for various drug profiles (i.e. Oral non-CNS, Oral CNS, intravenous non-CNS, and intravenous CNS) for each generation of compound is also displayed. In agreement with the low predicted activity score, it can be seen that donepezil has a very weak affinity for dopamine D2 receptor with only 18.6% inhibition. In contrast the evolved optimised compound 6_38 (GFR-VII-285) exhibits 96.2% inhibition of the dopamine D2 receptor and has a binding affinity (Ki) of 156 nM.

Likewise, the molecular transformations from donepezil to a dopamine D4 ligand/antagonist (STT-00185638, 6_1) are illustrated in Table 18. As before, the sequential chemical transformations that together evolved and optimised STT-00185638 are indicated under the heading 'reaction name'. The increase in predicted dopamine D4 activity (calculated using a high confidence dopamine D4 Bayesian model) for each successive generation of compounds is tracked by a decline in the predicted Bayesian Activity score for acetylcholinesterase activity (AChE). The predicted pharmacokinetics scores for various drug profiles (i.e. Oral non-CNS, Oral CNS, intravenous non-CNS, and intravenous CNS) for each generation of compounds is also displayed. The measured binding affinities (Ki) of donepezil and the optimised compound 6_1 (STT-00185638) for dopamine D4 receptor were measured to be 614 nM and 9.5 nM, respectively, representing a 65-fold increase in affinity by the optimisation method.

Accordingly, the method used in the Example successfully evolved compounds towards an achievement objective and the selected prioritised compounds were subsequently confirmed to be dopamine D2 or dopamine D4 antagonists. The structures of the prioritised, optimised compounds could not have been predicted based on the structure of donepezil. Furthermore, the compounds tested had not been previously synthesised and tested.

TABLE 14

Biological activity of selected dopamine D2 and dopamine D4 receptor antagonists, and donepezil 'Activity In % Inh'

|  | 5ht1a (% inh) | Alpha1A (% inh) | Alpha1B (% inh) | Alpha1D (% inh) | D1 (% inh) | D2 (% inh) | D3 (% inh) | D4 (% inh) | D5 (% inh) |
| --- | --- | --- | --- | --- | --- | --- | --- | --- | --- |
| GFR-VII-273 | 92.5 | 102.2 | 102.5 | 99.3 | 49.5 | 85 | 94.1 | 99.6 | 31.8 |
| GFR-VII-274 | 98.2 | 99.7 | 102.1 | 92.1 | 81.9 | 95.5 | 101.1 | 99.1 | 47.2 |
| GFR-VII-280-HCl | 92 | 101.5 | 101 | 98.7 | 30 | 69.8 | 95.7 | 95.9 | 6 |
| GFR-VII-280 | 92.4 | 101.2 | 104.4 | 97.3 | 29.3 | 66.6 | 98.1 | 97.2 | 21.8 |
| GFR-VII-281 | 99.2 | 102.8 | 104.1 | 98.5 | 45.8 | 84.6 | 98.4 | 97.6 | 28.7 |
| GFR-VII-285 | 93.3 | 102.7 | 101.5 | 96.8 | 91.3 | 96.2 | 100.5 | 91.6 | 75.1 |
| GFR-VII-287 | 97.7 | 101 | 101.3 | 99 | 85.1 | 93.6 | 102.8 | 89.6 | 29.4 |
| GFR-VII-290 | 98.3 | 99.1 | 52.4 | 100.5 | 54.5 | 82.1 | 94.7 | 97.3 | 32.5 |
| donepezil | 19.1 | 77.2 | 29.8 | 90.1 | 13.3 | 18.6 | 55.7 | 89.2 | 8.7 |
| STT-00185638 | 64.9 | 69.1 | 16 | 42.8 | 50.8 | 66.2 | 63.6 | 99.4 | 9.7 |
| STT-00185641 |  | 64.8 | −19.8 | 31.1 | −1 | 2 | 51 | 6.9 | 18 |

TABLE 14-continued

Biological activity of selected dopamine D2 and dopamine D4 receptor antagonists, and donepezil

| | 'Activity in nM' | | | | | | | | |
|---|---|---|---|---|---|---|---|---|---|
| | 5ht1a KI (nM) | Alpha1A KI (nM) | Alpha1B KI (nM) | Alpha1D KI (nM) | D1 KI (nM) | D2 KI (nM) | D3 KI (nM) | D4 KI (nM) | D5 KI (nM) |
| GFR-VII-273 | 6.5 | 64.9 | | 81.1 | | 812 | | 13 | |
| GFR-VII-274 | 20 | 257.5 | 3577 | 212.8 | 1628 | 584 | | 28 | |
| GFR-VII-280-HCl | 2.4 | 8.5 | 29.1 | 5.1 | | 1739 | | 187 | |
| GFR-VII-280 | 3.5 | 15.9 | 38.7 | 12.4 | | 1651 | | 191 | |
| GFR-VII-281 | 2.3 | 35.8 | 152.5 | 72.2 | | 1112 | | 264 | |
| GFR-VII-285 | 23 | 0.9 | 19.3 | 4.4 | 531 | 156 | | 436 | |
| GFR-VII-287 | 62 | 75.5 | 91 | 49.6 | 1406 | 585 | | 925 | |
| GFR-VII-290 | 19 | 59.9 | 608.1 | 56 | 2734 | 1367 | | 115 | |
| donepezil | 10000 | 1463 | | 1918 | | | | 614 | |
| STT-00185638 | 7082 | 2057 | | | 6364 | 2457 | | 9.5 | |
| STT-00185641 | 8430 | 2010 | | | | | | | |

TABLE 15

Predicted biological activity of selected dopamine D2 and dopamine D4 receptor antagonists, and donepezil

| | 'Prediction All compounds' | | | | | | | | |
|---|---|---|---|---|---|---|---|---|---|
| | 5-HT1a | Alpha-1a | Alpha-1b | Alpha-1d | Dopamine D1 | Dopamine D2 | Dopamine D3 | Dopamine D4 | Dopamine D5 |
| GFR-VII-273 | 96.8 | 84.4 | 84.9 | 85.3 | 42.4 | 91.7 | 71.3 | 62.9 | 4.3 |
| GFR-VII-274 | 87.9 | 74.3 | 76.0 | 76.2 | 45.6 | 99.9 | 88.6 | 73.6 | −6.1 |
| GFR-VII-280-HCl | 91.5 | 83.4 | 84.0 | 84.5 | 44.0 | 89.4 | 67.1 | 63.3 | 3.8 |
| GFR-VII-280 | 91.5 | 83.4 | 84.0 | 84.5 | 44.0 | 89.4 | 67.1 | 63.3 | 3.8 |
| GFR-VII-281 | 82.5 | 73.4 | 75.0 | 75.4 | 47.2 | 97.6 | 84.3 | 74.0 | −6.6 |
| GFR-VII-285 | 87.5 | 85.6 | 86.0 | 86.5 | 48.4 | 91.8 | 80.5 | 62.9 | 4.8 |
| GFR-VII-287 | 75.1 | 76.9 | 78.2 | 78.5 | 46.2 | 94.0 | 93.1 | 70.2 | −7.8 |
| GFR-VII-290 | 92.0 | 79.1 | 79.5 | 80.3 | 37.8 | 86.5 | 72.4 | 62.2 | 1.4 |
| donepezil | −9.5 | 5.9 | 7.5 | 6.8 | 11.3 | 24.6 | 29.2 | 35.3 | −21.6 |
| STT-00185638 | −7.5 | 62.2 | 65.0 | 64.1 | 6.6 | 81.8 | 15.6 | 122.4 | −20.0 |
| STT-00185641 | 16.8 | 75.9 | 78.1 | 78.0 | 17.7 | 84.4 | 25.9 | 119.5 | −3.0 |

| | 'Prediction High Confidence' | | | | | | | | |
|---|---|---|---|---|---|---|---|---|---|
| | 5-HT1a | Alpha-1a | Alpha-1b | Alpha-1d | Dopamine D1 | Dopamine D2 | Dopamine D3 | Dopamine D4 | Dopamine D5 |
| GFR-VII-273 | 93.1 | 68.3 | 64.0 | 65.1 | 43.9 | 81.3 | 66.2 | 54.0 | 36.2 |
| GFR-VII-274 | 81.8 | 40.2 | 25.5 | 34.5 | 48.2 | 91.3 | 85.5 | 65.0 | 26.2 |
| GFR-VII-280-HCl | 87.7 | 70.0 | 64.4 | 69.3 | 48.0 | 79.4 | 64.6 | 56.6 | 31.7 |
| GFR-VII-280 | 87.7 | 70.0 | 64.4 | 69.3 | 48.0 | 79.4 | 64.6 | 56.6 | 31.7 |
| GFR-VII-281 | 76.4 | 42.0 | 25.8 | 38.7 | 52.3 | 89.4 | 83.9 | 67.7 | 21.7 |
| GFR-VII-285 | 81.7 | 78.6 | 66.4 | 74.6 | 47.4 | 79.8 | 77.9 | 52.3 | 33.8 |
| GFR-VII-287 | 67.8 | 51.3 | 27.8 | 44.1 | 47.2 | 85.3 | 90.2 | 61.4 | 22.9 |
| GFR-VII-290 | 88.2 | 67.6 | 62.8 | 64.0 | 39.3 | 75.8 | 67.4 | 53.3 | 34.2 |
| donepezil | −12.5 | −5.7 | −10.7 | −8.5 | 6.8 | 9.0 | 22.7 | 26.3 | −3.6 |
| STT-00185638 | −9.8 | −18.8 | −15.8 | −19.5 | 6.3 | 67.7 | 10.3 | 112.1 | 3.1 |
| STT-00185641 | 14.1 | 7.8 | 10.5 | 9.5 | 18.7 | 72.6 | 20.8 | 111.1 | 19.2 |

TABLE 16

Predicted ADME properties of selected dopamine D2
and dopamine D4 receptor antagonists, and donepezil
'ADMET Score'

| | | | | | |
|---|---|---|---|---|---|
| GFR-VII-273 | 0.3232 | 0.3132 | 0.5043 | 0.4886 | 0.5043 |
| GFR-VII-274 | 0.1428 | 0.112 | 0.2258 | 0.177 | 0.2258 |
| GFR-VII-280-HCl | 0.332 | 0.3233 | 0.514 | 0.5006 | 0.514 |
| GFR-VII-280 | 0.332 | 0.3233 | 0.514 | 0.5006 | 0.514 |
| GFR-VII-281 | 0.1801 | 0.1412 | 0.2818 | 0.2209 | 0.2818 |
| GFR-VII-285 | 0.3367 | 0.1187 | 0.54 | 0.1903 | 0.54 |

TABLE 16-continued

Predicted ADME properties of selected dopamine D2 and dopamine D4 receptor antagonists, and donepezil 'ADMET Score'

| | Oral Non CNS | Oral CNS | Intravenous Non CNS | Intravenous CNS | scoremax |
|---|---|---|---|---|---|
| GFR-VII-287 | 0.1696 | 0.06694 | 0.2665 | 0.1052 | 0.2665 |
| GFR-VII-290 | 0.3234 | 0.3102 | 0.5045 | 0.4839 | 0.5045 |
| donepezil | 0.1578 | 0.1429 | 0.2543 | 0.2302 | 0.2543 |
| STT-00185638 | 0.2198 | 0.1931 | 0.3348 | 0.2941 | 0.3348 |
| STT-00185641 | 0.2697 | 0.305 | 0.4296 | 0.4859 | 0.4859 |

TABLE 17
Structural evolution of a dopamine D2 receptor antagonist by molecular transformation of donepezil to compound 6_38
| Molecule | name | ReactionNames | Oral Non CNS | Oral CNS | Intravenous Non CNS | Intravenous CNS | Dopamine D2_all | AChE | Dopamine D2_HighConfidence |
|---|---|---|---|---|---|---|---|---|---|
| 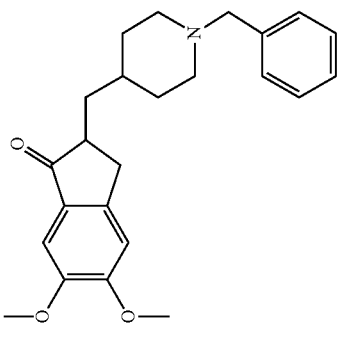 donepezil | donepezil | | 0.0945 | 0.143 | 0.254 | 0.230 | 25 | 85 | 9.0 |
| 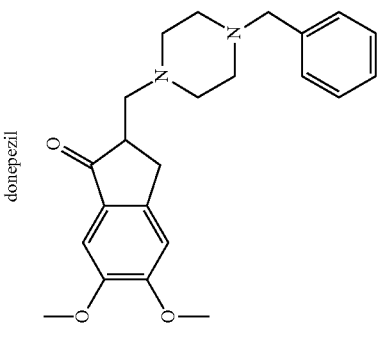 1_8 | 1_8 | C_to_N_a_2 | 0.137 | 0.184 | 0.371 | 0.298 | 36 | 69 | 22 |

TABLE 17-continued
Structural evolution of a dopamine D2 receptor antagonist by molecular transformation of donepezil to compound 6_38
| Molecule | name | ReactionNames | Oral Non CNS | Oral CNS | Intravenous Non CNS | Intravenous CNS | Dopamine D2_all | AChE | Dopamine D2_HighConfidence |
|---|---|---|---|---|---|---|---|---|---|
| 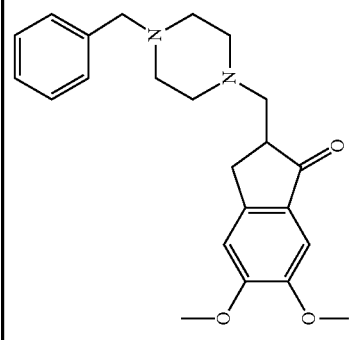 | 2_4 | C_to_N_a_2 Eth_to_But | 0.190 | 0.0806 | 0.327 | 0.131 | 55 | 67 | 36 |
| 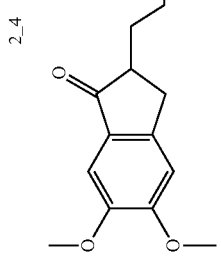 | 3_21 | C_to_N_a_2 Eth_to_But methylene_deletion a_2 | 0.0700 | 0.112 | 0.211 | 0.185 | 63 | 43 | 40 |

TABLE 17-continued

Structural evolution of a dopamine D2 receptor antagonist by molecular transformation of donepezil to compound 6_38

| Molecule | name | ReactionNames | Oral Non CNS | Oral CNS | Intravenous Non CNS | Intravenous CNS | Dopamine D2_all | AChE | Dopamine D2_HighConfidence |
|---|---|---|---|---|---|---|---|---|---|
| 4_3 | 4_3 | C_to_N_a 2<br>Eth_to_But<br>methylene_deletion_a 2<br>aryl_H_to_aryl_OMe | 0.163 | 0.0644 | 0.281 | 0.105 | 78 | 24 | 61 |
| 5_17 | 5_17 | C_to_N_a 2<br>Eth_to_But<br>methylene_deletion_a 2<br>aryl_H_to_aryl_OMe | 0.343 | 0.127 | 0.567 | 0.203 | 86 | 21 | 73 |
| 6_38 | 6_38 | C_to_N_a 2<br>Eth_to_But<br>methylene_deletion_a 2<br>aryl_H_to_aryl_OMe<br>C_to_N_a 2<br>methylene_insertion_b 2 | 0.326 | 0.119 | 0.540 | 0.190 | 94 | −21 | 70 |

TABLE 18

Structural evolution of a dopamine D4 receptor antagonist by molecular transformation of donepezil to compound 6_1

| Molecule | name | ReactionNames | Oral Non CNS | Oral CNS | Intravenous Non CNS | Intravenous CNS | Dopamine D4_all | AChE | Dopamine D4_HighConfidence |
|---|---|---|---|---|---|---|---|---|---|
| donepezil | donepezil | | 0.0945 | 0.143 | 0.254 | 0.230 | 35 | 85 | 26 |
| 2_181 | 2_181 | C_to_N_a 2<br>MeInsertion | 0.204 | 0.0838 | 0.331 | 0.136 | 46 | 44 | 35 |
| 3_4958 | 3_4958 | C_to_N_a 2<br>MeInsertion<br>C_to_N_a 2 | 0.231 | 0.0650 | 0.374 | 0.106 | 40 | 30 | 39 |
| 4_1 | 4_1 | C_to_N_a 2<br>MeInsertion<br>C_to_N_a 2<br>amide inversion 2 | 0.265 | 0.109 | 0.404 | 0.166 | 93 | 13 | 83 |

TABLE 18-continued

Structural evolution of a dopamine D4 receptor antagonist by molecular transformation of donepezil to compound 6_1

| Molecule | name | ReactionNames | Oral Non CNS | Oral CNS | Intra-venous Non CNS | Intra-venous CNS | Dopamine D4_all | AChE | Dopamine D4_HighConfidence |
|---|---|---|---|---|---|---|---|---|---|
| 5_2 | 5_2 | C_to_N_a 2<br>MeInsertion<br>C_to_N_a 2<br>amide_inversion 2<br>aryl_MeO_to_Aryl_H 2 | 0.235 | 0.204 | 0.358 | 0.311 | 105 | 4.5 | 94 |
| 5_3 | 5_3 | C_to_N_a 2<br>MeInsertion<br>C_to_N_a 2<br>amide_inversion 2<br>aryl_MeO_to_Aryl_H 2 | 0.230 | 0.200 | 0.351 | 0.306 | 105 | 5.1 | 94 |
| 6_1 | 6_1 | C_to_N_a 2<br>MeInsertion<br>C_to_N_a 2<br>amide_inversion 2<br>aryl_MeO_to_Aryl_H 2<br>aryl_MeO_to_Aryl H 2 | 0.220 | 0.193 | 0.335 | 0.294 | 122 | −8.9 | 112 |

In summary, starting from the chemical structure of the known acetylcholinesterase drug, donepezil, the selective optimisation of new compounds having dopamine D4 and dopamine D2 receptor antagonist activity was achieved in 6 generations (or iterations) of the invention. On further analysis of the literature it is interesting to note that the optimised dopamine D4 receptor antagonists are close analogues of known dopamine D4 antagonist compounds. Furthermore, chemical structure similarity searches of the prioritised compounds against the literature databases reveal the prioritised 2,3-dihydro-indol-1-yl chemotype does indeed exhibit potent dopamine 4 activity. Several of the prioritised structures are novel and, hence, have not previously been proposed or tested as dopamine antagonists.

However, in a further verification of the method of the invention, it has been discovered using a structural similarity search, that a close analogue of compound STT-00185638 (2-[-4-(benzyl)-piperazin-1-yl]-1-(2-methy-2,3-dihydro-indol-1-yl)-ethanone), i.e. (2-[-4-(4-fluro-benzyl)-piperazin-1-yl]-1-(2-methy-2,3-dihydro-indol-1-yl)-ethanone) is indeed a potent dopamine D4 antagonist (Ki=7 nM) and exhibits a selectivity over D2 of 671-fold. Several close analogues of the prioritised compounds have also been reported to be dopamine D4 antagonists, for example: Zhao et al. (2002, *Bioorganic & Med. Chem. Letters*, 12, 3105-3109); and Zhao et al. (2002, *Bioorganic & Med. Chem. Letters*, 12, 3111-3115). Interestingly, 4-(4-hydro-benzyl) analogues have not been previous tested.

STT-00185638 selected by the method of the invention is a previously unknown potent, selective antagonist of dopamine D4. It further displays good pharmacokinetic properties, which may be superior to any of the previously published analogues.

Finally, literature searching also revealed that the chemical structure of (2-(4-(4-Phenyl-1-piperazinyl)butyl)-1-isoindolinone), an analogue of prioritised compound GFR-VII-269 had been previously assayed against dopamine D2 (Ki=319 nM) and dopamine D4 (Ki=134 nM).

Assay Methods: Secondary Radioligand Binding Assays

A. Serotonin receptors: 5-HT1A, HT1B, 5-HT1D, 5-HT1E, 5-HT2A, 5-HT2B, 5-HT2C, 5-HT3, 5-HT5A, 5-HT6 and 5-HT7

Assay Buffer: Standard Binding Buffer (50 mM Tris-HCl, 10 mM $MgCl_2$, 1 mM EDTA, pH 7.4)

Membrane Fraction Source: Transiently or stably transfected cell lines (e.g., HEK293, COS, CHO, NIH3T3)

Protocol adapted from Roth et al. (1986), *J. Pharmacol. Exp. Ther.*, 238(2): 480-485; and Roth et al. (1994), *J. Pharmacol. Exp. Ther.*, 268(3): 1403-1410.

Experimental Procedure and Data Analysis

A solution of the compound to be tested is prepared as a 1 mg/ml stock in Standard Binding Buffer or DMSO according to its solubility. A similar stock of a reference compound (positive control) is also prepared. Eleven dilutions (5× assay concentration) of the test and reference (see Table 19) compounds are prepared in Standard Binding Buffer by serial dilution: 0.05 nM, 0.5 nM, 1.5 nM, 5 nM, 15 nM, 50 nM, 150 nM, 500 nM, 1.5 µM, 5 µM, 50 µM (thus, the corresponding assay concentrations span from 10 µM to 10 µM and includes semilog points in the range where high-to-moderate affinity ligands compete with radioligand for binding sites).

Radioligand is diluted to five times the assay concentration (see Table 18) in Standard Binding Buffer. Typically, the assay concentration of radioligand is a value between one half the KD and the KD of a particular radioligand at its target. 50 µl aliquots of radioligand are dispensed into the wells of a 96-well plate containing 100 µl of Standard Binding Buffer. Then, duplicate 50 µl aliquots of the test and reference compound dilutions are added.

Finally, crude membrane fractions of cells expressing recombinant target (prepared from 10 cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; typically, one 10 cm plate provides sufficient material for 24 wells), are resuspended in 3 ml of chilled Standard Binding Buffer and homogenized by several passages through a 26 gauge needle, then 50 µl are dispensed into each well.

The 250 µl reactions are incubated at room temperature and shielded from light (to prevent photolysis of light-sensitive ligands) for 1.5 hours, then harvested by rapid filtration onto Whatman GF/B glass fiber filters pre-soaked with 0.3% polyethyleneimine using a 96-well Brandel harverster. Four rapid 500 µl washes are performed with chilled Standard Binding Buffer to reduce non-specific binding. Filters are placed in 6 ml scintillation tubes and allowed to dry overnight. The next day, 4 ml of EcoScint scintillation cocktail (National Diagnostics) are added to each tube. The tubes are capped, labeled, and counted by liquid scintillation counting. For higher throughput assays, bound radioactivity is harvested onto 0.3% polyethyleneimine-treated, 96-well filter mats using a 96-well Filtermate harvester. The filter mats are dried, then scintillant is melted onto the filters and the radioactivity retained on the filters is counted in a Microbeta scintillation counter.

Raw data (dpm) representing total radioligand binding (i.e. specific+non-specific binding) are plotted as a function of the logarithm of the molar concentration of the competitor (i.e. test or reference compound). Non-linear regression of the normalised (i.e. percent radioligand binding compared to that observed in the absence of test or reference compound) raw data is performed in Prism 4.0 (GraphPad Software) using the built-in three parameter logistic model describing ligand competition binding to radioligand-labeled sites:

$$y = \text{bottom} + [(\text{top-bottom})/(1+10^{x-\log IC50})]$$

where bottom equals the residual radioligand binding measured in the presence of 10 µM reference compound (i.e. non-specific binding) and top equals the total radioligand binding observed in the absence of competitor. The log IC50 (i.e. the log of the ligand concentration that reduces radioligand binding by 50%) is thus estimated from the data and used to obtain the Ki by applying the Cheng-Prusoff approximation:

$$Ki = IC50/(1+[\text{ligand}]/KD)$$

where [ligand] equals the assay radioligand concentration and KD equals the affinity constant of the radioligand for the target receptor.

TABLE 19

Serotonin (5-HT) receptor radioligands, radioligand assay concentrations, and reference compounds

| Receptor | Radioligand (Assay Conc.) | Reference Compound |
|---|---|---|
| 5-HT1A | [3H]8-OH-DPAT (0.5 nM) | Methysergide |
| 5-HT1B | [3H]GR125743 (0.3 nM) | Ergotamine |
| 5-HT1D | [3H]GR125743 (0.3 nM) | Ergotamine |
| 5-HT1E | [3H]5-HT (3 nM) | 5-HT |
| 5-HT2A | [3H]Ketanserin (0.5 nM) | Chlorpromazine |
| 5-HT2B | [3H]LSD (1 nM) | 5-HT |
| 5-HT2C | [3H]Mesulergine (0.5 nM) | Chlorpromazine |
| 5-HT3 | [3H]LY278584 (0.3 nM) | LY278584 |
| 5-HT5A | [3H]LSD (1 nM) | Ergotamine |
| 5-HT6 | [3H]LSD (1 nM) | Chlorpromazine |
| 5-HT7 | [3H]LSD (1 nM) | Chlorpromazine |

B. Dopamine Receptors: D1, D2, D3, D4, D5

Assay Buffers: Dopamine Binding Buffer (50 mM NaCl, 50 mM HEPES-HCl, 5 mM $MgCl_2$, 0.5 mM EDTA, pH 7.4)

Membrane Fraction Source: Transiently or stably transfected cell lines (e.g. HEK293, COS, CHO, NIH3T3)

Protocol adapted from Roth et al. (1995), *Psychopharmacology* 120(3): 365-368.

Experimental Procedure and Data Analysis

The method is carried out in the manner described for the serotonin receptor assay above. Eleven dilutions (5× assay concentration) of the test and reference (see Table 19)

compounds are prepared in Dopamine Binding Buffer by serial dilution, as previously described. Radioligand is diluted to five times the assay concentration (see Table 20) in Dopamine Binding Buffer.

TABLE 20

Dopamine receptor radioligands, radioligand assay concentrations, and reference compounds

| Receptor | Radioligand (Assay Conc.) | Reference Compound |
| --- | --- | --- |
| D1 | [3H]SCH23390 (0.2 nM) | SKF38393 |
| D2 | [3H]N-methylspiperone (0.2 nM) | Haloperidol |
| D3 | [3H] N-methylspiperone (0.2 nM) | Chlorpromazine |
| D4 | [3H] N-methylspiperone (0.3 nM) | Chlorpromazine |
| D5 | [3H]SCH23390 (0.2 nM) | SKF38393 |

C. Adrenergic Receptors: α1A, α1B, α2A, α2B, α2C, β1, β2, β3

Assay Buffers: For α1 receptors, al Binding Buffer (20 mM Tris-HCl, 145 mM NaCl, pH 7.4); for α2 receptors, α2 Binding Buffer (50 mM Tris-HCl, 5 mM $MgCl_2$, pH 7.7); for β receptors, β Binding Buffer (50 mM Tris-HCl, 3 mM $MnCl_2$, pH 7.7)

Membrane Fraction Source: Transiently or stably transfected cell lines (e.g. HEK293, COS, CHO, NIH3T3)

Protocol adapted from Arango et al. (1993), *Brain Res.,* 630(1-2): 271-282; and Arango et al. (1990), *Gen. Psychiatry,* 47: 1038-1047.

Experimental Procedure and Data Analysis

The method is carried out in the manner described for the serotonin receptor assay above, except where described below. Eleven dilutions (5× assay concentration) of the test and reference (see Table 20) compounds are prepared in the appropriate buffer by serial dilution, as previously described. Radioligand is diluted to five times the assay concentration (see Table 21) in the appropriate buffer.

The 250 µl reactions are incubated at room temperature and shielded from light (to prevent photolysis of light-sensitive ligands) for 1 hour (for α1 receptors, 40 min for α2 receptors, and 1.5 hours for β receptors), then harvested by rapid filtration onto Whatman GF/B glass fiber filters pre-soaked with 0.3% polyethyleneimine using a 96-well Brandel harvester. Four rapid 500-µl washes are performed with chilled distilled water (for α1 and β receptors) or 0.1% polyethyleneimine (for α2 receptors) to reduce non-specific binding. Filters are placed in 6 ml scintillation tubes and allowed to dry overnight and the samples are treated to obtain data as described above.

TABLE 21

Adrenergic receptor radioligands, radioligand assay concentrations, and reference compounds

| Receptor | Radioligand (Assay Conc.) | Reference Compound |
| --- | --- | --- |
| α1A | [125I]HEAT (0.1 nM) | Urapidil |
| α1B | [125I]HEAT (0.1 nM) | Corynanthine |
| α2A | [125I]Iodoclonidine (0.1 nM) | Oxymetazoline |
| α2B | [125I]Iodoclonidine (1 nM) | Prazosin |
| α2C | [125I]Iodoclonidine (1 nM) | Prazosin |
| β1 | [125I]Iodopindolol (0.1 nM) | Alprenolol |
| β2 | [125I]Iodopindolol (0.1 nM) | Alprenolol |
| B3 | [125I]Iodopindolol (0.1 nM) | Alprenolol |

Example 3

Demonstration of the Algorithm to Design Against Anti-Targets to Improve Selectivity In many drug discovery programmes it is often necessary to improve the ratio of the affinity of a lead compound for a desired target molecule over an undesired target molecule. This ratio of the affinity for an undesired target over a desired target is referred to as the selectivity of a compound. Since achieving selectivity can be such an important problem to be solved, in this Example we applied the algorithm of the invention to the design of compounds that have increased selectivity for desired targets over undesired targets.

The seven isoindole analogues that were selected in Example 2 (i.e. GFR-VII-274, GFR-VII-281, GFR-VII-285, GFR-VII-287, GFR-VII-280 GFR-VII-290, and GFR-VII-273) to have improved binding activity for dopamine D2 demonstrated a significantly increased affinity for the dopamine D2 receptor over the starting compound donepezil. However, activity against other receptors where not taken into account in that example. The overall predictions of receptor promiscuity, which have been confirmed by experimental receptor profiling in vitro, demonstrated that the isoindole series of compounds were promiscuous, with potent affinities for 5HT1a, 5HT1b 5HT1d, 5HT7, Alpha1a, Alpha 1b, 5HT2b, Alpha1d, dopamine D3 and dopamine D4 receptors. In this example, therefore, a new Achievement Objective was defined, i.e. to further evolve the seven isoindoles compounds of Example 2 against the defined objectives of improving activity against the 5HT1a, dopamine D3 and dopamine D4 receptors, but with increased selectivity over the "anti-target" Alpha-1 receptors, i.e. Alpha1a, Alpha1b and Alpha1d.

Molecular evolution was carried out essentially as described in Example 2.

In one model, an additional Achievement Objective was set to select for compounds in the final generation that were not previously known, i.e. they do not appear at the level of the Murcko framework within the ChEMBL database (version 1). The novelty of a compound can be defined by several methods. The first method is to define novelty by comparing the exact chemical structure (or exact structure defined in a structural representation, such as SMILES or InChI) with a database of known chemical structures by database querying methods. If no match is found the compound can be defined as novel for that database. Within the algorithm, the novelty of a compound was assessed according to its Murcko framework (carbon backbone), which was compared to the Murko frameworks of all other compounds in the database (Bemis & Murcko (1996), The properties of known drugs. 1. Molecular Frameworks, *J. Med. Chem.,* 39(15), pp 2887-2893). In this example, the Murcko frameworks of the evolved compounds were compared to chemical structures in the ChEMBL version 1.0 database as of 2008 (https://www.ebi.ac.uk/chembl/).

The evolutionary optimisation resulted in the design of a series of benzolactam derivatives. Six compounds, termed GFR-VII-327, GFR-VII-328, GFR-VII-329, GFR-VII-330, GFR-VII-331 and GFR-VII-332 where chosen for in vitro synthesis based on the prioritisation method. The benzolactam series was not present in the ChEMBL 1.0 database, and thus are considered a novel chemical series in the algorithm. A subsequent literature search revealed that the proposed compounds were recently synthesised and shown to be potent dopamine D2/dopamine D3 binding ligands (Ortega et al., (2009), Synthesis, binding affinity and SAR of new benzolactam derivatives as dopamine D3 receptor ligands, *Bioorg. Med. Chem. Letts.,* 19, 1773-8).

In Vitro Assays

The selected benzolactam compounds were synthesised and compared in vitro to the series of isoindole analogues from Example 2 by measuring binding affinity for the compounds for their defined target and non-target receptors. The results demonstrated that the benzolactam analogues achieved the objective of an increased selectivity profile for dopamine D2, dopamine D3 and 5HT1a receptors over the Alpha-1 receptors, as shown in Tables 22 to 24.

TABLE 22

Selectivity of Dopamine D2 over $\alpha_1$ Receptors

| Compound No. | $K_i\alpha_{1A}$ (nM) | $K_i\alpha_{1B}$ (nM) | $K_i\alpha_{1D}$ (nM) | $K_iD2$ (nM) | $\alpha_{1A}/D2$ | $\alpha_{1B}/D2$ | $\alpha_{1D}/D2$ | $\alpha_1/D2$ |
|---|---|---|---|---|---|---|---|---|
| GFR-VII-266 | 59.8 | 101.8 | 85.8 | 746 | 0.080 | 0.136 | 0.115 | 0.1 |
| GFR-VII-269 | 6.2 | 54.9 | 3.8 | 93 | 0.067 | 0.590 | 0.041 | 0.2 |
| GFR-VII-273 | 64.9 | 322.8 | 81.1 | 812 | 0.080 | 0.398 | 0.100 | 0.12 |
| GFR-VII-274 | 257.5 | 3577 | 212.8 | 584 | 0.441 | 6.125 | 0.364 | 2.3 |
| GFR-VII-280-HCl | 8.5 | 29.1 | 5.1 | 1739 | 0.005 | 0.017 | 0.003 | 0.008 |
| GFR-VII-280 | 15.9 | 38.7 | 12.4 | 1651 | 0.010 | 0.023 | 0.008 | 0.014 |
| GFR-VII-281 | 35.8 | 152.5 | 72.2 | 1112 | 0.032 | 0.137 | 0.065 | 0.078 |
| GFR-VII-285 | 0.9 | 19.3 | 4.4 | 156 | 0.006 | 0.124 | 0.028 | 0.053 |
| GFR-VII-287 | 75.5 | 91 | 49.6 | 585 | 0.129 | 0.156 | 0.085 | 0.123 |
| GFR-VII-290 | 59.9 | 608.1 | 56 | 1367 | 0.044 | 0.445 | 0.041 | 0.177 |
| Average isoindoles Series | 58.5 | 499.5 | 58.3 | 884.5 | 0.089 | 0.815 | 0.085 | 0.330 |
| GFR-VII-327 | 117.2 | 649 | 78.4 | 14 | 8.371 | 46.4 | 5.6 | 20.11 |
| GFR-VII-328 | 11.1 | 76.6 | 14.2 | 25 | 0.444 | 3.01 | 0.57 | 1.34 |
| GFR-VII-329 | 555.4 | 1375 | 467.3 | 886.1 | 0.627 | 1.55 | 0.53 | 0.9 |
| GFR-VII-330 | 216.8 | 656.7 | 209.6 | 5.8 | 37.379 | 113.22 | 36.14 | 62.2 |
| GFR-VII-331 | 7.2 | 125.3 | 37.6 | 5.7 | 1.263 | 21.98 | 6.6 | 9.95 |
| GFR-VII-332 | 866.6 | 2542 | 979.6 | 131.8 | 6.575 | 19.29 | 7.4 | 11.1 |
| Average Benzolactam series | 295.7 | 904.1 | 297.8 | 178.1 | 9.110 | 34.24 | 9.5 | 17.61 |

TABLE 23

Selectivity of Dopamine D3 over $\alpha_1$ Receptors

| Compound No. | $K_i\alpha_{1A}$ (nM) | $K_i\alpha_{1B}$ (nM) | $K_i\alpha_{1D}$ (nM) | $K_iD3$ (nM) | $\alpha_{1A}/D2$ | $\alpha_{1B}/D2$ | $\alpha_{1D}/D2$ | $\alpha_1/D2$ |
|---|---|---|---|---|---|---|---|---|
| GFR-VII-266 | 59.8 | 101.8 | 85.8 | 299 | 0.2 | 0.34 | 0.3 | 0.3 |
| GFR-VII-269 | 6.2 | 54.9 | 3.8 | 2.1 | 3.0 | 26.1 | 1.8 | 10.3 |
| GFR-VII-273 | 64.9 | 322.8 | 81.1 | 163 | 0.4 | 1.98 | 0.5 | 1.0 |
| GFR-VII-274 | 257.5 | 3577 | 212.8 | 79 | 3.259 | 45.3 | 2.7 | 17.1 |
| GFR-VII-280-HCl | 8.5 | 29.1 | 5.1 | 180 | 0.05 | 0.16 | 0.03 | 0.1 |
| GFR-VII-280 | 15.9 | 38.7 | 12.4 | 208 | 0.08 | 0.19 | 0.06 | 0.1 |
| GFR-VII-281 | 35.8 | 152.5 | 72.2 | 56 | 0.6 | 2.7 | 1.3 | 1.6 |
| GFR-VII-285 | 0.9 | 19.3 | 4.4 | 11 | 0.08 | 1.8 | 0.4 | 0.75 |
| GFR-VII-287 | 75.5 | 91 | 49.6 | 32 | 2.4 | 2.8 | 1.6 | 2.3 |
| GFR-VII-290 | 59.9 | 608.1 | 56 | 152 | 0.4 | 4.0 | 0.37 | 1.6 |
| Average isoindoles Series | 58.5 | 499.5 | 58.3 | 118.2 | 1.0 | 8.5 | 0.9 | 3.5 |
| GFR-VII-327 | 117.2 | 649 | 78.4 | 1 | 117.2 | 649.0 | 78.4 | 281.5 |
| GFR-VII-328 | 11.1 | 76.6 | 14.2 | 4 | 2.8 | 19.2 | 3.6 | 8.5 |
| GFR-VII-329 | 555.4 | 1375 | 467.3 | 20 | 27.8 | 68.8 | 23.4 | 40.0 |
| GFR-VII-330 | 216.8 | 656.7 | 209.6 | 1 | 216.8 | 656.7 | 209.6 | 361.0 |
| GFR-VII-331 | 7.2 | 125.3 | 37.6 | 0.7 | 10.3 | 179.0 | 53.7 | 81.0 |
| GFR-VII-332 | 866.6 | 2542 | 979.6 | 3 | 288.9 | 847.3 | 326.5 | 487.6 |
| Average Benzolactam series | 295.7 | 904.1 | 297.8 | 5.0 | 110.6 | 403.3 | 115.9 | 209.9 |

TABLE 24

Selectivity of 5HT$_{1A}$ over $\alpha_1$ Receptors

| Compound No. | $K_i\alpha_{1A}$ (nM) | $K_i\alpha_{1B}$ (nM) | $K_i\alpha_{1D}$ (nM) | $K_i$ 5HT$_{1A}$ (nM) | $\alpha_{1A}/D2$ | $\alpha_{1B}/D2$ | $\alpha_{1D}/D2$ | $\alpha_1/D2$ |
|---|---|---|---|---|---|---|---|---|
| GFR-VII-266 | 59.8 | 101.8 | 85.8 | 40 | 1.5 | 2.5 | 2.1 | 2.1 |
| GFR-VII-269 | 6.2 | 54.9 | 3.8 | 2.6 | 2.4 | 21.1 | 1.5 | 8.3 |
| GFR-VII-273 | 64.9 | 322.8 | 81.1 | 6.5 | 10.0 | 49.7 | 12.5 | 24.0 |

TABLE 24-continued

Selectivity of 5HT$_{1A}$ over α$_1$ Receptors

| Compound No. | K$_i$α$_{1A}$ (nM) | K$_i$α$_{1B}$ (nM) | K$_i$α$_{1D}$ (nM) | K$_i$ 5HT$_{1A}$ (nM) | α$_{1A}$/D2 | α$_{1B}$/D2 | α$_{1D}$/D2 | α$_1$/D2 |
|---|---|---|---|---|---|---|---|---|
| GFR-VII-274 | 257.5 | 3577 | 212.8 | 20 | 12.8 | 178.9 | 10.6 | 67.5 |
| GFR-VII-280-HCl | 8.5 | 29.1 | 5.1 | 2.4 | 3.5 | 12.1 | 2.1 | 5.9 |
| GFR-VII-280 | 15.9 | 38.7 | 12.4 | 3.5 | 4.5 | 11.1 | 3.5 | 6.4 |
| GFR-VII-281 | 35.8 | 152.5 | 72.2 | 2.3 | 15.6 | 66.3 | 31.4 | 37.8 |
| GFR-VII-285 | 0.9 | 19.3 | 4.4 | 23 | 0.04 | 0.8 | 0.2 | 0.4 |
| GFR-VII-287 | 75.5 | 91 | 49.6 | 62 | 1.2 | 1.5 | 0.8 | 1.2 |
| GFR-VII-290 | 59.9 | 608.1 | 56 | 19 | 3.2 | 32.0 | 2.9 | 12.7 |
| Average isoindoles Series | 58.5 | 499.5 | 58.3 | 18.1 | 5.5 | 37.6 | 7.2 | 16.8 |
| GFR-VII-327 | 117.2 | 649 | 78.4 | 1.5 | 78.1 | 432.7 | 52.2 | 187.7 |
| GFR-VII-328 | 11.1 | 76.6 | 14.2 | 0.9 | 12.3 | 85.1 | 15.8 | 37.7 |
| GFR-VII-329 | 555.4 | 1375 | 467.3 | 4 | 138.9 | 343.8 | 116.8 | 199.8 |
| GFR-VII-330 | 216.8 | 656.7 | 209.6 | 1.3 | 166.8 | 505.2 | 161.2 | 277.7 |
| GFR-VII-331 | 7.2 | 125.3 | 37.6 | 0.7 | 10.3 | 179.0 | 53.7 | 81.0 |
| GFR-VII-332 | 866.6 | 2542 | 979.6 | 1.2 | 722.2 | 2118.3 | 816.3 | 1218.9 |
| Average Benzolactam series | 295.7 | 904.1 | 297.8 | 1.6 | 188.1 | 610.7 | 202.7 | 333.8 |

On average the synthesised benzolactam compounds were 17.6-fold more selective for the dopamine D2 receptor over the Alpha-1 receptors, which compared favourably to the 0.33-fold selectivity ratio for the dopamine D2 receptor over the Alpha-1 receptors for the isoindole analogues. Thus, as a series the benzolactams demonstrated 53-fold more selectivity for the dopamine D2 receptor over the three Alpha-1 receptors (Alpha-1a, Alpha-1b and Alpha-1d) in comparison to the isoindoles analogues. The selectivity profiles for individual benzolactams ranged up to 62-fold (see GFV-VII-330) for the dopamine D2 receptor over the average Alpha-1 receptor activity.

The average selectivity of the benzolactam series of molecules for the dopamine D3 receptor over the Alpha-1 receptors was 210-fold compared to only 3.5-fold for the isoindoles series.

The selectivity/binding ratio of binding affinity for the 5Ht1a receptor over the average affinity for the Alpha-1a receptors was 333.8-fold for the benzolactams, compared with only 16.6-fold for the isoindole analogues.

The algorithm of the invention thus achieved its defined Achievement Objectives in the design of compounds which were both structurally novel in the database, and had improved selectivity over the Alpha-1 receptors.

Figure 16:
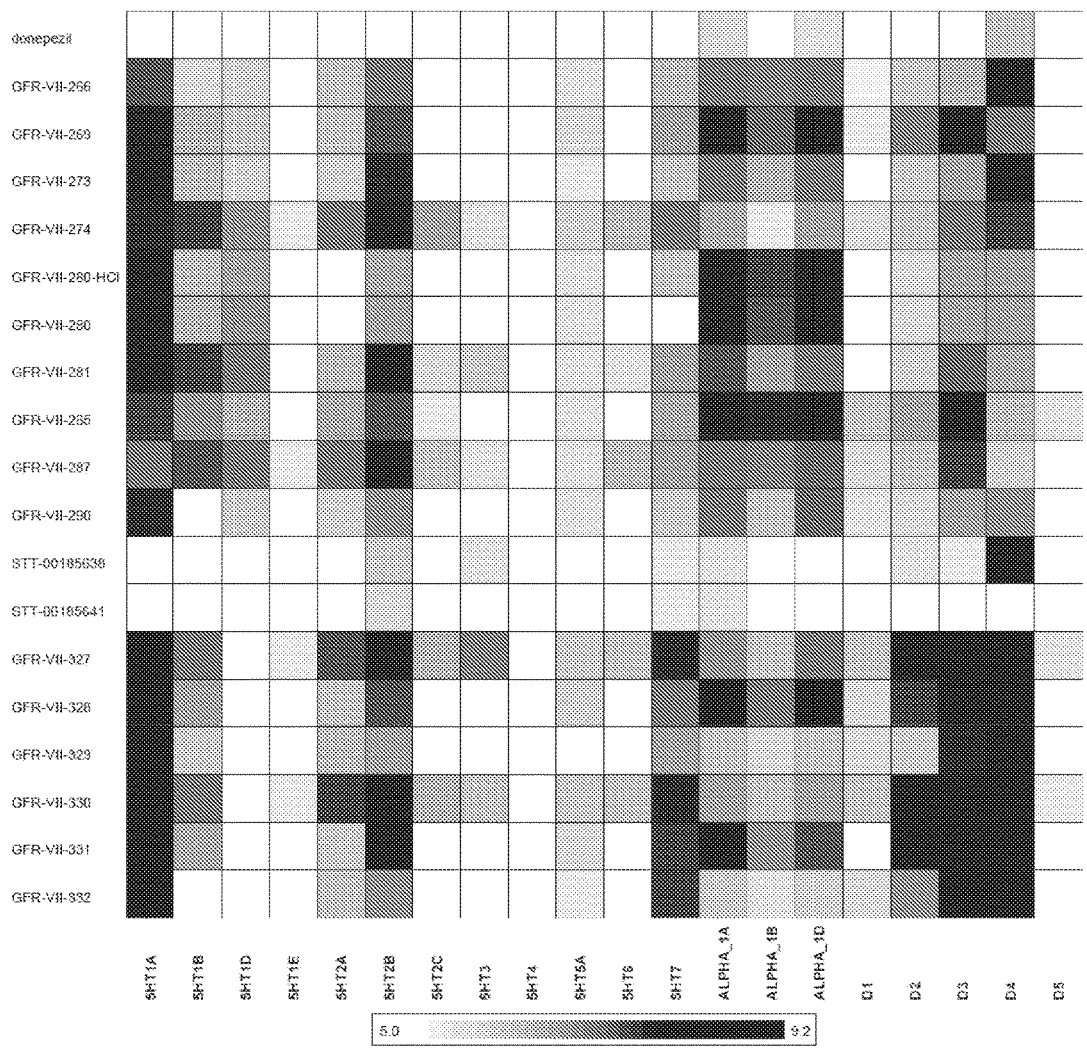
FIG. 16 is a heat map to illustrate the relative binding affinity of compounds selected in accordance with the invention for 20 different receptor molecules.

In addition, the benzolactam compounds and isoindole analogues from Example 2 were compared in radioligand binding assays against a panel of 20 GPCRs. The results illustrate the increased selectivity profile for the benzolactam compounds for dopamine D2, dopamine D3 and 5HT1a receptors over non-target receptors in comparison to other. Measured binding affinities for the compounds against the various receptors are given in Table 25, and a heat map representation of the same data is shown in FIG. 16.

TABLE 25

Experimental Receptor Binding Data-Ki (nM)

| DDE_NAME | 5HT1A | 5HT1B | 5HT1D | 5HT1E | 5HT2A | 5HT2B | 5HT2C | 5HT3 | 5HT5A |
|---|---|---|---|---|---|---|---|---|---|
| donepezil | 10000 | | | | | 6761 | | | |
| GFR-VII-266 | 40 | 1156 | 983 | | 580 | 77 | 10000 | | 2666 |
| GFR-VII-269 | 2.6 | 299 | 504 | | 496 | 40 | 5919 | | 1613 |
| GFR-VII-273 | 6.5 | 362 | 1002 | | 956 | 19 | 10000 | | 2903 |
| GFR-VII-274 | 20 | 27 | 130 | 3683 | 76 | 1 | 217 | 2406 | 1056 |
| GFR-VII-280-HCl | 2.4 | 378 | 176 | | | 242 | 10000 | | 2490 |
| GFR-VII-280 | 3.5 | 306 | 139 | | | 160 | 10000 | | 2154 |
| GFR-VII-281 | 2.3 | 33 | 59 | | 387 | 12 | 1450 | 767 | 1982 |
| GFR-VII-285 | 23 | 130 | 298 | | 270 | 41 | 3428 | | 2437 |
| GFR-VII-287 | 62 | 41 | 80 | 3339 | 65 | 10 | 543 | 1794 | 2367 |
| GFR-VII-290 | 19 | | 829 | | 1004 | 117 | 10000 | | 2471 |
| STT-00185638 | 7082 | | | | | 879 | | 2114 | 6773 |
| STT-00185641 | 8430 | | | | | 1454 | | | |
| GFR-VII-327 | 1.5 | 73 | | 3448 | 39 | 1.8 | 354 | 99 | 773 |
| GFR-VII-328 | 0.9 | 217 | | | 583 | 40 | 9253 | | 1053 |
| GFR-VII-329 | 4 | 834 | | | 384 | 192 | 10000 | | |
| GFR-VII-330 | 1.3 | 73 | | 4367 | 24 | 0.6 | 317 | 677 | 809 |

TABLE 25-continued

Experimental Receptor Binding Data-Ki (nM)

| DDE_NAME | 5HT1A | 5HT1B | 5HT1D | 5HT1E | 5HT2A | 5HT2B | 5HT2C | 5HT3 | 5HT5A |
|---|---|---|---|---|---|---|---|---|---|
| GFR-VII-331 | 0.7 | 232 | | | 755 | 12 | 10000 | | 1131 |
| GFR-VII-332 | 1.2 | | | | 645 | 121 | | | 3082 |

TABLE 25

Experimental Receptor Binding Data-Ki (nM)

| DDE_NAME | 5HT6 | 5HT7 | ALPHA_1A | ALPHA_1B | ALPHA_1D | D1 | D2 | D3 | D4 | D5 |
|---|---|---|---|---|---|---|---|---|---|---|
| donepezil | | | 1463 | | 1918 | | | 10000 | 614 | |
| GFR-VII-266 | | 419 | 59.8 | 101.8 | 85.8 | 5029 | 746 | 299 | 6.4 | |
| GFR-VII-269 | | 162 | 6.2 | 54.9 | 3.8 | 3371 | 93 | 2.1 | 72 | |
| GFR-VII-273 | | 545 | 64.9 | 322.8 | 81.1 | | 812 | 163 | 13 | |
| GFR-VII-274 | 430 | 75 | 257.5 | 3577 | 212.8 | 1628 | 584 | 79 | 28 | |
| GFR-VII-280-HCl | | 529 | 8.5 | 29.1 | 5.1 | | 1739 | 180 | 187 | |
| GFR-VII-280 | | | 15.9 | 38.7 | 12.4 | | 1651 | 208 | 191 | |
| GFR-VII-281 | 2192 | 181 | 35.8 | 152.5 | 72.2 | | 1112 | 56 | 264 | |
| GFR-VII-285 | | 228 | 0.9 | 19.3 | 4.4 | 531 | 156 | 11 | 436 | 1886 |
| GFR-VII-287 | 417 | 164 | 75.5 | 91 | 49.6 | 1406 | 585 | 32 | 925 | |
| GFR-VII-290 | | 732 | 59.9 | 608.1 | 56 | 2734 | 1367 | 152 | 115 | |
| STT-00185638 | | 4363 | 2057 | | | 6364 | 2457 | 3216 | 9.5 | |
| STT-00185641 | | 2824 | 2010 | | | | | 10000 | | |
| GFR-VII-327 | 544 | 21 | 117.2 | 649 | 78.4 | 511 | 14 | 1 | 13 | 2385 |
| GFR-VII-328 | | 77 | 11.1 | 76.6 | 14.2 | 1618 | 25 | 4 | 6 | 6865 |
| GFR-VII-329 | | 150 | 555.4 | 1375 | 467.3 | 1421 | 886.1 | 20 | 17 | |
| GFR-VII-330 | 669 | 20 | 216.8 | 656.7 | 209.6 | 500 | 5.8 | 1 | 9 | 3577 |
| GFR-VII-331 | | 31 | 7.2 | 125.3 | 37.6 | | 5.7 | 0.7 | 4 | |
| GFR-VII-332 | | 26 | 866.6 | 2542 | 979.6 | 1257 | 131.8 | 3 | 8 | |

In conclusion, the method of the invention is successful in evolving molecules having optimised dopamine D2, dopamine D3 and 5HT1a receptor binding activity, with significantly weaker binding affinity for non-target receptors, such as Alpha-1 receptors. Such molecules may have use in cardiovascular applications.

Example 4

Optimisation of Fadrozole from Lead Compound

Similar to Example 1, this example also demonstrates the optimisation and selection of a new drug from a lead compound: specifically, the design, selection and optimisation of the approved drug fadrozole from its lead compound.

Fadrozole, chemical name 4-(5,6,7,8-tetrahydroimidazo[1,5-a]pyridin-5-yl)benzonitrile, is an aromatase inhibitor, which is approved for the treatment of breast cancer. The structure-activity relationship data for the optimisation of fadrozole from its lead is described in "*Fadrozole hydrochloride: a potent, selective, nonsteroidal inhibitor of aromatase for the treatment of estrogen-dependent disease*" (Browne et al., (1991), *J. Med. Chem.*, 34(2), pp 725-736). Fadrozole is also described in an earlier publication by Cole et al., (1990), *J. Med. Chem.*, 1990, 33(11), pp 2933-2942, in which the inhibition of cytochrome P-450 aromatase is shown.

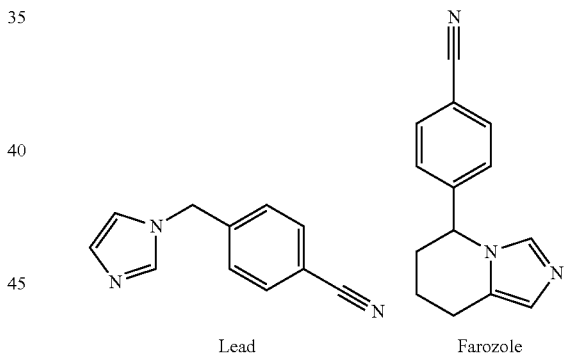

Lead             Farozole

To further demonstrate the utility of the invention in lead optimisation, the method of the invention was applied to the optimisation of the lead compound.

Chemical Transformation Library

The chemical transformation database was encoded in a library of approximately 700 unique transformations. The lead optimisation strategy was carried out over 6 iterations (generations), starting from the single lead molecule. Results were reviewed after 5 and 6 generations. At the end of the third to sixth generations, the number of unique compounds selected as the starting population for the next iteration was limited to the top 10,000 high-scoring molecules and 500 randomly selected lower scoring molecules to help increase the genetic variability of the molecular population.

Objective Scoring Method for Aromatase

Structure-activity data from the ChEMBL database was used to build a model of aromatase inhibitors. The lead structure and fadrozole were both present in the ChEMBL database: lead (Cytochrome P450 19A1; 50699; Binding IC50 15 nM; J. Med. Chem., (1991), 34:2, pp 725); fadrozole (1. Cytochrome P450 19A1; 50885; Binding Ki 1.5 nM; J. Med. Chem., (1990), 33:11, pp 2933: 2. Cytochrome P450 19A1; 50699; Binding IC50 39 nM; J. Med. Chem., (1991), 342, pp 725). However to prevent biasing the model only compounds that had been synthesised before the publication of Browne et al., (1991) were used to train the Bayesian model. Fadrozole itself was removed from the dataset, so although it was disclosed in 1990 it is not in the training set.

Biological activity for the designed compounds was predicted using a Laplacian Naïve Bayesian model, built following the methods described by Nidhi et al. (2006), as described for Example 1.

Two models were built (see Table 26). One model only contained compounds where there is a high confidence of them being correctly assigned to the target "aromatase" (assigned a confidence score greater than 6 in the ChEMBL database). A second model with ALL compounds assigned to aromatase inhibition was also trained. In the high confidence model, the number of active compounds was 108, and number of inactive was 9406; while in the model with all data, the number of active compounds was 109, and the number of inactive was 14104.

TABLE 26

Statistics from the leave-one-out validation

| Model | XV ROC AUC | Best Split | TP/FN FP/TN | # in Category |
|---|---|---|---|---|
| All data | 0.998 | 3.241 | 108/1 347/13757 | 109 |
| High Confidence | 0.997 | 3.849 | 107/1 224/9182 | 108 |

ROC = Receiver Operator Characteristics (to measure quality of predictive models (Triballeau et al., (2005), J. Med. Chem., 7(48), pp 2534-2547);
TP = True Positive;
N = False Negative;
FP = False Positive;
TN = True Negative Objective Scoring Method for ADME Properties Predicted ADME properties for the generated virtual compounds were scored using the StarDrop ADMET properties calculation and scoremax was defined as the maximum score (out of the four prediction profiles).

In addition to predicting ADME properties, StarDrop was also used to generate scoring functions to define a profile for the compounds (e.g. intravenous/oral CNS/oral non-CNS compound).

Iterative Evolution of Compound Generations

The Achievement Objective was defined as a Bayesian activity score of 100 and an ADME score of 50. Alternatively, other profiles can be used to set the Achievement Objective, such as an oral non-CNS score of 0.5.

The 700 (approx.) transformations were applied systematically to the single lead compound to produce a first generation of compounds which fulfilled the normal valency criteria and produced only one product from each transformation. Undesirable molecules were removed from each generation by applying the filters: Rule of Five; Unwanted Groups; maximum number of rotatable bonds=12; maximum number of rings of 9 atoms or higher=9 compounds. In each new population duplicate molecules were also removed. The library of transformations was then systematically applied to each member of the subsequent populations until the Stop Condition was satisfied.

To manage the number of molecules produced and limit the amount of processing time from the third generation the number of filtered molecules taken through to the next round was limited to the top 10,000 scoring molecules plus 500 randomly selected lower scoring molecules (with duplicates removed).

The stop condition was reached by an increase in synthetic complexity for prioritised compounds in the sixth generation. The final (sixth) generation of molecules was filtered using the same filters as in the preceding rounds.

The number of unique compounds in the filtered populations at the end of each generation is shown in Table 27.

TABLE 27

Number of Unique Compounds in filtered populations from each iteration

| Generation/Iteration | Number of Compounds per generation |
|---|---|
| 0 | 1 |
| 1 | 27 |
| 2 | 650 |
| 3 | 10411 |
| 4 | 10482 |
| 5 | 10457 |
| 6 | 10431 |

Objective Scoring of Results

After all filters had been applied to the final population, the ADMET score distribution for the remaining population of 10,431 virtual compounds was calculated. Compounds with a Bayesian score higher than 42 were selected to be scored by Stardrop.

Prioritisation of Optimisation Results

Prioritisation of virtual compounds was carried out as described in Example 1.

Figure 17:
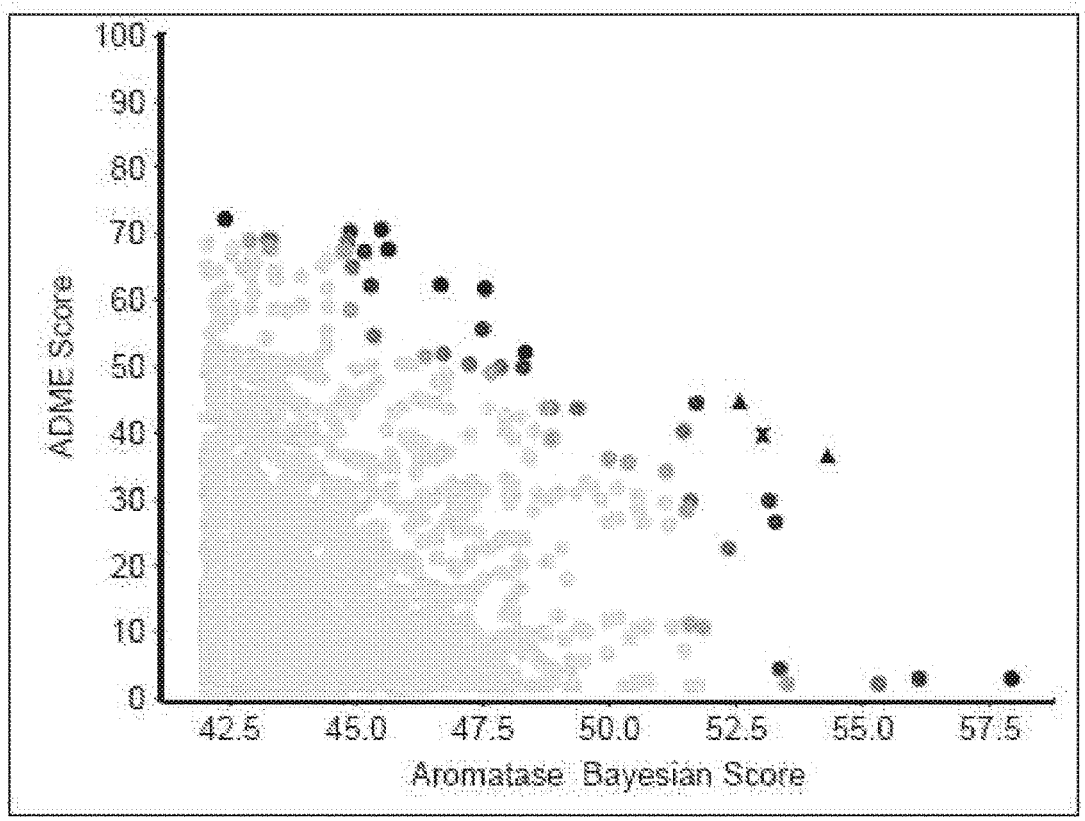
FIG. 17 shows the optimisation of compounds for binding to aromatase after the sixth iteration of the method of the invention. Bayesian score for predicted aromatase activity (x-axis) and maximum predicted ADME score (y-axis). The known aromatase drug, fadrozole is identified with an "X"; the two highest scoring compounds by vector distance are represented by solid triangles. The first Pareto front (Pareto Front=1) is coloured black; the second and lower Pareto fronts are coloured light grey.
Figure 18:
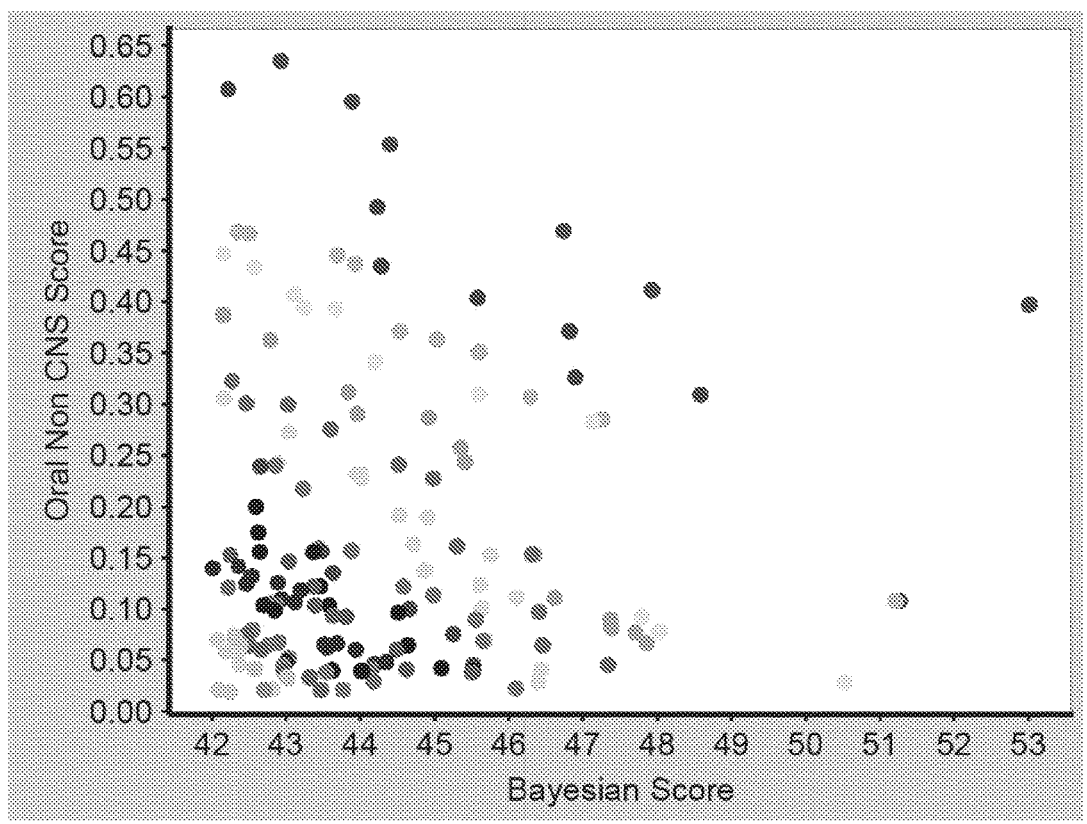
FIG. 18 shows the optimisation of compounds for binding to aromatase after the fifth iteration of the method of the invention. Bayesian score for predicted aromatase activity (x-axis) and maximum predicted ADME score (y-axis). Fadrozole (coordinates 53,04) is the highest ranking compound at this stage of the method.

Briefly, the generated compounds were ranked by Pareto front and by the vector distances calculated to the Achievement Objective. FIG. 17 shows the Pareto plot of the compounds of the sixth generation based on Bayesian and ADME scores. The first Pareto front is shown in black and the position of the known drug fadrozole, which is on the first Pareto front, is indicated by an "x". For comparison, FIG. 18 illustrates the Pareto plot for the compounds of the fifth generation based on Bayesian and ADME scores. Again, the first Pareto front is shown in black. In this round of evolution fadrozole was the top ranked compound at an approximate position of 53 (Bayesian score), 0.4 (oral non-CNS score).

Table 28 shows the scores and structures of the top 5 ranked compounds according to vector distance to the achievement objectives. Fadrozole (labelled 5_1, because it first appeared in the fifth iteration) with a vector distance of 48.108 is ranked third out of all of the prioritised compounds. The two compounds with slightly shorter vector distances to the achievement objectives, i.e. compounds 6_4 and 6_14, score lower on the synthetic accessibility score as defined by Ertl & Schuffenhauer (2009), J. Cheminformatics, 1(8), doi:10.1186/1758-2946-1-8.

TABLE 28

Predicted scores for the top five compounds evolved to bind aromatase

| Molecule | ADME Score | Name (Iteration_ID) | Aromatase Bayesian Score | Vector Distance |
|---|---|---|---|---|
| | 36.67 | 6_4 | 54.29 | 47.614 |
| | 44.97 | 6_14 | 52.55 | 47.716 |
| | 39.69 | 5_1 | 53.01 | 48.108 |
| | 44.59 | 6_18 | 51.7 | 48.602 |
| | 40.26 | 6_24 | 51.45 | 49.517 |

Automatic Design of Fadrozole

The known drug fadrozole was generated in the high confidence data model as the result of two different evolutionary paths involving five reaction/transformation steps. The reaction scheme below (Scheme II) illustrates the series of five reaction/transformation steps present in the transformation database of the invention that transformed the original lead compound to the known drug. In this scheme the reaction sequence is: (1) aromatic nitrogen to aromatic carbon, (2) methylation with chirality, (3) make spirocycle, (4) pyrrole to imidazole, and (5) methylene insertion. A second virtual synthesis route (not shown) is: (1) methylation, (2) methylation, (3) make spirocycle, (4) demethylation, and (5) methylene insertion.

The ChEMBL database also Includes information on the publications in which the various compounds are described, which means that it is possible to separate compounds by the year of publication. The synthetic route from lead to fadrozole was first published in 1991 (i.e. Browne et al.) as previously mentioned. However the first entry for fadrozole in the ChEMBL database dates from 1990, relating to an article reviewing molecules for the inhibition of Cytochrome P450 (i.e. Cole et al.). Hence, the model was built by taking compounds published before the lead to drug paper in 1991, and by removing the drug from the list of molecules.

Finally, ChEMBL provides a confidence score on the target assignment from the curation process. In this study, activities with a confidence score of at least 7 (Direct protein Scheme II

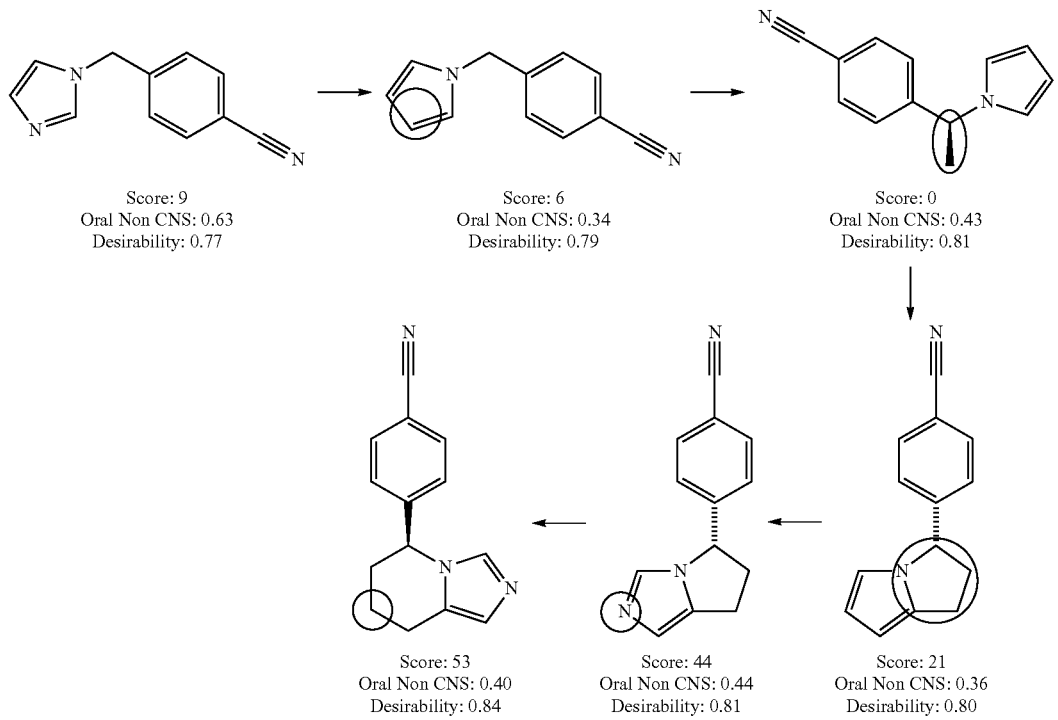

The above sequences of transformation steps do not necessary correspond to how the drug would be chemically synthesised in a laboratory. Thus, other synthesis routes may also be possible.

Model Building Methods:

Databases

ChEMBL_02 (http://ebi.ac.uk/chembl) was used for this study; ChEMBL is a database of bioactive molecules containing around 500,000 compounds with more than 2,400,000 endpoints published in medicinal literature over the last 30 years. The data was processed for this work by keeping only compounds with an activity measured in nM and which is inside the group of (IC50/Ki/Kd/EC50) with a protein target. Some custom filters were then applied (as activity>0).

Compounds were also standardised, and a unique tautomer form was kept, using the Pipeline Pilot components. Molecules with a molecular weight greater than 750 Da or with less than 4 atoms were discarded. Compounds with an primary activity other than against Cytochrome P450 19A1 (aromatase) were assigned to target 'none'.

complex subunits assigned) were kept. In total 9514 unique compounds were in the final set, of which 108 had a reported activity for aromatase of less than 10 μM.

Descriptors

Structural information using the Extended Connectivity Fingerprint (ECFP) were selected for use as descriptors (Rogers & Hahn (2010), *J. Chemical Information and Modeling*, 50, pp 742-54). These types of descriptors have been used in other studies with good results (Glick et al., 2006, Enrichment of high-throughput screening data with increasing levels of noise using support vector machines, recursive partitioning, and laplacian-modified naive bayesian classifiers, *J. Chemical Information and Modelling*, 46, pp 193-200; Hert et al., 2004, Comparison of topological descriptors for similarity-based virtual screening using multiple bioactive reference structures, *Org. Biomol. Chem.*, 2, pp 3256-3266; Klon et al., 2004, Finding More Needles in the Haystack: A Simple and Efficient Method for Improving High-Throughput Docking Results. *J. Med. Chem.*, 47, pp 2743). A neighbourhood of size 6 was selected to match the parameters used in the study of Nidhi et al. (2006, Prediction of biological targets for compounds using multiple-category Bayesian models trained on chemogenomics databases, *J. Chemical Information and Modeling*, 46, pp 1124-1133).

Bayesian Model

The Bayesian models were built according to the methods describe by Nidhi et al. (2006). A review of the application of Bayesian activity predictions in drug discovery can be found in Bender (2011)—to be published (Bender, 2011, Bayesian methods in virtual screening and chemical biology, *Methods in Molecular Biology*, Clifton, N.J., 672, pp 175-196.

The models were built using standard methods in the Accelrys's Pipeline Pilot software (Xia et al., 2004, Classification of Kinase Inhibitors Using a Bayesian Model, *J. Med. Chem.*, 47, pp 4463-4470), which automatically creates a Laplacian-modified Bayesian model for aromatase. It is a two-category model; good molecules are considered to be the active aromatase compounds, the other compounds are considered the bad molecules. A compound is considered "active" if the activity (e.g. binding affinity/inhibition constant) is below 10 μM. This information is used to build a high confidence model comprising molecules known to bind to relevant targets.

Once the model has been built it can be used to calculate a score for aromatase, and a high score provides more confidence of binding.

A second model was also built using all the available data (i.e not just active compounds), and was also used for prediction.

Validation

For validation, the data was split into two: compounds were clustered and split using the cluster ID to which they belong, with even numbers in the validation training set and odd numbers in the test set. The distribution of unique compounds, active and inactive for each set is in Table 29.

TABLE 29

Distribution of compounds in high confidence data set

| Set | Active | Inactive |
|---|---|---|
| Validation Training | 58 | 4467 |
| Validation Test | 50 | 4939 |
| Whole Set | 108 | 9406 |

The test set was scored using the model built with the validation training set (Table 30). The area under the ROC curve (AUC) was calculated to judge the quality of the model. For All data, the whole set is scored using the whole set model.

TABLE 30

Scoring of data sets by measuring area under curve for ROC data

| Set | AUC |
|---|---|
| Validation Training | 0.998 (Excellent) |
| Validation Test | 0.973 (Excellent) |
| Whole Set | 0.998 (Excellent) |

Calculation

Virtual molecules can be processed by assigning each compound a score for aromatase, and then ranking the population of compounds from best (highest score) to worst (lowest score).

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the scope of the invention, which is defined by the claims.

We thank Bryan L. Roth MD, PhD (Director) of the NIMH PDSP at the University of North Carolina at Chapel Hill, and Jamie Driscol (Project Officer) at NIMH, Bethesda Md., USA for assistance with assay measurements.

The invention claimed is:

1. A method for designing and synthesizing a drug compound having a particular property for a desired use, the method comprising:

defining a set of n achievement objectives ($O^A_{1-n}$), where n is at least one;

defining a population ($P_{G=0}$) of at least one molecule;

selecting an initial population ($P_{parent}$) of at least one molecule ($I_1$-$I_m$) from the population ($P_{G=0}$);

evaluating, by a computer device, members ($I_1$-$I_m$) of the initial population ($P_{parent}$) against at least one of the n achievement objectives ($O^A_{1-x}$), where x is from 1 to n;

wherein the evaluating the members ($I_1$-$I_m$) of the initial population ($P_{parent}$) comprises:

calculating the parameters of each member ($I_1$-$I_m$) of the initial population f($P_{parent}$) for the at least one achievement objective ($O^A_{1-x}$); and calculating vector distance (VD) from each member ($I_1$-$I_m$) to the at least one achievement objective ($O^A_{1-x}$);

wherein the vector distance (VD) between each member ($I_1$-$I_m$) and the at least one achievement objective ($O^A_{1-x}$) is defined as:

$$VD\ V_A = \sqrt{\sum_{p=1}^{n}(x_I^p - x_A^p)^2},$$

wherein a desired value of each of the achievement objectives ($O^A_{1-n}$) has coordinates ($x_I^1, \ldots, x_I^n$), and a calculated value of the corresponding parameter p for each member ($I_1$-$I_m$) of the initial population has coordinates ($x_A^1, \ldots, x_A^n$); and determining whether a stop condition is satisfied;

(a) upon determining that the stop condition is satisfied, performing a first process including:

ranking members ($I_1$-$I_m$) of the evaluated initial population ($P_{parent}$) according to a shortest vector distance (VD) and optionally Pareto frontier to the set of n achievement objectives ($O^A_{1-n}$), wherein a first ranked member ($I_1$-$I_m$) has a shortest vector distance (VD) to the set of n achievement objectives ($O^A_{1-n}$) compared to any other vector distance (VD) of any other ranked member ($I_1$-$I_m$), and identifying a set of z ranked members including at least the first ranked member ($I_1$-$I_m$) of the evaluated initial population ($P_{parent}$), where z is 1, 2, 5, 10, 20, 50 or 100; and (b) upon determining that the stop condition is not satisfied, performing a second process including:

performing a first iteration (G=1) of an evolutionary algorithm to generate and evaluate a new population ($P_G$) of at least one molecule by:
  transforming at least one member of the parent population ($P_{parent}$) to generate a transformed population ($P_{transformed}$) of at least one molecule;
  defining a new population ($P_G$) of at least one molecule, the new population ($P_G$) comprising at least one member of the transformed population ($P_{transformed}$);
  optionally evaluating the new population ($P_G$) against at least one achievement objective ($O^A_{1-x}$), and selecting molecules from the evaluated population ($P_G$) by applying a strategy function (S);
  defining a new population ($P_{G+1}$) of at least one molecule ($I_1$-$I_m$); and
  evaluating members ($I_1$-$I_m$) of the new population ($P_{G+1}$) against the at least one achievement objective ($O^A_{1-x}$);
    wherein the evaluating the new population ($P_G$) comprises performing the calculation of vector distance (VD) to the at least one achievement objective ($O^A_{1-x}$) to identify a set of z ranked members including at least a first ranked member ($I_1$-$I_m$) of the evaluated new population ($P_G$) having a shortest vector distance to the at least one achievement objective ($O^A_{1-x}$); and
selectively synthesizing the drug compound based on any of the members of the identified set of z ranked members ($I_1$-$I_m$) of the evaluated initial population ($P_{parent}$) or based on any of the members of the identified set of z ranked members ($I_1$-$I_m$) of the evaluated new population ($P_G$).

2. The method of claim 1, further comprising:
generating further populations ($P_G$; $P_{G+1}$) of molecules and evaluating each one by an iterative process until a predefined stop condition is satisfied.

3. The method of claim 1, wherein the evaluating comprises:
  calculating the parameters of each member ($I_1$-$I_m$) of the initial population ($P_{parent}$) for each of the at least one achievement objective ($O^A_{1-x}$); and
  calculating the vector distance (VD) of each member ($I_1$-$I_m$) of the initial population ($P_{parent}$) to the at least one achievement objective ($O^A_{1-x}$); and
  optionally calculating and assigning a Pareto frontier ranking to members ($I_1$-$I_m$) of the initial population ($P_{parent}$).

4. The method of claim 1, wherein the ranking comprises:
  calculating the parameters of each member ($I_1$-$I_m$) of the initial population ($P_{parent}$) for each of the n achievement objectives ($O^A_{1-n}$); and
  calculating the vector distance (VD) and optionally the Pareto rank of each member ($I_1$-$I_m$) of the initial population ($P_{parent}$) to each of the n achievement objectives ($O^A_{1-n}$).

5. The method of claim 1, wherein the evaluating comprises:
  calculating the parameters of each member ($I_1$-$I_m$) of the new population ($P_{G+1}$) for each of the at least one achievement objective ($O^A_{1-x}$); and
  calculating the vector distance (VD) of each member ($I_1$-$I_m$) of the new population ($P_{G+1}$) to the at least one achievement objective ($O^A_{1-x}$); and
  optionally calculating and assigning a Pareto frontier ranking to members ($I_1$-$I_m$) of the new population ($P_{G+1}$).

6. The method of claim 1, further comprising:
if the stop condition is not satisfied:
  defining the evaluated new population ($P_{G+1}$) as a new parent population ($P_{parent}$) of at least one molecule ($I_1$-$I_m$); and
  performing a second iteration (G=2) of the evolutionary algorithm by repeating the steps of section (b);
if the stop condition is satisfied:
  ranking members ($I_1$-$I_m$) of the new population ($P_{G+1}$) according to vector distance (VD) and optionally Pareto frontier to the set of n achievement objectives ($O^A_{1-n}$); and
  identifying at least the first ranked member ($I_1$-$I_m$) of the evaluated new population ($P_{G+1}$).

7. The method of claim 6, wherein the ranking comprises:
  calculating the parameters of each member ($I_1$-$I_m$) of the new population ($P_{G+1}$) for the n achievement objectives ($O^A_{1-n}$); and
  calculating the vector distance (VD) and optionally the Pareto frontier of each member ($I_1$-$I_m$) of the new population ($P_{G+1}$) to the n achievement objectives ($O^A_{1-n}$).

8. The method of claim 6, wherein $P_G = P_{parent} + P_{transformed}$.

9. The method of claim 6, further comprising:
applying at least one filter (F) to remove molecules that fail at least one predefined criteria of the filter (F).

10. The method of claim 9, wherein the at least one filter (F) is applied to molecules of the population ($P_G$) before evaluating the population ($P_G$) against at least one achievement objective ($O^A_{1-x}$); and/or
wherein the at least one filter (F) is applied to molecules of the population ($P_{G+1}$) before ranking members ($I_1$-$I_m$) of the new population ($P_{G+1}$).

11. The method of claim 9, wherein the at least one predefined criteria of the at least one filter (F) is selected from at least one of:
  no duplicate molecules from the population ($P_G$); non-broken molecule requirement; solubility; drug-like properties; molecular weight; hydrogen bonding capacity; octanol-water partition coefficient; toxicity; unwanted group definition; total polar surface area; number of rotatable bonds; molecule size; number of functional groups; and number of heteroatoms.

12. The method of claim 1, wherein evaluating the population ($P_G$) against at least one achievement objective ($O^A_{1-x}$), and selecting molecules from the evaluated population ($P_G$) by applying a strategy function (S), comprises:
  identifying at least one desired activity (A) of an optimized molecule and defining a strategy function (S) to score each member ($I_1$-$I_m$) of the population ($P_G$) against one or more of the at least one desired activity ($A_{1-n}$);
  calculating the parameters of each member ($I_1$-$I_m$) of the population ($P_G$) for at least one of the achievement objectives ($O^A_{1-x}$) relevant to the one or more desired activity ($A_{1-n}$);
  determining the predicted activity (Prediction 1 to Prediction n) of each member ($I_1$-$I_m$) of the population ($P_G$) for the one or more desired activity ($A_{1-n}$);
  selecting the sub-population (Pete) of molecules of the population ($P_G$) that satisfy the strategy function (S); and
  optionally selecting a sub-population ($P_{random}$) of at least one molecule from the sub-population ($P_{non-elite}$) of molecules that do not satisfy the strategy function (S).

13. The method of claim 12, wherein the new population ($P_{G+1}$) of at least one molecule ($I_1$-$I_m$) comprises $P_{elite}$ or $P_{elite}+P_{random}$.

14. The method of claim 12, wherein the strategy function (S) is satisfied for molecules of the population ($P_G$) where the predicted activity (Prediction 1) is greater than the sum of the mean predicted activity ([Prediction 1]Mean) and the standard deviation of the predicted activity ([Prediction 1]StdDev) for all members ($I_1$-$I_m$) of the population ($P_G$); where:

Prediction 1>[Prediction 1]Mean+[Prediction 1]StdDev.

15. The method of claim 12, wherein the at least one molecule ($P_{random}$) from the sub-population ($P_{non-elite}$) of molecules that do not satisfy the strategy function (S) is selected at random from the sub-population ($P_{non-elite}$).

16. The method of claim 12, wherein the strategy function (S) is based on two or more desired activities ($A_{1-n}$) of an optimized molecule.

17. The method of claim 12, wherein the at least one desired activity (A) of an optimized molecule is selected from one or more of:
- predicted activity against one or more target molecule;
- predicted relative activity against one target molecule compared to another molecule;
- predicted selectivity for one or more target molecule over another molecule;
- predicted relative selectivity for more than one target molecule;
- predicted drug-like properties/scores;
- prioritization of one or more ADME property;
- prioritization of drug-like properties over one or more activity or specificity; and
- prioritization of vector prioritization over Pareto frontier.

18. The method of claim 1, wherein the transformations are derived from a database of known chemical transformations, and/or the transformations include a null-transformation, and/or the transformations are derived from a combination of known chemical transformations and genetic algorithms.

19. The method of claim 18, further comprising:
applying all transformations in the database to all members of the population ($P_{parent}$).

20. The method of claim 1, further comprising:
transforming at least one of the molecules of the population ($P_{G=0}$) to create a transformed population of molecules before selecting the initial population ($P_{parent}$).

21. A method for designing and synthesizing a drug compound having a particular property for a desired use, the method comprising:
defining a set of n achievement objectives ($O^A_{1-n}$), where n is at least one;
defining a population ($P_{G=0}$) of at least one molecule;
selecting an initial population ($P_{parent}$) of at least one molecule ($I_1$-$I_m$) from the population ($P_{G=0}$);
evaluating, by a computer device, members ($I_1$-$I_m$) of the initial population ($P_{parent}$) against at least one of the n achievement objectives ($O^A_{1-x}$), where x is from 1 to n;
wherein the evaluating the members ($I_1$-$I_m$) of the initial population ($P_{parent}$) comprises:
calculating the parameters of each member ($I_1$-$I_m$) of the initial population f($P_{parent}$) for the at least one achievement objective ($O^A_{1-x}$); and
calculating vector distance (VD) from each member ($I_1$-$I_m$) to the at least one achievement objective ($O^A_{1-x}$);

wherein the vector distance (VD) between each member ($I_1$-$I_m$) and the at least one achievement objective ($O^A_{1-x}$) is defined as:

$$VD\ V_A = \sqrt{\sum_{p=1}^{n}(x_I^p - x_A^p)^2},$$

wherein a desired value of each of the achievement objectives ($O^A_{1-n}$) has coordinates ($x_I^1, \ldots, x_I^n$), and a calculated value of the corresponding parameter p for each member ($I_1$-$I_m$) of the initial population has coordinates ($x_A^1, \ldots, x_A^n$); and determining whether a stop condition is satisfied;

(a) upon determining that the stop condition is satisfied, performing a first process including:
ranking members ($I_1$-$I_m$) of the evaluated initial population ($P_{parent}$) according to a shortest vector distance (VD) and optionally Pareto frontier to the set of n achievement objectives ($O^A_{1-n}$), wherein a first ranked member ($I_1$-$I_m$) has a shortest vector distance (VD) to the set of n achievement objectives ($O^A_{1-n}$) compared to any other vector distance (VD) of any other ranked member ($I_1$-$I_m$), and
identifying highest ranking members of the ranked members ($I_1$-$I_m$) including at least the first ranked member ($I_1$-$I_m$) of the evaluated initial population ($P_{parent}$); and (b) upon determining that the stop condition is not satisfied, performing a second process including:
performing a first iteration (G=1) of an evolutionary algorithm to generate and evaluate a new population ($P_G$) of at least one molecule by:
transforming at least one member of the parent population ($P_{parent}$) to generate a transformed population ($P_{transformed}$) of at least one molecule;
defining a new population ($P_G$) of at least one molecule, the new population ($P_G$) comprising at least one member of the transformed population ($P_{transformed}$);
optionally evaluating the new population ($P_G$) against at least one achievement objective ($O^A_{1-x}$), and selecting molecules from the evaluated population ($P_G$) by applying a strategy function (S);
defining a new population ($P_{G+1}$) of at least one molecule ($I_1$-$I_m$); and
evaluating members ($I_1$-$I_m$) of the new population ($P_{G+1}$) against the at least one achievement objective ($O^A_{1-x}$);
wherein the evaluating the new population ($P_G$) comprises performing the calculation of vector distance (VD) to the at least one achievement objective ($O^A_{1-x}$) to identify highest ranking members including at least a first ranked member ($I_1$-$I_m$) of the evaluated new population ($P_G$) having a shortest vector distance to the at least one achievement objective ($O^A_{1-x}$); and
selectively synthesizing the drug compound based on any of the members of the identified highest ranking members ($I_1$-$I_m$) of the evaluated initial population ($P_{parent}$) or based on any of the members of the identified highest ranking members ($I_1$-$I_m$) of the evaluated new population ($P_G$).

* * * * *